(12) United States Patent
Miura et al.

(10) Patent No.: US 9,688,704 B2
(45) Date of Patent: Jun. 27, 2017

(54) AZOLE SILANE COMPOUND, SURFACE TREATMENT SOLUTION, SURFACE TREATMENT METHOD, AND USE THEREOF

(71) Applicant: SHIKOKU CHEMICALS CORPORATION, Kagawa (JP)

(72) Inventors: Shozo Miura, Kagawa (JP); Takayuki Murai, Kagawa (JP); Naoto Okumura, Kagawa (JP); Miya Tanioka, Kagawa (JP); Masato Katsumura, Kagawa (JP); Noriaki Yamaji, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 0 days.

(21) Appl. No.: 14/902,182

(22) PCT Filed: Jun. 30, 2014

(86) PCT No.: PCT/JP2014/067469
§ 371 (c)(1),
(2) Date: Dec. 30, 2015

(87) PCT Pub. No.: WO2015/002158
PCT Pub. Date: Jan. 8, 2015

(65) Prior Publication Data
US 2016/0368935 A1      Dec. 22, 2016

(30) Foreign Application Priority Data

Jul. 2, 2013   (JP) .................................. 2013-138541
Aug. 27, 2013  (JP) .................................. 2013-175314
(Continued)

(51) Int. Cl.
C07F 7/18       (2006.01)
C09J 5/02       (2006.01)
(Continued)

(52) U.S. Cl.
CPC ............ C07F 7/1836 (2013.01); B32B 37/12 (2013.01); B32B 37/14 (2013.01); C08K 5/5442 (2013.01);
(Continued)

(58) Field of Classification Search
CPC .................................. C07F 7/1836; C09J 5/02
See application file for complete search history.

(56) References Cited

U.S. PATENT DOCUMENTS

| | | | |
|---|---|---|---|
| 4,729,986 A | 3/1988 | Olson | |
| 2002/0147358 A1 | 10/2002 | Yanagisawa et al. | |
| 2010/0284917 A1 | 11/2010 | Kustner et al. | |

FOREIGN PATENT DOCUMENTS

| | | |
|---|---|---|
| JP | 5-39295 | 2/1993 |
| JP | 5-186479 | 7/1993 |

(Continued)

OTHER PUBLICATIONS

International Search Report issued Sep. 22, 2014 in corresponding International Application No. PCT/JP2014/067469 (with English translation).

(Continued)

*Primary Examiner* — Daniel Lee
(74) *Attorney, Agent, or Firm* — Wenderoth, Lind & Ponack, L.L.P.

(57) ABSTRACT

Objects are to provide a novel azole silane compound, a synthesis method thereof, and a silane coupling agent containing the azole silane compound as a component, and to provide a surface treatment solution using the azole silane compound, a surface treatment method, and a bonding method of two materials different in the quality of material. The azole silane compound of the present invention is a compound represented by the specific chemical formula (I-1) or (II-1).

38 Claims, 24 Drawing Sheets

(30) Foreign Application Priority Data

Oct. 2, 2013 (JP) ................................ 2013-206978
Dec. 25, 2013 (JP) ................................ 2013-266400

(51) Int. Cl.

| | | |
|---|---|---|
| H05K 3/38 | (2006.01) | |
| C08K 5/544 | (2006.01) | |
| B32B 37/12 | (2006.01) | |
| B32B 37/14 | (2006.01) | |
| H05K 1/03 | (2006.01) | |
| H05K 1/09 | (2006.01) | |
| H05K 3/28 | (2006.01) | |

(52) U.S. Cl.
CPC .............. *C09J 5/02* (2013.01); *H05K 1/0306* (2013.01); *H05K 1/09* (2013.01); *H05K 3/389* (2013.01); *B32B 2311/12* (2013.01); *B32B 2315/02* (2013.01); *B32B 2315/08* (2013.01); *B32B 2333/04* (2013.01); *B32B 2363/00* (2013.01); *B32B 2377/00* (2013.01); *B32B 2457/08* (2013.01); *C09J 2400/163* (2013.01); *C09J 2400/166* (2013.01); *C09J 2400/226* (2013.01); *C09J 2400/228* (2013.01); *C09J 2433/008* (2013.01); *C09J 2463/008* (2013.01); *C09J 2479/088* (2013.01); *H05K 3/28* (2013.01); *H05K 2201/0154* (2013.01); *H05K 2203/124* (2013.01)

(56) References Cited

FOREIGN PATENT DOCUMENTS

| | | | | |
|---|---|---|---|---|
| JP | 05186479 A | * | 7/1993 | .............. C07F 7/182 |
| JP | 6-279461 | | 10/1994 | |
| JP | 7-286160 | | 10/1995 | |
| JP | 8-505837 | | 6/1996 | |
| JP | 2002-308887 | | 10/2002 | |
| JP | 2002-363189 | | 12/2002 | |
| JP | 2006-45189 | | 2/2006 | |
| JP | 2009-19266 | | 1/2009 | |
| JP | 2009-263790 | | 11/2009 | |
| JP | 2013-014752 | | 1/2013 | |
| KR | 10-2013-0044533 | | 5/2013 | |
| KR | 20130044533 A | * | 5/2013 | |
| WO | 2009/040114 | | 4/2009 | |
| WO | 2012/031183 | | 3/2012 | |

OTHER PUBLICATIONS

Zhang, Dongmei et al., "Synthesis and lead(II) sorption of silica gel-immobilized, di-ionizable calix[4]arenes", *Tetrahedron*, 2007, vol. 63, No. 23, pp. 5076-5082.
CAS Registry No. 1609930-50-8.
Notification of Reasons for Refusal issued Jun. 27, 2016 in corresponding Japanese Application No. 2013-138541 (with English translation).
Notification of Reasons for Refusal issued Jun. 27, 2016 in corresponding Japanese Application No. 2013-175314 (with English translation).
Partial Supplementary European Search Report issued Feb. 23, 2017 in corresponding European Application No. 14820454.8.
First Office Action issued Feb. 27, 2017 in corresponding Chinese Application No. 201480037728.X (with English translation).
J.L. Liu et al., "Molecular Construction and Photophysical Properties of Luminescent Covalently Bonded Lanthanide Hybrid Materials Obtained by Grafting Organic Ligands Containing 1,2,4-Triazole on Silica by Mercapto Modification", Journal of Physical Chemistry 112:14168-14178 (2008).
Extended Eurpean Search Report, issued May 12, 2017 in corresponding European Patent Application No. 14820454.8.
Fujiwara et al., "Switching catalytic reaction conducted in pore void of mesoporous material by redox gate control", Chem. Commun. 44:4635-4637 (2006).

* cited by examiner

AZOLE SILANE COMPOUND, SURFACE TREATMENT SOLUTION, SURFACE TREATMENT METHOD, AND USE THEREOF

TECHNICAL FIELD

The present invention relates to a novel azole silane compound, and a surface treatment solution using the azole silane compound, a surface treatment method and use thereof.

BACKGROUND ART

In recent years, as to printed wiring boards, increase in a number of layers has been advancing in order to respond to reduction in size, thickness and the like of electronic devices and electronic components. A so-called multilayer printed wiring board is being manufactured by stacking a circuit board for outer layer or a copper foil on a circuit board for inner layer, which is provided with a circuit composed of a copper foil or the like on one side or both sides, through a prepreg, and integrating them.

By the way, in such a multilayer printed wiring board, it is an important problem to ensure a bonding property between a copper circuit formed on the circuit board for inner layer and an insulating adherent resin of the prepreg for stacking the circuit board for outer layer or copper foil.

Patent Document 1 discloses an invention relating to a copper foil surface treatment agent which improves a bonding property between a copper foil and a prepreg and solder heat resistance of a copper-clad laminate obtained by bonding the copper foil to the prepreg.

This document discloses the combination use of a trialkoxysilane compound having an imidazole ring with a tetraalkoxysilane compound as components of the surface treatment agent.

Patent Document 2 discloses an invention relating to a copper surface conditioning composition and a surface treatment method, which can maintain an adhesion property between copper and an insulating material such as a resin without performing a roughening treatment such as etching of a surface of copper.

This document discloses that silane coupling agents having an alkoxy group, such as silanol and trisilanol is preferred as a component of the surface conditioning composition in view of an excellent adhesion property to an insulating material and that, among them, a silane coupling agent having a mercapto group is preferred in view of improving an adhesion property between copper and an insulating material such as an epoxy resin.

Also, it is disclosed that a solution containing the surface conditioning composition is able to be prepared by dissolving the composition in a mixed solvent of water and an organic solvent. Further, it is disclosed that after bringing the solution into contact with a surface of copper, drying may be performed after washing with water or drying may be performed without washing with water, and that in the case of performing the drying after washing with water, a film having an uniform thickness can be obtained, on the other hand, in the case of performing the drying without washing with water, a high adhesion property to the insulating material can be obtained.

Patent Document 3 discloses an invention relating to a production method of a silane coupling agent solution, a silane coupling agent solution, a surface treatment method of a base material using the same, and the like.

This document discloses that by mixing an organic silicon compound with water to sufficiently form silanol groups and then further mixing with an alcohol, a high silanolation rate can be actualized, uniform coating is possible and excellent adhesion property can be actualized, and that the silanolation rate is preferably from 60 to 100%, and more preferably from 80 to 100%.

Also, as the organic silicon compound, 3-mercaptopropylmethyldimethoxysilane and 3-mercaptopropyltrimethoxysilane are disclosed.

The problem of the invention is to improve an adhesion property between a base material composed of an organic polymer compound or an inorganic material and a liquid crystalline compound, and there is no mention about an adhesion property in the case where copper is the base material.

Patent Document 4 discloses an invention relating to a silane coupling agent and a polymer composition.

This document discloses, as a component of a silane coupling agent used as a primer for bonding glass or metal to rubber, various substances having a structure where a nitrogen-containing heterocyclic ring such as triazole or thiazole is connected to a silyl group such as a trimethoxysilyl group or a triethoxysilyl group, through an organic group having a thioether (sulfide) bond or the like.

PRIOR ART DOCUMENT

Patent Document

Patent Document 1: JP-A-H07-286160
Patent Document 2: JP-A-2009-263790
Patent Document 3: JP-A-2006-045189
Patent Document 4: JP-A-2002-363189

SUMMARY OF THE INVENTION

Problems that the Invention is to Solve

An object of the present invention is to provide a novel azole silane compound, a synthesis method thereof, and a silane coupling agent containing the azole silane compound as a component, in order to enhance a bonding property between two materials different in the quality of material such as metal, an inorganic material and a resin material, and to provide a surface treatment solution using the azole silane compound, a surface treatment method, and a bonding method of different materials.

Means for Solving the Problems

As a result of the intensive investigations to solve the problems described above, the present inventors have recognized that a novel azole silane compound is able to be synthesized by reacting an azole compound with a halogenated alkylsilane compound or an isocyanatoalkylsilane compound, and they have completed the present invention.

Also, as a result of the intensive investigations to solve the problems described above, the present inventors have found that the desired object is achieved by using an azole silane compound having an azole ring and a thioether bond (—S—) or a disulfide bond (—S—S—) in its molecule, and they completed the present invention.

That is, the present invention encompasses the following (1) to (33).
(1) An azole silane compound represented by the following chemical formula (I-1) or (II-1):

[Chem. 1]

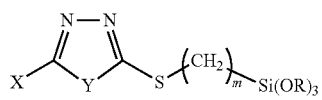 (I-1)

(in formula (I-1), X represents a hydrogen atom, —CH₃, —NH₂, —SH, or —SCH₃; Y represents —NH— or —S—; R represents —CH₃ or —CH₂CH₃; and m represents an integer of from 1 to 12)

[Chem. 2]

 (II-1)

(in formula (II-1), A₁ represents

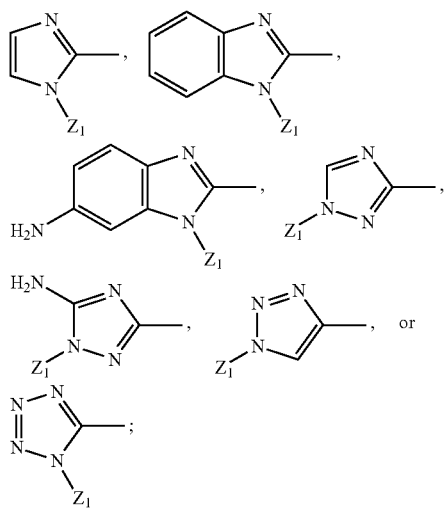

$Z_1$ represents —CO—NH—(CH₂)$_m$—Si(OR)₃;
R represents —CH₃ or —CH₂CH₃; and
m represents an integer of from 1 to 12).

(2) A synthesis method of an azole silane compound represented by the following chemical formula (I-1):

[Chem. 3]

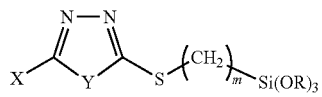 (I-1)

(in formula (I-1), X represents a hydrogen atom, —CH₃, —NH₂, —SH or —SCH₃; Y represents —NH— or —S—; R represents —CH₃ or —CH₂CH₃; and m represents an integer of from 1 to 12).

The synthesis method contains a step of reacting an azole compound represented by the following chemical formula (I-2) with a halogenated alkylsilane compound represented by the following chemical formula (I-3) in the presence of a dehydrohalogenation agent:

[Chem. 4]

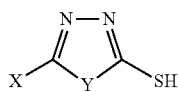 (I-2)

(in formula (I-2), X represents a hydrogen atom, —CH₃, —NH₂, —SH or —SCH₃; and Y represents —NH— or —S—);

[Chem. 5]

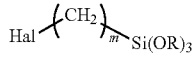 (I-3)

(in formula (I-3), R represents —CH₃ or —CH₂CH₃, m represents an integer of from 1 to 12; and Hal represents a chlorine atom, a bromine atom or an iodine atom).

(3) A synthesis method of an azole silane compound represented by the following chemical formula (II-1):

[Chem. 6]

 (II-1)

(in formula (II-1), A₁ represents

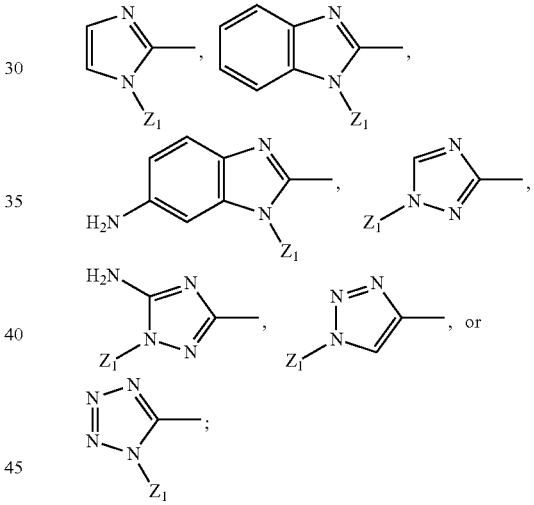

$Z_1$ represents —CO—NH—(CH₂)$_m$—Si(OR)₃;
R represents —CH₃ or —CH₂CH₃; and
m represents an integer of from 1 to 12).

The synthesis method contains a step of reacting an azole compound represented by the following chemical formula (II-2) with an isocyanatoalkylsilane compound represented by the following chemical formula (II-3):

[Chem. 7]

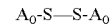 (II-2)

(in formula (II-2), A₀ represents

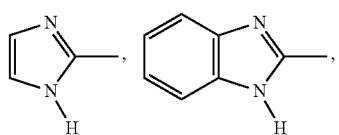

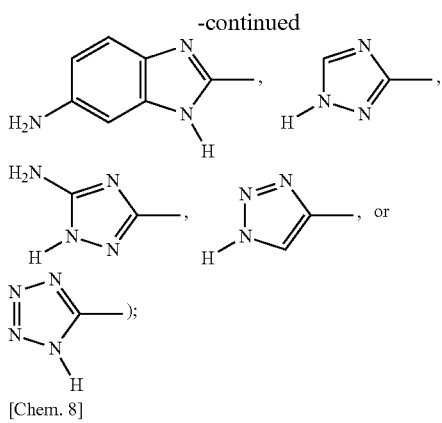

[Chem. 8]

$$OCN-(CH_2)_m-Si(OR)_3 \quad (II-3)$$

(in formula (II-3), R represents —CH$_3$ or —CH$_2$CH$_3$, and m represents an integer of from 1 to 12).

(4) A silane coupling agent containing an azole silane compound represented by the following chemical formula (III-1) or (IV-1) as a component:

[Chem. 9]

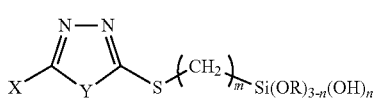

(III-1)

(in formula (III-1), X represents a hydrogen atom, —CH$_3$, —NH$_2$, —SH or —SCH$_3$; Y represents —NH— or —S—; R represents —CH$_3$ or —CH$_2$CH$_3$, m represents an integer of from 1 to 12; and n represents 0 or an integer of from 1 to 3);

[Chem. 10]

$$A_2\text{-S—S-}A_2 \quad (IV-1)$$

(in formula (IV-1), A$_2$ represents

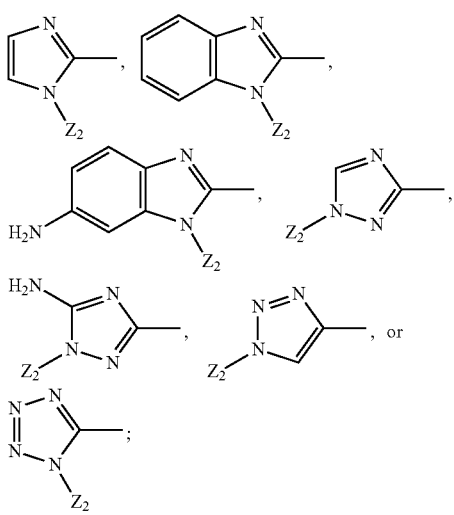

$Z_2$ represents —CO—NH—(CH$_2$)$_m$—Si(OR)$_{3-n}$(OH)$_n$;
R represents —CH$_3$ or —CH$_2$CH$_3$;
m represents an integer of from 1 to 12; and
n represents 0 or an integer of from 1 to 3).

(5) A surface treatment solution containing an azole silane compound represented by the following chemical formula (III-1) or (IV-1):

[Chem. 11]

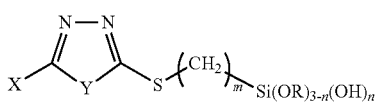

(III-1)

(in formula X represents a hydrogen atom, —CH$_3$, —NH$_2$, —SH or —SCH$_3$; Y represents —NH— or —S—; R represents —CH$_3$ or —CH$_2$CH$_3$, m represents an integer of from 1 to 12; and n represents 0 or an integer of from 1 to 3);

[Chem. 12]

$$A_2\text{-S—S-}A_2 \quad (IV-1)$$

(in formula (IV-1), A$_2$ represents

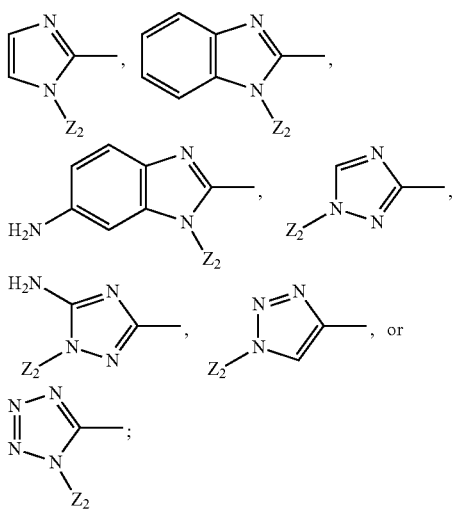

$Z_2$ represents —CO—NH—(CH$_2$)$_m$—Si(OR)$_{3-n}$(OH)$_n$;
R represents —CH$_3$ or —CH$_2$CH$_3$;
m represents an integer of from 1 to 12; and
n represents 0 or an integer of from 1 to 3).

(6) The surface treatment solution according to the above (5), which is used for treating a surface of at least one selected from the group consisting of a metal, an inorganic material and a resin material.

(7) The surface treatment solution according to the above (5), which is used for bonding at least two materials selected from the group consisting of a metal, an inorganic material and a resin material.

(8) The surface treatment solution according to the above (6) or (7), in which the metal is at least one selected from the group consisting of copper, aluminum, titanium, nickel, tin, iron, silver, gold, and alloys thereof.

(9) The surface treatment solution according to the above (6) or (7), in which the metal is copper or a copper alloy.

(10) The surface treatment solution according to the above (6) or (7), in which the inorganic material is at least one selected from the group consisting of silicon, a ceramic and a glass.
(11) The surface treatment solution according to the above (10), in which the ceramic is at least one selected from the group consisting of alumina, silicon carbide, aluminum nitride, silicon nitride, and barium titanate.
(12) The surface treatment solution according to the above (6) or (7), in which the resin material is at least one selected from the group consisting of an acrylate resin, an epoxy resin and a polyimide resin.
(13) A surface treatment method of metal, containing bringing the surface treatment solution described in the above (5) into contact with a surface of the metal.
(14) The surface treatment method of metal according to the above (13), in which the metal is at least one selected from the group consisting of copper, aluminum, titanium, nickel, tin, iron, silver, gold, and alloys thereof.
(15) The surface treatment method of metal according to the above (13), in which the metal is copper or a copper alloy.
(16) The surface treatment method of metal according to the above (15), in which before bringing the surface treatment solution into contact with a surface of copper or a copper alloy, an aqueous solution containing a copper ion is brought into contact with the surface of copper or a copper alloy.
(17) The surface treatment method of metal according to the above (15) or (16), in which after bringing the surface treatment solution into contact with a surface of copper or a copper alloy, an aqueous acidic solution or an aqueous alkaline solution is brought into contact with the surface of copper or a copper alloy.
(18) A surface treatment method of an inorganic material, containing bringing the surface treatment solution described in the above (5) into contact with a surface of the inorganic material.
(19) The surface treatment method of an inorganic material according to the above (18), in which the inorganic material is at least one selected from the group consisting of silicon, a ceramic and a glass.
(20) The surface treatment method of an inorganic material according to the above (19), in which the ceramic is at least one selected from the group consisting of alumina, silicon carbide, aluminum nitride, silicon nitride, and barium titanate.
(21) A surface treatment method of a resin material, containing bringing the surface treatment solution described in the above (5) into contact with a surface of the resin material.
(22) The surface treatment method of a resin material according to the above (21), in which the resin material is at least one selected from the group consisting of an acrylate resin, an epoxy resin and a polyimide resin.
(23) A bonding method between a metal and a resin material, containing bringing the surface treatment solution described in the above (5) into contact with at least one of the metal and the resin material to form a chemical film on the at least one thereof, and bonding the metal and the resin material to each other through the chemical film.
(24) A bonding method between an inorganic material and a resin material, containing bringing the surface treatment solution described in the above (5) into contact with at least one of the inorganic material and the resin material to form a chemical film on the at least one thereof, and bonding the inorganic material and the resin material to each other through the chemical film.
(25) A bonding method between a metal and an inorganic material, containing bringing the surface treatment solution described in the above (5) into contact with at least one of the metal and the inorganic material to form a chemical film on the at least one thereof, and bonding the metal and the inorganic material to each other through the chemical film.
(26) A printed wiring board in which two materials selected from the group consisting of a metal, an inorganic material and a resin material are bonded through a chemical film formed from the surface treatment solution described in the above (5).
(27) An electronic device in which two materials selected from the group consisting of a metal, an inorganic material and a resin material are bonded through a chemical film formed from the surface treatment solution described in the above (5).
(28) An insulating composition containing the silane coupling agent described in the above (4) and a resin material or an inorganic material.
(29) The insulating composition according to the above (28), in which the resin material is at least one selected from the group consisting of an acrylate resin, an epoxy resin and a polyimide resin.
(30) The insulating composition according to the above (28), in which the inorganic material is at least one selected from the group consisting of silicon, a ceramic and a glass.
(31) An insulating material containing the insulating composition described in any one of the above (28) to (30).
(32) A printed wiring board containing an insulating layer obtained from the insulating composition described in any one of the above (28) to (30).
(33) An electronic device containing an insulating layer obtained from the insulating composition described in any one of the above (28) to (30).

Advantage of the Invention

The azole silane compound according to the present invention is suitable for a component of a silane coupling agent. Also, since the azole silane compound used as the component is a substance having an azole ring, the silane coupling agent according to the present invention is expected to exert a function of preventing metal from corrosion, which is the feature of the azole compound, and exert a function of curing an epoxy resin or a urethane resin.

Also, according to the surface treatment solution containing the azole silane compound according to the present invention, the bonding property between two materials different in the quality of material, specifically, metal and an inorganic material, metal and a resin material, or an inorganic material and a resin material, can be enhanced.

MODE FOR CARRYING OUT THE INVENTION

Figure 1:
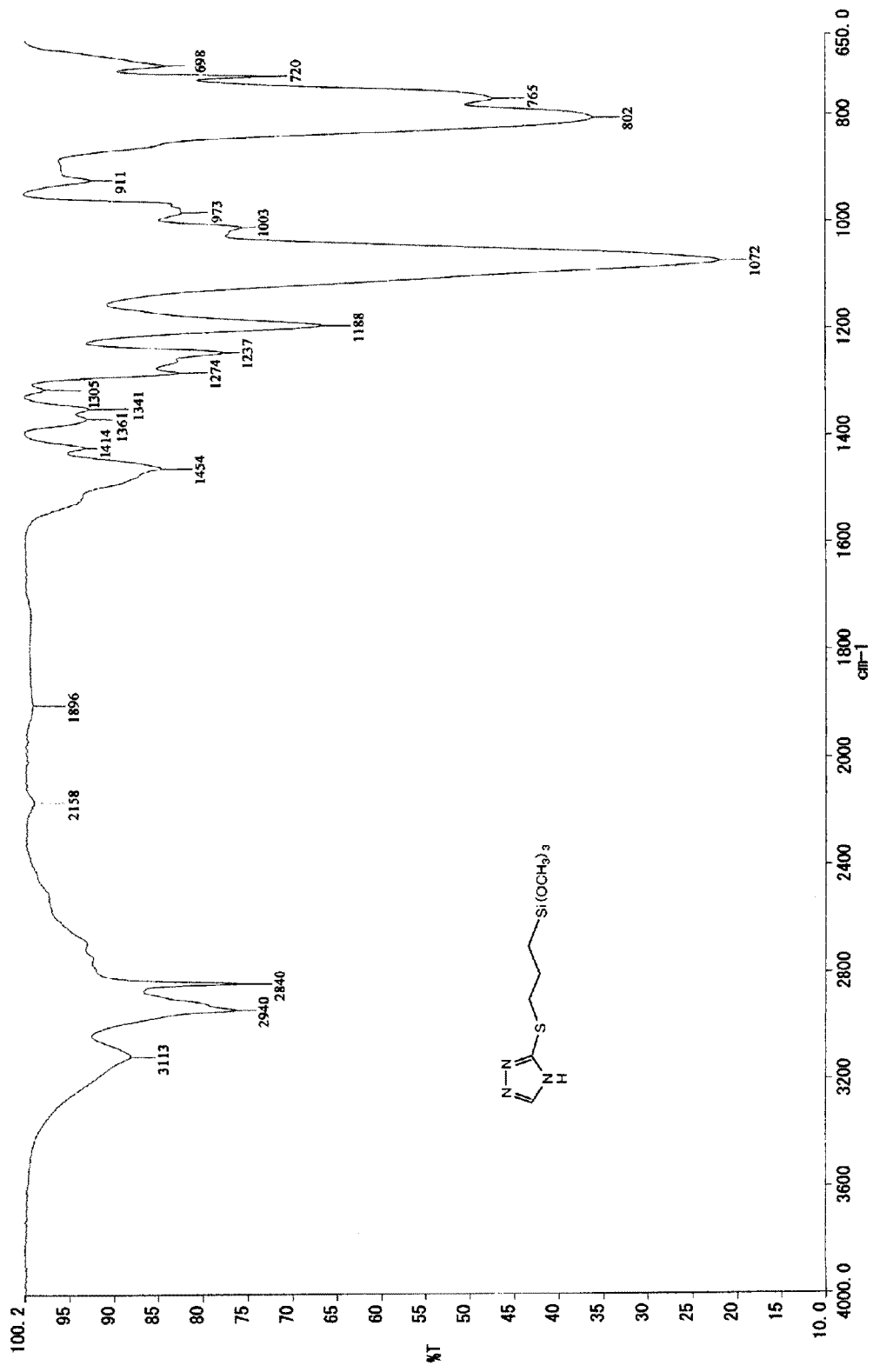
FIG. 1 is an IR spectral chart of the oily material obtained in Example 1-1.

The present invention will be described in detail hereinafter.

(Azole Silane Compound)

The azole silane compound according to the present invention is represented by the following chemical formula (I-1) or (II-1).

[Chem. 13]

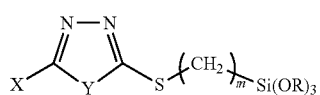

(I-1)

(in formula (I-1), X represents a hydrogen atom, —$CH_3$, —$NH_2$, —SH or —$SCH_3$; Y represents —NH— or —S—; R represents —$CH_3$ or —$CH_2CH_3$; and m represents an integer of from 1 to 12).

[Chem. 14]

$A_1$-S—S-$A_1$     (II-1)

(In formula (II-1), $A_1$ represents

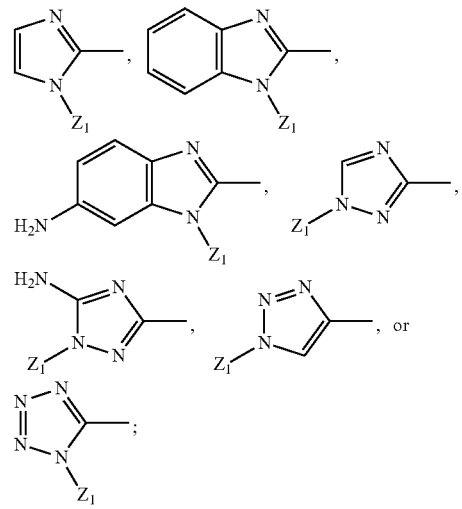

$Z_1$ represents —CO—NH—$(CH_2)_m$—$Si(OR)_3$;
R represents —$CH_3$ or —$CH_2CH_3$; and
m represents an integer of from 1 to 12).

(Azole Silane Compound Represented by Chemical Formula (I-1))

Examples of the azole silane compound represented by chemical formula (I-1) includes:
3-trimethoxysilylmethylthio-1,2,4-triazole,
3-[3-(trimethoxysilyl)propylthio]-1,2,4-triazole,
3-[3-(triethoxysilyl)propylthio]-1,2,4-triazole,
3-[6-(triethoxysilyl)hexylthio]-1,2,4-triazole,
3-[12-(trimethoxysilyl)dodecylthio]-1,2,4-triazole,
3-methyl-5-[2-(triethoxysilyl)ethylthio]-1,2,4-triazole,
3-methyl-5-[4-(trimethoxysilyl)butylthio]-1,2,4-triazole,
3-methyl-5-[10-(trimethoxysilyl)decylthio]-1,2,4-triazole,
3-amino-5-triethoxysilylmethylthio-1,2,4-triazole,
3-amino-5-[3-(trimethoxysilyl)propylthio]-1,2,4-triazole,
3-amino-5-[6-(trimethoxysilyl)hexylthio]-1,2,4-triazole,
3-amino-5-[12-(trimethoxysilyl)dodecylthio]-1,2,4-triazole,
3-amino-5-[3-(triethoxysilyl)propylthio]-1,2,4-triazole,
3-mercapto-5-[2-(trimethoxysilyl)ethylthio]-1,2,4-triazole,
3-mercapto-5-[5-(trimethoxysilyl)pentylthio]-1,2,4-triazole,
3-mercapto-5-[8-(trimethoxysilyl)octylthio]-1,2,4-triazole,
3-methylthio-5-[3-(trimethoxysilyl)propylthio]-1,2,4-triazole,
3-methylthio-5-[10-(trimethoxysilyl)decylthio]-1,2,4-triazole, and
3-methylthio-5-[4-(triethoxysilyl)butylthio]-1,2,4-triazole (they are cases where Y is —NH—), and
2-trimethoxysilylmethylthio-1,3,4-thiadiazole,
2-[6-(trimethoxysilyl)hexylthio]-1,3,4-thiadiazole,
2-[8-(triethoxysilyl)octylthio]-1,3,4-thiadiazole,
5-methyl-2-[3-(trimethoxysilyl)propylthio]-1,3,4-thiadiazole,
5-methyl-2-[5-(trimethoxysilyl)pentylthio]-1,3,4-thiadiazole,
5-methyl-2-[12-(triethoxysilyl)dodecylthio]-1,3,4-thiadiazole,
2-amino-5-[3-(trimethoxysilyl)propylthio]-1,3,4-thiadiazole,
2-amino-5-[8-(trimethoxysilyl)octylthio]-1,3,4-thiadiazole,
2-amino-5-[2-(triethoxysilyl)ethylthio]-1,3,4-thiadiazole,
2-amino-5-[3-(triethoxysilyl)propylthio]-1,3,4-thiadiazole,
2-mercapto-5-[3-(trimethoxysilyl)propylthio]-1,3,4-thiadiazole, 2-mercapto-5-[5-(trimethoxysilyl)pentylthio]-1,3,4-thiadiazole,
2-mercapto-5-[3-(triethoxysilyl)propylthio]-1,3,4-thiadiazole,
2-mercapto-5-[10-(triethoxysilyl)decylthio]-1,3,4-thiadiazole,
2-methylthio-5-[3-(trimethoxysilyl)propylthio]-1,3,4-thiadiazole,
2-methylthio-5-[4-(trimethoxysilyl)butylthio]-1,3,4-thiadiazole,
2-methylthio-5-[3-(triethoxysilyl)propylthio]-1,3,4-thiadiazole, and
2-methylthio-5-[8-(triethoxysilyl)octylthio]-1,3,4-thiadiazole (they are cases where Y is —S—).

The azole silane compound represented by chemical formula (I-1) (hereinafter, also referred to as azole silane compound (I-1)) can be obtained by reacting an azole compound represented by the following chemical formula (I-2) (hereinafter, also referred to as azole compound (I-2)) with a halogenated alkylsilane compound represented by the following chemical formula (I-3) (hereinafter, also referred to as halogenated alkylsilane compound (I-3)).

[Chem. 15]

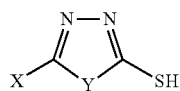

(I-2)

(In formula (I-2), X and Y have the same meanings as described above).

[Chem. 16]

(I-3)

(In formula (I-3), R and m have the same meanings as described above; and Hal represents a chlorine atom, a bromine atom or an iodine atom).

Specifically, as shown in the reaction scheme (A), the azole silane compound (I-1) can be synthesized generally in a high yield by reacting the azole compound (I-2), which is a corresponding precursor, with the halogenated alkylsilane compound (I-3) in the presence of a dehydrohalogenation agent in an appropriate amount of a reaction solvent at an appropriate reaction temperature for an appropriate reaction time.

Reaction scheme (A)

[Chem. 17]

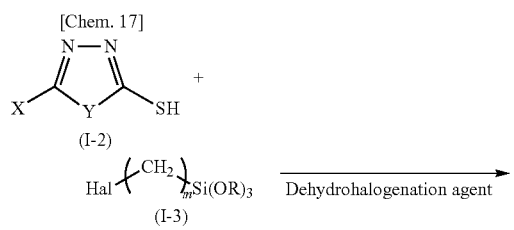

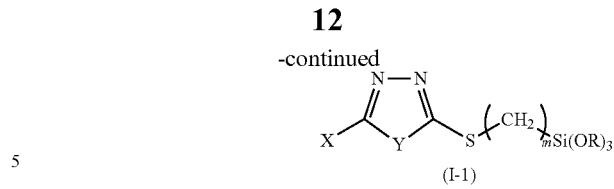

(I-1)

(In formulae (I-1) to (I-3), X, Y, R, Hal and m have the same meanings as described above).

Examples of the azole compound (I-2), which serves as a precursor, includes:
3-mercapto-1,2,4-triazole,
3-methyl-5-mercapto-1,2,4-triazole,
3-amino-5-mercapto-1,2,4-triazole,
3,5-dimercapto-1,2,4-triazole,
3-mercapto-5-methylthio-1,2,4-triazole,
2-mercapto-1,3,4-thiadiazole,
2-mercapto-5-methyl-1,3,4-thiadiazole,
2-amino-5-mercapto-1,3,4-thiadiazole,
2,5-dimercapto-1,3,4-thiadiazole, and
2-mercapto-5-methylthio-1,3,4-thiadiazole.

Examples of the halogenated alkylsilane compound (I-3) includes:
chloromethyltrimethoxysilane,
chloromethyltriethoxysilane,
2-chloroethyltrimethoxysilane,
2-chloroethyltriethoxysilane,
3-chloropropyltrimethoxysilane,
3-chloropropyltriethoxysilane,
3-bromopropyltrimethoxysilane,
3-bromopropyltriethoxysilane,
3-iodopropyltrimethoxysilane,
3-iodopropyltriethoxysilane,
4-bromobutyltrimethoxysilane,
4-bromobutyltriethoxysilane,
5-bromopentyltrimethoxysilane,
5-bromopentyltriethoxysilane,
6-bromohexyltrimethoxysilane,
6-bromohexyltriethoxysilane,
8-bromooctyltrimethoxysilane,
8-bromooctyltriethoxysilane,
10-bromodecyltrimethoxysilane,
10-bromodecyltriethoxysilane,
12-bromododecyltrimethoxysilane, and
12-bromododecyltriethoxysilane.

The reaction solvent is not particularly limited as long as it is an inert solvent for the azole compound (I-2) and the halogenated alkylsilane compound (I-3), and examples thereof includes hydrocarbon solvents such as hexane, toluene and xylene; ether solvents such as diethyl ether, tetrahydrofuran, dioxane, and cyclopentyl methyl ether; ester solvents such as ethyl acetate and butyl acetate; alcohol solvents such as methanol and ethanol; amide solvents such as N,N-dimethylformamide, N,N-dimethylacetamide and N-methylpyrrolidone; ketone solvents such as acetone, methyl ethyl ketone, methyl isobutyl ketone, and cyclohexanone; acetonitrile, dimethylsulfoxide, and hexamethylphosphoramide.

Examples of the dehydrohalogenation agent includes:
alkali metal alkoxides such as sodium methoxide, sodium ethoxide, potassium methoxide, and potassium tert-butoxide; alkali carbonates such as sodium carbonate, sodium hydrogen carbonate and potassium hydrogen carbonate; organic bases such as diazabicycloundecene; and sodium hydride.

The reaction between the azole compound (I-2) and the halogenated alkylsilane compound (I-3) according to the present invention proceeds stoichiometrically as shown in the reaction scheme (A), but it is preferred that the use amount (charged amount) of the halogenated alkylsilane compound to the use amount (charged amount) of the azole compound is set to an appropriate ratio in a range of from 0.8 to 1.2 times by mole in consideration of the factors such as the kinds of starting materials and reaction solvent used and the reaction scale, as well as the reaction temperature and the reaction time.

When the charged amount of the halogenated alkylsilane compound is more than 1.2 times by mole, there is a possibility that the compound is polymerized to be gelled, whereas when it is less than 0.8 times by mole, there is a possibility that purity of the product is reduced or separation operation of the product becomes cumbersome.

Also, since the dehydrohalogenation agent is used for the purpose of neutralizing hydrogen halide by-produced in the reaction of the azole compound with the halogenated alkylsilane compound, the use amount (charged amount) thereof may be equimolar or more to the use amount of the halogenated alkylsilane compound.

The reaction temperature is not particularly limited as long as it is in the temperature rage where a mercapto group of the azole compound reacts with the halogenated alkylsilane compound, and it is preferably in a range of from 0 to 150° C., and more preferably in a range of from 5 to 100° C.

The reaction time is appropriately determined according to the reaction temperature set, and it is preferably in a range of from 30 minutes to 10 hours, and more preferably in a range of from 1 to 5 hours.

(Azole silane compound represented by chemical formula (II-1))

Examples of the azole silane compound represented by chemical formula (II-1) include:
2,2'-dithiobis[1-(trimethoxysilyl)methylcarbamoyl]-1H-imidazole,
2,2'-dithiobis{1-[3-(trimethoxysilyl)propylcarbamoyl]-1H-imidazole},
2,2'-dithiobis{1-[3-(triethoxysilyl)propylcarbamoyl]-1H-imidazole},
2,2'-dithiobis{1-[6-(triethoxysilyl)hexylcarbamoyl]-1H-imidazole},
2,2'-dithiobis{1-[3-(trimethoxysilyl)propylcarbamoyl]-1H-benzimidazole},
2,2'-dithiobis{1-[3-(triethoxysilyl)propylcarbamoyl]-1H-benzimidazole},
2,2'-dithiobis{1-[12-(trimethoxysilyl)dodecylcarbamoyl]-1H-benzimidazole},
2,2'-dithiobis{5-amino-1-[3-(trimethoxysilyl)propylcarbamoyl]-1H-benzimidazole},
2,2'-dithiobis{5-amino-1-[3-(triethoxysilyl)propylcarbamoyl]-1H-benzimidazole},
2,2'-dithiobis{5-amino-1-[2-(triethoxysilyl)ethylcarbamoyl]-1H-benzimidazole},
3,3'-dithiobis{1-[3-(trimethoxysilyl)propyl carbamoyl]-1H-1,2,4-triazole},
3,3'-dithiobis{1-[3-(triethoxysilyl)propyl carbamoyl]-1H-1,2,4-triazole},
3,3'-dithiobis{1-[4-(trimethoxysilyl)butylcarbamoyl]-1H-1,2,4-triazole},
3,3'-dithiobis{5-amino-1-[3-(trimethoxysilyl)propyl carbamoyl]-1H-1,2,4-triazole},
3,3'-dithiobis{5-amino-1-[3-(triethoxysilyl)propyl carbamoyl]-1H-1,2,4-triazole},
3,3'-dithiobis{5-amino-1-[10-(triethoxysilyl)decylcarbamoyl]-1H-1,2,4-triazole},
4,4'-dithiobis{1-[3-(trimethoxysilyl)propylcarbamoyl]-1H-1,2,3-triazole},
4,4'-dithiobis{1-[3-(triethoxysilyl)propyl carbamoyl]-1H-1,2,3-triazole},
4,4'-dithiobis{1-[5-(trimethoxysilyl)pentylcarbamoyl]-1H-1,2,3-triazole},
5,5'-dithiobis{1-[3-(trimethoxysilyl)propylcarbamoyl]-1H-tetrazole},
5,5'-dithiobis{1-[3-(triethoxysilyl)propyl carbamoyl]-1H-tetrazole}, and
5,5'-dithiobis{1-[8-(triethoxysilyl)octylcarbamoyl]-1H-tetrazole}.

The azole silane compound represented by chemical formula (II-1) (hereinafter, also referred to as azole silane compound (II-1)) can be obtained by reacting an azole compound represented by the following chemical formula (II-2) (hereinafter, also referred to as azole compound (II-2)) with an isocyanatoalkylsilane compound represented by the following chemical formula (II-3) (hereinafter, also referred to as isocyanatoalkylsilane compound (II-3)).

[Chem. 18]

$$A_0\text{-S}\text{—}\text{S}\text{-}A_0 \qquad (\text{II-2})$$

(In formula (II-2), $A_0$ represents

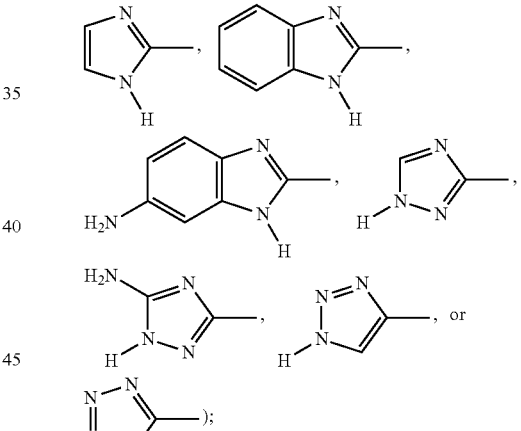

);

[Chem. 19]

$$\text{OCN}\text{—}(\text{CH}_2)_m\text{—}\text{Si}(\text{OR})_3 \qquad (\text{II-3})$$

(In formula (II-3), R represents —$CH_3$ or —$CH_2CH_3$, and m represents an integer of from 1 to 12).

Specifically, as shown in the reaction scheme (B), the azole silane compound (II-1) can be synthesized generally in a high yield by reacting the azole compound (II-2), which is a corresponding precursor, with the isocyanatoalkylsilane compound (II-3) in an appropriate amount of a reaction solvent at an appropriate reaction temperature for an appropriate reaction time. The reaction scheme (B) is an example in which 2,2'-dithiodi(1H-imidazole) (Azole compound (II-2a)) is used as the azole compound (II-2).

Reaction scheme (B)

[Chem. 20]

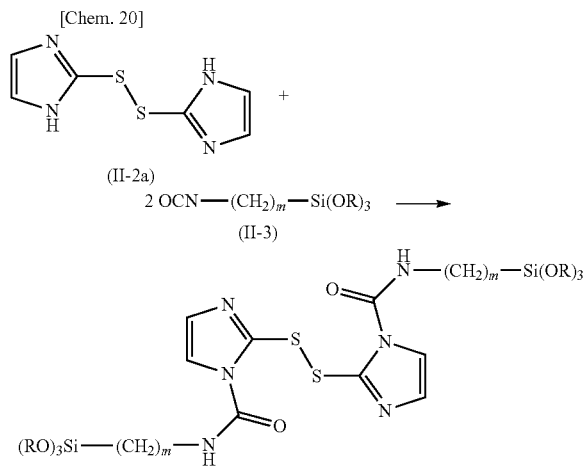

(In formulae (II-1a) and (II-3), R and m have the same meanings as described above).

Examples of the azole compound (II-2), which serves as a precursor, includes:
2,2'-dithiodi(1H-imidazole),
2,2'-dithiodi(1H-benzimidazole),
2,2'-dithiobis(5-amino-1H-benzimidazole),
3,3'-dithiodi(1H-1,2,4-triazole),
3,3'-dithiobis(5-amino-1H-1,2,4-triazole),
4,4'-dithiodi(1H-1,2,3-triazole), and
5,5'-dithiodi(1H-tetrazole).

Examples of the isocyanatoalkylsilane compound (II-3) includes:
isocyanatomethyltrimethoxysilane,
isocyanatomethyltriethoxysilane,
2-isocyanatoethyltrimethoxysilane,
2-isocyanatoethyltriethoxysilane,
3-isocyanatopropyltrimethoxysilane,
3-isocyanatopropyltriethoxysilane,
4-isocyanatobutyltrimethoxysilane,
4-isocyanatobutyltriethoxysilane,
5-isocyanatopentyltrimethoxysilane,
5-isocyanatopentyltriethoxysilane,
6-isocyanatohexyltrimethoxysilane,
6-isocyanatohexyltriethoxysilane,
8-isocyanatooctyltrimethoxysilane,
8-isocyanatooctyltriethoxysilane,
10-isocyanatodecyltrimethoxysilane,
10-isocyanatodecyltriethoxysilane,
12-isocyanatododecyltrimethoxy silane, and
12-isocyanatododecyltriethoxysilane.

The reaction solvent is not particularly limited as long as it is an inert solvent for the azole compound (II-2) and the isocyanatoalkylsilane compound (II-3), and examples thereof includes hydrocarbon solvents such as pentane, hexane, heptane, toluene, and xylene; ether solvents such as diethyl ether, tetrahydrofuran, dioxane, and cyclopentyl methyl ether; ester solvents such as ethyl acetate and butyl acetate; amide solvents such as formamide, dimethylformamide, dimethylacetamide, pyrrolidone, and N-methylpyrrolidone; ketone solvents such as acetone, methyl ethyl ketone, methyl isobutyl ketone, and cyclohexanone; and dimethylsulfoxide.

The reaction between the azole compound (II-2) and the isocyanatoalkylsilane compound (II-3) according to the present invention proceeds stoichiometrically as exemplified in the reaction scheme (B), but it is preferred that the use amount (charged amount) of the isocyanatoalkylsilane compound to the use amount (charged amount) of the azole compound is set to an appropriate ratio in a range of from 1.6 to 2.4 times by mole in consideration of the factors such as the kinds of starting materials and reaction solvent used and the reaction scale, as well as the reaction temperature and the reaction time.

When the charged amount of the isocyanatoalkylsilane compound is more than 2.4 times by mole, there is a possibility that the compound is polymerized to be gelled, whereas when it is less than 1.6 times by mole, there is a possibility that purity of the product is reduced or separation operation of the product becomes cumbersome.

The reaction temperature is not particularly limited as long as it is in the temperature rage where the endocyclic nitrogen (—NH—) of the azole compound reacts with the isocyanato group (—NCO) of the isocyanatoalkylsilane compound, and is preferably in a range of from 0 to 100° C., and more preferably in a range of from 5 to 60° C.

The reaction time is appropriately determined according to the reaction temperature set, and is preferably in a range of from 30 minutes to 20 hours, and more preferably in a range of from 1 to 15 hours.

(Silane Coupling Agent)

The silane coupling agent according to the present invention contains an azole silane compound represented by the following chemical formula (III-1) or (IV-1) as a component.

[Chem. 21]

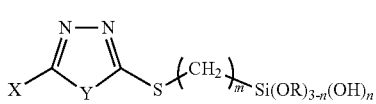

(III-1)

(In formula X represents a hydrogen atom, —CH$_3$, —NH$_2$, —SH or —SCH$_3$; Y represents —NH— or —S—; R represents —CH$_3$ or —CH$_2$CH$_3$, m represents an integer of from 1 to 12; and n represents 0 or an integer of from 1 to 3);

[Chem. 22]

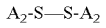

$A_2$-S—S-$A_2$   (IV-1)

(In formula (IV-1), $A_2$ represents

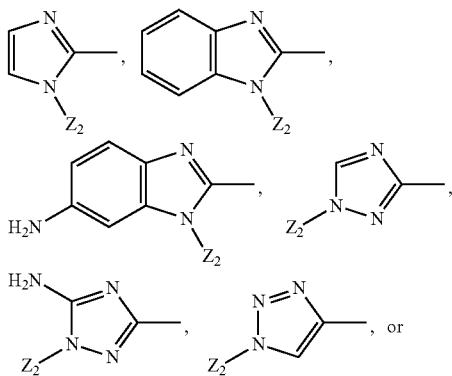

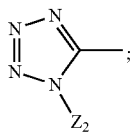

$Z_2$ represents —CO—NH—(CH$_2$)$_m$—Si(OR)$_{3-n}$(OH)$_n$;
R represents —CH$_3$ or —CH$_2$CH$_3$;
m represents an integer of from 1 to 12; and
n represents 0 or an integer of from 1 to 3).

In the case of using the silane coupling agent containing the azole silane compound represented by chemical formula (III-1) or (IV-1) as a component, a method of adding the agent as it is or by dissolving it in an organic solvent or the like to a base material as in the case of using a conventional silane coupling agent, or a method of treating a surface of the base material with it, can be adopted.

Examples of the method of treating a surface of a base material includes: (a) a method of spraying, on a base material, a surface treatment solution prepared by diluting an appropriate amount of the silane coupling agent with an organic solvent, (b) a method of spraying, on a base material, a surface treatment solution prepared by diluting the silane coupling agent with water and an organic solvent, (c) a method of spraying, on a base material, a surface treatment solution prepared by diluting the silane coupling agent with water, (d) a method of immersing a base material in a surface treatment solution prepared by diluting the silane coupling agent with an organic solvent, (e) a method of immersing a base material in a surface treatment solution prepared by diluting the silane coupling agent with water and an organic solvent, and (f) a method of immersing a base material in a surface treatment solution prepared by diluting the silane coupling agent with water.

Examples of the organic solvent includes: hydrocarbon solvents such as benzene, toluene, xylene, heptane, hexane, cyclohexane, and n-octane; halogenated hydrocarbon solvents such as dichloromethane, dichloroethane, carbon tetrachloride, chloroform, chlorobenzene, dichlorobenzene, and trichlorobenzene; ketone solvents such as acetone, methyl ethyl ketone and methyl isobutyl ketone; ether solvents such as diethyl ether, tetrahydrofuran, dioxane, ethylene glycol monomethyl ether (methyl cellosolve), ethylene glycol monoethyl ether (ethyl cellosolve), ethylene glycol monobutyl ether (butyl cellosolve), and diethylene glycol monobutyl ether; and alcohol solvents such as methanol, ethanol, 1-propanol, 2-propanol, n-butyl alcohol, sec-butyl alcohol, tert-butyl alcohol, ethylene glycol, diethylene glycol, and propylene glycol.

Examples of the base material used in the present invention includes: granulated, needle-like, fibriform, plate-like, and amorphous base materials formed from metal, an inorganic material, a resin material and the like.

Examples of the metal includes: copper, aluminum, titanium, nickel, tin, iron, silver, gold, and alloys thereof.

As to specific examples of the alloy, a copper alloy is not particularly limited as long as it is an alloy containing copper, and examples thereof includes alloys of Cu—Ag based, Cu—Te based, Cu—Mg based, Cu—Sn based, Cu—Si based, Cu—Mn based, Cu—Be—Co based, Cu—Ti based, Cu—Ni—Si based, Cu—Zn—Ni based, Cu—Cr based, Cu—Zr based, Cu—Fe based, Cu—Al based, Cu—Zn based, and Cu—Co based.

Also, examples of other alloys include an aluminum alloy (Al—Si alloy), a nickel alloy (Ni—Cr alloy), and an iron alloys (Fe—Ni alloy or stainless steel).

Of these metals, copper and a copper ally are preferred.

Examples of the inorganic material includes: silicon, a ceramic, an inorganic material used as a filler, and glass.

Specific examples thereof include: silicon; silicon compounds such as silicon carbide, silica, glass, a diatomaceous earth, calcium silicate, a talc, a glass bead, a sericite activated white earth, and bentonite; oxides such as alumina, zinc oxide, iron oxide, magnesium oxide, tin oxide, and titanium oxide; hydroxides such as magnesium hydroxide, aluminum hydroxide and basic magnesium carbonate; carbonates such as calcium carbonate, zinc carbonate, hydrotalcite, and magnesium carbonate; sulfates such as barium sulfate and gypsum; titanates such as barium titanate; and nitrides such as aluminum nitride and silicon nitride.

Of the inorganic materials, silicon, a ceramic (alumina, silicon carbide, aluminum nitride, silicon nitride, and barium titanate) and glass are preferred.

Examples of the resin material include: an acrylate resin, an epoxy resin, a polyimide resin, a bismaleimide resin, a maleimide resin, a cyanate resin, a polyphenylene ether resin, a polyphenylene oxide resin, an olefin resin, a fluorine-containing resin, a polyetherimide resin, a polyether ether ketone resin, and a liquid crystal resin, and may be a combination thereof by mixing or modifying with each other.

Of these resin materials, an acrylate resin, an epoxy resin and a polyimide resin are preferred.

By applying a surface treatment to the base material, it is possible to improve affinity (bonding property, adhesion property) between the base materials different in the quality of material.

In order to enhance the effect of the treatment, the base material surface-treated may be subjected to a heat treatment.

(Surface Treatment Solution)

The surface treatment solution according to the present invention is a surface treatment solution containing the azole silane compound represented by chemical formula (III-1) or (IV-1) as a silane coupling agent.

(Surface Treatment Solution Containing Azole Silane Compound of Chemical Formula (III-1))

The surface treatment solution of the first group according to the present invention (hereinafter, also simply referred to as a surface treatment solution according to the present invention) contains the azole silane compound represented by chemical formula (III-1) (hereinafter, also referred to as azole silane compound (III-1)) as a silane coupling agent, and the azole silane compound encompasses the azole silane compounds represented by chemical formula (I-1) and chemical formulae (III-1a) to (III-1c).

[Chem. 23]

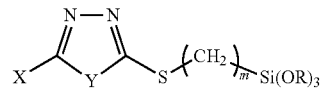

(I-1)

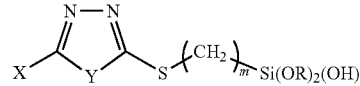

(III-1a)

-continued

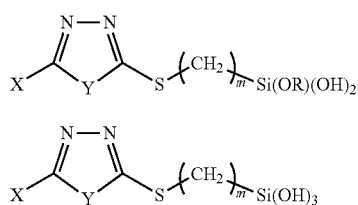

(III-Ib)

(III-1c)

(In formulae (I-1) and to (III-1c), X, Y, R and m have the same meanings as described above).

That is, the azole silane compound (I-1) is an azole silane compound (trialkoxy body) where n is 0 in chemical formula (III-1).

Similarly, the azole silane compound represented by chemical formula (III-1a) (hereinafter, also referred to as azole silane compound (III-1a)) is an azole silane compound where n is 1; the azole silane compound represented by chemical formula (III-1b) (hereinafter, also referred to as azole silane compound (III-1b)) is an azole silane compound where n is 2; and the azole silane compound represented by chemical formula (III-1c) (hereinafter, also referred to as azole silane compound (III-1c)) is an azole silane compound where n is 3.

The azole silane compounds (III-1a) to (III-1c) are species generated by hydrolysis of the azole silane compound (I-1) present in the surface treatment solution, and they are suitable for the component of silane coupling agent as well as the azole silane compound (I-1) which is a trialkoxy body. Also, the azole silane compounds (III-1a) to (III-1c) can be used by extracting from the surface treatment solution by, for example, removing the volatile content from the surface treatment solution.

In the practice of the present invention, it is preferred to use the azole silane compound (I-1) as a raw material for preparing the surface treatment solution.

Examples of the azole silane compound (I-1) are same as those described above.

The surface treatment solution of the first group according to the present invention is prepared by mixing the azole silane compound (I-1) with water or an organic solvent, and water may be used together with an organic solvent.

As to the preparation method of the surface treatment solution, an organic solvent may be added after mixing the azole silane compound with water, a mixed solution of water and an organic solvent may be added to the compound, or water may be added after mixing the compound with an organic solvent.

As the water used for the preparation of the surface treatment solution, pure water such as ion-exchanged water or distilled water is preferred.

Examples of the organic solvent preferably includes, in addition to, for example, methanol, ethanol, 1-propanol, 2-propanol, butanol, ethylene glycol, propylene glycol, glycerin, diethylene glycol, ethylene glycol monomethyl ether, ethylene glycol monoethyl ether, ethylene glycol monobutyl ether, propylene glycol monomethyl ether, propylene glycol monoethyl ether, propylene glycol monobutyl ether, diethylene glycol monomethyl ether, diethylene glycol monoethyl ether, diethylene glycol monobutyl ether, acetone, methyl ethyl ketone, tetrahydrofuran, and dioxane, those freely miscible with water, such as acetonitrile, dimethylformamide, dimethylacetamide, dimethyl sulfoxide, formic acid, acetic acid, propionic acid, triethylamine, and pyridine.

In the practice of the present invention, two or more kinds selected therefrom may be used in combination.

(Surface Treatment Solution Containing Azole Silane Compound of Chemical Formula (IV-1))

The surface treatment solution of the second group according to the present invention (hereinafter, also simply referred to as a surface treatment solution according to the present invention) contains the azole silane compound represented by chemical formula (IV-1) (hereinafter, also referred to as azole silane compound (IV-1)) as a silane coupling agent.

The azole silane compound encompasses:

the azole silane compound (II-1) where $Z_2$ is —CO—NH—$(CH_2)_m$—$Si(OR)_3$ in chemical formula (IV-1);

an azole silane compound of the case of —CO—NH—$(CH_2)_m$—$Si(OR)_2(OH)$ (hereinafter, referred to as azole silane compound (IV-1a));

an azole silane compound of the case of —CO—NH—$(CH_2)_m$—$Si(OR)(OH)_2$ (hereinafter, referred to as azole silane compound (IV-1b)), and an azole silane compound of the case of —CO—NH—$(CH_2)_m$—$Si(OH)_3$ (hereinafter, referred to as azole silane compound (IV-1c)).

That is, the azole silane compound (II-1) is an azole silane compound where n is 0 in chemical formula (IV-1).

Similarly, the azole silane compound (IV-1a) is an azole silane compound where n is 1; the azole silane compound (IV-1b) is an azole silane compound where n is 2; and the azole silane compound (IV-1c) is an azole silane compound where n is 3.

The azole silane compounds (IV-1a) to (IV-1c) are species generated by hydrolysis of the azole silane compound (II-1) present in the surface treatment solution, and they are suitable for the component of silane coupling agent as well as the azole silane compound (II-1) which is a trialkoxy body. The azole silane compounds (IV-1a) to (IV-1c) can be used by extracting from the surface treatment solution by, for example, removing the volatile content from the surface treatment solution.

In the practice of the present invention, it is preferred to use the azole silane compound (II-1) as a raw material for preparing the surface treatment solution.

Examples of the azole silane compound (II-1) are same as those described above.

The surface treatment solution of the second group according to the present invention is prepared in the same manner as in the surface treatment solution of the first group except for using the azole silane compound (II-1) in place of the azole silane compound (I-1).

(Hydrolysis of Azole Silane Compound)

The azole silane compounds (I-1) and (II-1) according to the present invention are hydrolyzed upon contact with water, as described above, and an embodiment of the hydrolysis is shown in scheme (C).

The scheme (C) indicates an embodiment where the silyl group included in the azole silane compounds (I-1), (III-1a) and (III-1b) and the azole silane compounds (II-1), (IV-1a) and (IV-1b) is hydrolyzed, that is, an embodiment where the trialkoxysilyl group is progressively changed to a dialkoxyhydroxysilyl group, a dihydroxyalkoxysilyl group, and trihydroxysilyl group.

Scheme (C)

[Chem. 24]

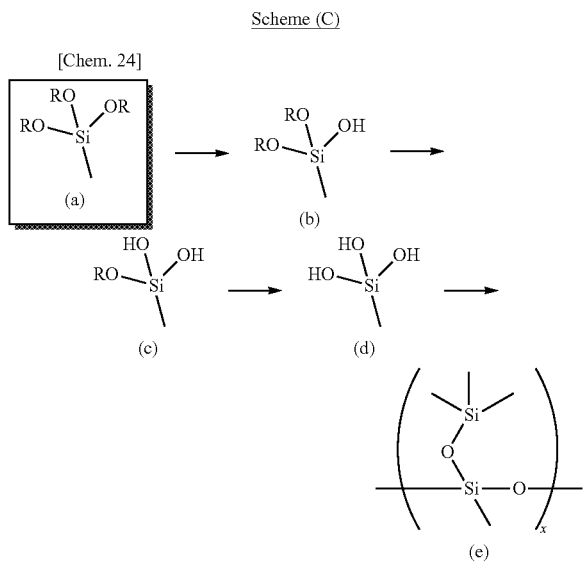

In general, it is known that a substance having an alkoxysilyl group in its molecule acts as a silane coupling agent.

For instance, to cite the bonding between copper and a resin material as an example, the azole silane compound used in the practice of the present invention has an azole ring and an alkoxysilyl group (—Si—OR) in the molecule thereof and the azole ring interacts with the resin and copper to form a chemical bond.

Also, the alkoxysilyl group is subjected to hydrolysis to be converted to a hydroxysilyl group (—Si—OH) and the hydroxysilyl group chemically bonds to copper oxide dotting on the surface of copper.

Therefore, by bringing the surface treatment solution into contact with copper, a chemical film derived from the azole silane compound represented by chemical formula (III-1) or (IV-1) is formed due to the bonds of the azole ring and hydroxysilyl group on the surface of the copper, and in the case of forming a resin layer composed of a resin material on the surface of the chemical film, the bonding property between the copper and the resin material can be enhanced in comparison with the case of directly forming the rein layer on the surface of copper.

In the practice of the present invention, the concentration of at least one compound selected from the azole silane compounds represented by chemical formulae (III-1) and (IV-1) in the surface treatment solution is preferably from 0.001 to 10% by weight, and more preferably from 0.01 to 5% by weight, calculated in terms of the concentration of the azole silane compounds (I-1) and (II-1) which are trialkoxy bodies.

In the case where the concentration is less than 0.001% by weight, the effect of improving the bonding property is not sufficient, whereas in the case where the concentration exceeds 10% by weight, the effect of improving the bonding property becomes almost plateau and it is not economical to further increase the amount of the azole silane compound used.

By the way, the azole silane compounds (III-1a) to (III-1c) and (IV-1a) to (IV-1c) having a hydroxysilyl group generated in the surface treatment solution gradually react with each other to perform dehydration condensation, and the hydroxysilyl group forms a siloxane bond (Si—O—Si) (see the scheme (C)) thereby being converted to a hardly water-soluble silane oligomer (azole silane compound having a group represented by chemical formula (e) in the scheme (C)). x of the group represented by chemical formula (e) is an integer denoting a number of the repeating units.

When the amount of silane oligomer produced in the surface treatment solution becomes large, the insoluble matter precipitates (the treating solution becomes white turbid) and may attach to a treatment tank, pipes connected to the treatment tank, and sensors for detecting the temperature and the liquid level of the treatment solution, which are immersed in the treatment solution, so that there is a possibility to inhibit smooth surface treatment.

In order to avoid this, in the case of using water in the preparation of the surface treatment solution, it is preferred to incorporate an organic solvent into the surface treatment solution, as a dissolving agent for the hardly water-soluble silane oligomer.

The content of the organic solvent is preferably a ratio of from 0.1 to 90 parts by weight, and more preferably a ratio of from 1 to 50 parts by weight, based on 100 parts by weight of water.

In the preparation of the surface treatment solution according to the present invention, an acid such as acetic acid or hydrochloric acid or an alkali such as sodium hydroxide or ammonia may be used in order to accelerate the hydrolysis of the azole silane compounds (I-1) and (II-1).

Similarly, a substance generating a halide ion such as chloride ion, bromide ion or iodide ion or a metal ion such as a copper ion, an iron ion or zinc ion may be used in order to improve the stability of the surface treatment solution and the uniformity of the chemical film.

Also, a known coupling agent may be used in combination as long as the effect of the present invention is not impaired. Examples of the known coupling agent include a silane coupling agent having a thiol group (mercapto group), a vinyl group, an epoxy group, a (meth)acrylic group, an amino group, or a chloropropyl group.

Examples of such a silane coupling agent include:
mercaptosilane compounds such as
3-mercaptopropyltrimethoxysilane and
3-mercaptopropylmethyldimethoxysilane;
vinylsilane compounds such as
vinyltrichlorosilane,
vinyltrimethoxysilane and
vinyltriethoxysilane;
styrylsilane compounds such as
p-styryltrimethoxysilane;
epoxysilane compounds such as
2-(3,4-epoxycyclohexyl)ethyltrimethoxysilane,
3-glycidoxypropyltrimethoxysilane,
3-glycidoxypropylmethyldiethoxysilane, and
3-glycidoxypropyltriethoxysilane;
acryloxysilane compounds such as
3-acryloxypropyltrimethoxysilane;
methacryloxysilane compounds such as
methacryloxypropylmethyldimethoxysilane,
methacryloxypropyltrimethoxysilane,
methacryloxypropylmethyldiethoxysilane, and
methacryloxypropyltriethoxysilane;
aminosilane compounds such as
N-2-(aminoethyl)-3-aminopropylmethyldimethoxysilane,
N-2-(aminoethyl)-3-aminopropyltrimethoxysilane,
N-2-(aminoethyl)-3-aminopropyltriethoxysilane,
3-aminopropyltrimethoxysilane,
3-aminopropyltriethoxysilane,
3-triethoxysilyl-N-(1,3-dimethyl-butylidene)propylamine,
N-phenyl-3-aminopropyltrimethoxysilane, and N-(vinylbenzyl)-2-aminoethyl-3-aminopropyltrimethoxysilane;
ureidosilane compounds such as 3-ureidopropyltriethoxysilane;
chloropropylsilane compounds such as 3-chloropropyltrimethoxysilane;
sulfidesilane compounds such as bis(triethoxysilylpropyl)tetrasulfide; and
isocyanatosilane compounds such as 3-isocyanatopropyltriethoxysilane.

In addition, aluminum coupling agents, titanium coupling agents, zirconium coupling agents, and the like can also be exemplified.

(Treatment Method)

The method for bringing the surface treatment solution according to the present invention into contact with a surface of the base material is not particularly limited, and a means such as spraying, immersion or coating can be adopted in the same manner as in the case of the silane coupling agent described above.

The time (treatment time) for contacting the surface treatment solution with the base material is preferably from one second to 10 minutes and more preferably from 5 seconds to 3 minutes. In the case where the treatment time is less than one second, a film thickness of the chemical film formed on the surface of base material is thin and the adherence force between the materials different in the quality of material cannot be sufficiently obtained, whereas even when it makes longer than 10 minutes, no significant difference in the film thickness of the chemical film is observed and also the improvement in the bonding property cannot be expected.

Also, the temperature of the surface treatment solution when bringing the surface treatment solution into contact with the surface of a base material is preferably from 5 to 50° C., and it can be appropriately determined according to the relation with the treatment time described above.

After bringing the surface treatment solution according to the present invention into contact with the base material, drying may be performed after washing with water or drying may be performed without washing with water.

The drying is preferably performed at a temperature of from room temperature to 150° C.

The water used for the washing with water is preferably pure water such as ion-exchanged water or distilled water, but the method and time for the washing with water are not particularly limited and it may be performed by means of spraying, immersion or the like, for an appropriate time.

Prior to bringing the surface treatment solution according to the present invention into contact with a surface of copper or a copper alloy, an aqueous solution containing a copper ion may be brought into contact with the surface of copper or a copper alloy. The copper ion source in the aqueous solution containing a copper ion is not particularly limited as long as it is a copper salt dissolved in water, and examples thereof include copper salts such as copper sulfate, copper nitrate, copper chloride, copper formate, and copper acetate. In order to solubilize the copper salt in water, ammonia, hydrochloric acid or the like may be added.

After bringing the surface treatment solution according to the present invention into contact with the surface of copper or a copper alloy, an aqueous acidic or alkaline solution may be brought into contact with the surface of copper or a copper alloy. The aqueous acidic solution and the aqueous alkaline solution are not particularly limited. Examples of the aqueous acidic solution include an aqueous solution containing a mineral acid such as sulfuric acid, nitric acid or hydrochloric acid, or an aqueous solution containing an organic acid such as formic acid, acetic acid, lactic acid, glycolic acid, or an amino acid. Examples of the aqueous alkaline solution include an aqueous solution containing an alkali metal hydroxide such as sodium hydroxide or potassium hydroxide, or an amine such as ammonia, ethanolamine or monopropanolamine.

The surface treatment solution according to the present invention can be used for treating a surface of at least one base material selected from the group consisting of the metal, inorganic material and resin material described above. By treating the surface of the base material by using the surface treatment solution according to the present invention, a chemical film is formed on the surface of the base material so that the bonding property to other materials can be enhanced.

According to the present invention, two materials selected from the group consisting of the metal, inorganic material and resin material described above can be bonded by using the surface treatment solution according to the present invention. By bonding two materials through a layer of the chemical film formed by the surface treatment solution according to the present invention, since the mutual affinity can be enhanced, even materials different in the quality of material can be more firmly bonded.

(Bonding Method)

As to the bonding method, it can be conducted by a known method. Examples thereof include a method in which the surface treatment solution according to the present invention is brought into contact with a surface of base material composed of metal, an inorganic material or a resin material to form a chemical film, and another base material is bonded to a part or all of the formed chemical film by using means such as coating, pressure bonding or mixing, by utilizing an adhesive or an adhesive sheet (film), or by a combination thereof.

Also, there may be mentioned a method in which the surface treatment solution according to the present invention is brought into contact with surfaces of two base materials selected from the metal, inorganic material and resin material to form a chemical film on each of the surfaces of the two base materials, and the two base materials are bonded by using means such as coating, pressure bonding or mixing, by utilizing an adhesive or an adhesive sheet (film), or by a combination thereof.

By using the surface treatment solution according to the present invention, two materials, in particular, two materials different in the quality of material, can be bonded, so that it can be suitably utilized in various electric or electronic components or an electronic device such as a printed wiring board.

In the present invention, the surface treatment solution according to the present invention can be suitably used to a base material formed of metal, particularly, of copper or a copper alloy. For example, it is suitable for surface treatment of cupper or a copper ally for the purpose of enhancing bonding property (adhesion property) between a copper circuit (copper wiring layer) and a prepreg or a solder resist (insulating resin layer), and the bonding property between the copper wiring layer and the insulating resin layer can be enhanced in the printed wiring board having the insulating resin layer in contact with the copper wiring layer.

The printed wiring board can be produced by bringing the surface treatment solution according to the present invention into contact with a surface of the copper wiring, followed by washing with water and drying, and then forming an insulating resin layer on the surface of the copper wiring. The contact method is the same as that described above, and immersion of the copper wiring in the surface treatment solution, spraying of the treatment solution to the copper wiring or the like is preferred because of simplicity and certainty.

Also, the method for washing with water is not particularly limited, and immersion of the copper wiring in washing water or spraying of washing water to the copper wiring is preferred because of simplicity and certainty.

For the formation of the insulating resin layer, a known method, for example, a method of sticking a semi-cured resin material or a means of coating a liquid resin material containing a solvent can be utilized. Subsequently, a via hole is formed in order to conduct the upper and lower wiring. By repeating the process, a multilayer printed wiring board can be produced.

The copper wiring may be one produced by any method such as an electroless plating method, an electrolytic plating method, an evaporation method, a sputtering method, or a damascene method, and may contain an inner via hole, a through hole, a connection terminal or the like.

The "copper" according to the present invention is one used in the use and form, such as a foil (electrolytic copper foil or rolled copper foil), a plating film (electroless copper plating film or electrolytic copper plating film), a wire, a rod, a tube, or a plate, which are used in electronic devices such as a printed wiring board and a lead frame, an ornament or a building material. In the case of a recent copper wiring through which a high frequency electric signal flows, it is preferred that the surface of copper is a smooth surface having an average roughness of 0.1 µm or less.

(Insulating composition)

Each of the azole silane compounds (III-1) and (IV-1) according to the present invention can form an insulating composition by incorporating it into a rein material or an inorganic material as a silane coupling agent.

Also, an insulating composition can be obtained by dissolving each of the azole silane compounds (III-1) and (IV-1) according to the present invention in an organic solvent or the like and mixing it with a rein material or an inorganic material.

The content of the azole silane compound according to the present invention in the insulating composition is preferably from 0.001 to 10% by weight, and more preferably from 0.01 to 5% by weight. In the case where the content of the azole silane compound according to the present invention is less than 0.001% by weight in the insulating composition, the effect of improving the bonding property is not sufficient, whereas in the case where the concentration exceeds 10% by weight, the effect of improving the bonding property becomes almost plateau and it is not economical to further increase the amount of the azole silane compound used.

The insulating composition can be produced by a known method. For example, the insulating composition can be produced by dissolving the azole silane compound according to the present invention in an organic solvent and mixing it with a solid or liquid resin material. Also, the azole silane compound according to the present invention may be directly added to and mixed with a liquid resin material to produce the insulating composition.

The insulating composition according to the present invention provides an insulating material having high strength so that it can be suitably used in various electric or electronic components or an electronic device such as a printed wiring board.

By the way, JP-A-2009-19266 discloses an invention relating to a method for forming a film of silane coupling agent, containing a step of coating a liquid containing a silane coupling agent on a metal surface, a step of drying the metal surface coated with the liquid at a temperature from 25 to 150° C. for 5 minutes or shorter time, and a step of washing with water the metal surface dried.

Also, it is described that on the metal surface, an adhesive metal layer, such as tin, may be previously formed with an immersion plating solution, as a surface treatment.

The surface treatment solution according to the present invention can be used as the liquid containing a silane coupling agent described above. The matters described in the patent publication are incorporated by reference into the specification.

EXAMPLE

The present invention will be described specifically with reference to the examples and comparative examples, but the present invention should not be construed as being limited thereto.

(Synthesis Tests of the First Group: Azole Silane Compound Represented by Chemical Formula (I-1))

Azole compounds and halogenated alkylsilane compounds used in the synthesis tests are as follows.

(Azole Compound)

3-Mercapto-1,2,4-triazole: product of Tokyo Kasei Kogyo Co., Ltd.

3-Amino-5-mercapto-1,2,4-triazole: Same as above

5-Methyl-1,3,4-thiadiazole-2-thiol: Same as above

5-Methyl-2-mercapto-1,3,4-thiadiazole: Same as above

2-Amino-5-mercapto-1,3,4-thiadiazole: Same as above 2,5-Dimercapto-1,3,4-thiadiazole: Same as above 2-Mercapto-5-methylthio-1,3,4-thiadiazole: Same as above (Halogenated Alkylsilane Compound)

3-Iodopropyltrimethoxysilane: product of Sigma-Aldrich Co.

3-Chloropropyltriethoxysilane: Shin-Etsu Chemical Co., Ltd.

6-Bromohexyltrimethoxysilane: synthesized according to the method described in "D. Zhang et al., Tetrahedron 2007, 63 (23), pp. 5076-5082".

5-Bromopentyltrimethoxysilane: Same as above

8-Bromooctyltrimethoxysilane: Same as above

Example 1-1

Synthesis of 3-[3-(trimethoxysilyl)propylthio]-1,2,4-triazole

A suspension composed of 3.0 g (30 mmol) of 3-mercapto-1,2,4-triazole and 50 ml of dehydrated methanol was cooled to 10° C., thereto was added 5.8 g (30 mmol) of a 28% sodium methoxide methanol solution to form an uniform solution, followed by returning to room temperature and stirring for 30 minutes, and thereto was added dropwise a solution composed of 8.7 g (30 mmol) of 3-iodopropyltrimethoxysilane and 10 ml of dehydrated methanol at room temperature over a period of 10 minutes, followed by further stirring at from 27 to 30° C. for 3 hours and 30 minutes.

The reaction solution was concentrated under a reduced pressure, and 12.5 g of the resulting white viscous substance was extracted three times with 40 ml of diethyl ether, and the extract was filtered and concentrated under a reduced pressure to obtain 7.3 g (27 mmol, yield of 92.3%) of a slightly yellow-brown colored oily substance.

The $^1$H-NMR spectral data of the oily substance obtained were as follows.

$^1$H-NMR (DMSO-d$_6$) δ: 11.94 (br. s, 1H), 8.21 (s, 1H), 3.56 (s, 9H), 3.16 (t, 2H), 1.85 (m, 2H), 0.80 (t, 2H).

The IR spectral data of the oily substance were as shown in the chart shown in FIG. 1.

From these spectral data, the oily substance obtained was identified as the desired azole silane compound represented by chemical formula (1-1).

[Chem. 25]

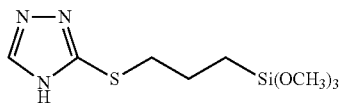

(1-1)

Example 1-2

Synthesis of 3-[3-(triethoxysilyl)propylthio]-1,2,4-triazole

A suspension composed of 3.0 g (30 mmol) of 3-mercapto-1,2,4-triazole and 50 ml of dehydrated ethanol was cooled to 10° C., thereto was added 10.2 g (30 mmol) of a 20% sodium ethoxide ethanol solution to form an uniform solution, followed by returning to room temperature and stirring for 30 minutes, and thereto was added dropwise a solution composed of 6.74 g (30 mmol) of 3-chloropropyltriethoxysilane and 10 ml of dehydrated ethanol at room temperature over a period of 10 minutes, followed by further stirring at 78° C. for 6 hours.

The reaction solution was concentrated under a reduced pressure, and 10.8 g of the resulting white viscous substance was extracted three times with 40 ml of diethyl ether, and the extract was filtered and concentrated under a reduced pressure to obtain 7.8 g (25 mmol, yield of 85.7%) of a slightly yellow-brown colored oily substance.

The $^1$H-NMR spectral data of the oily substance obtained were as follows.

$^1$H-NMR (CDCl$_3$) δ: 10.34 (br. s, 1H), 8.10 (s, 1H), 3.83 (q, 6H), 3.17 (t, 2H), 1.86 (m, 2H), 1.22 (t, 9H), 0.80 (t, 2H).

Figure 2:
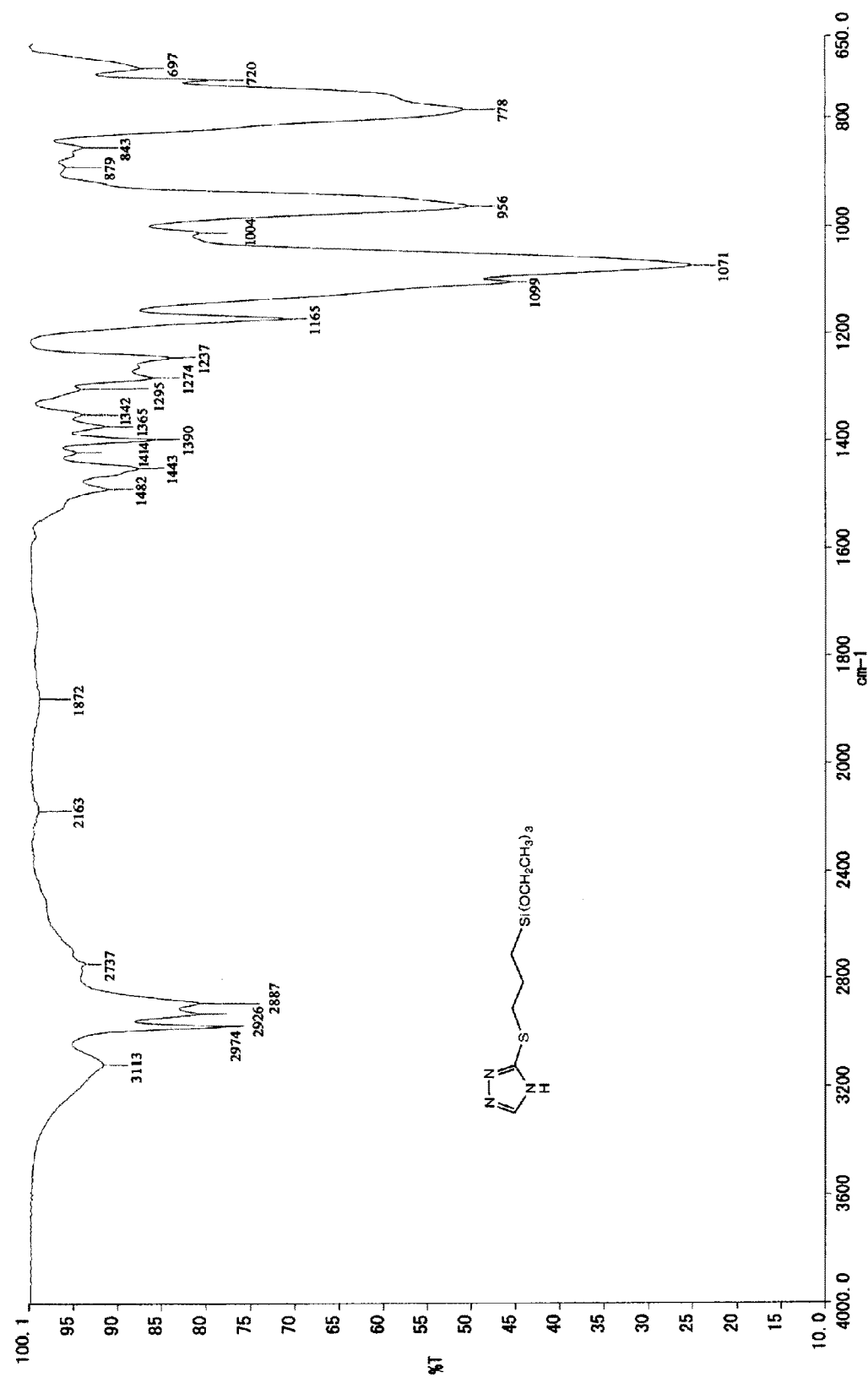
FIG. 2 is an IR spectral chart of the oily material obtained in Example 1-2.

The IR spectral data of the oily substance were as shown in the chart shown in FIG. 2.

From these spectral data, the oily substance obtained was identified as the desired azole silane compound represented by chemical formula (1-2).

[Chem. 26]

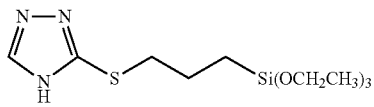

(1-2)

Example 1-3

Synthesis of 3-amino-5-[3-(trimethoxysilyl)propylthio]-1,2,4-triazole

A suspension composed of 6.96 g (60 mmol) of 3-amino-5-mercapto-1,2,4-triazole and 100 ml of dehydrated methanol was cooled to 10° C., thereto was added 3.24 g (60 mmol) of sodium methoxide (solid) to form an uniform solution, followed by returning to room temperature and stirring for 30 minutes, and thereto was added dropwise a solution composed of 17.42 g (60 mmol) of 3-iodopropyltrimethoxysilane and 20 ml of dehydrated methanol at room temperature over a period of 30 minutes, followed by further stirring at from 27 to 30° C. for 3 hours and 30 minutes.

The reaction solution was concentrated under a reduced pressure, and 26.4 g of the resulting white viscous substance was extracted three times with 100 ml of diethyl ether, and the extract was filtered and concentrated under a reduced pressure to obtain 9.20 g (33 mmol, yield of 55.1%) of a slightly yellow-brown colored oily substance.

The $^1$H-NMR spectral data of the oily substance obtained were as follows.

$^1$H-NMR (DMSO-d$_6$) δ: 11.85 (br. s, 1H), 6.01 (br. s, 2H), 3.46 (s, 9H), 2.93 (t, 2H), 1.67 (quint, 2H), 0.69 (t, 2H).

Figure 3:
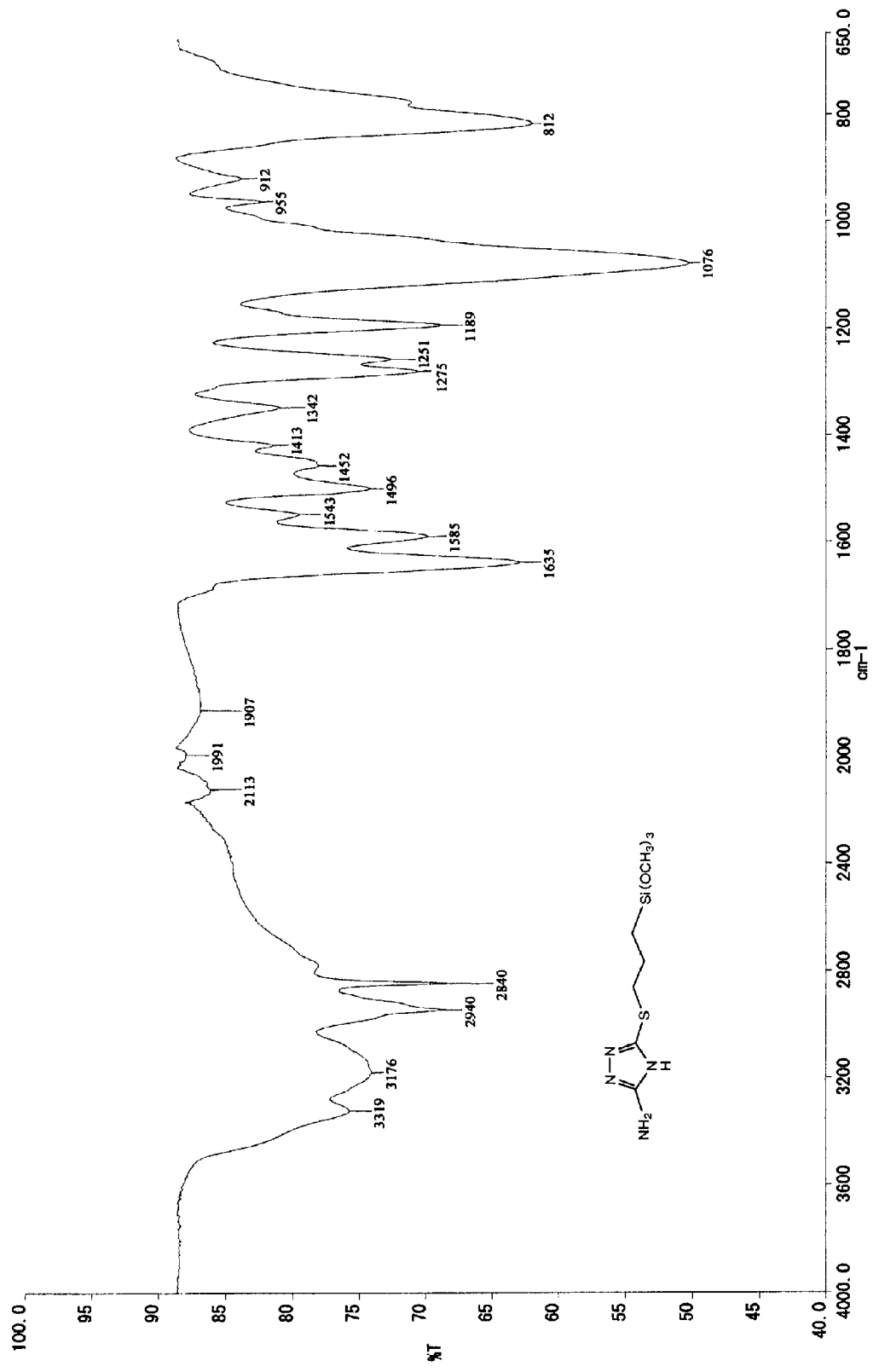
FIG. 3 is an IR spectral chart of the oily material obtained in Example 1-3.

The IR spectral data of the oily substance were as shown in the chart shown in FIG. 3.

From these spectral data, the oily substance obtained was identified as the desired azole silane compound represented by chemical formula (1-3).

[Chem. 27]

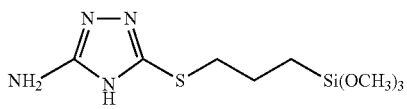

(1-3)

Example 1-4

Synthesis of 3-amino-5-[6-(trimethoxysilyl)hexylthio]-1,2,4-triazole

A suspension composed of 3.48 g (30 mmol) of 3-amino-5-mercapto-1,3,4-triazole and 50 ml of dehydrated methanol was cooled to 10° C., thereto was added 5.8 g (30 mmol) of a 28% sodium methoxide methanol solution to form an uniform solution, followed by returning to room temperature and stirring for 30 minutes, and thereto was added dropwise a solution composed of 9.4 g (30 mmol) of 6-bromohexyltrimethoxysilane and 10 ml of dehydrated methanol at room temperature over a period of 10 minutes, followed by further stirring at 60° C. for 6 hours.

The reaction solution was concentrated under a reduced pressure, and 14.2 g of the resulting white viscous substance was extracted three times with 40 ml of diethyl ether, and the extract was filtered and concentrated under a reduced pressure to obtain 5.3 g (16 mmol, yield of 52%) of a slightly yellow-brown colored oily substance.

The $^1$H-NMR spectral data of the oily substance obtained were as follows.

$^1$H-NMR (DMSO-d$_6$) δ: 5.94 (s, 2H), 3.45 (s, 9H), 2.93 (t, 2H), 1.59 (m, 2H), 1.4-1.2 (m, 6H), 0.57 (m, 2H).

Figure 4:
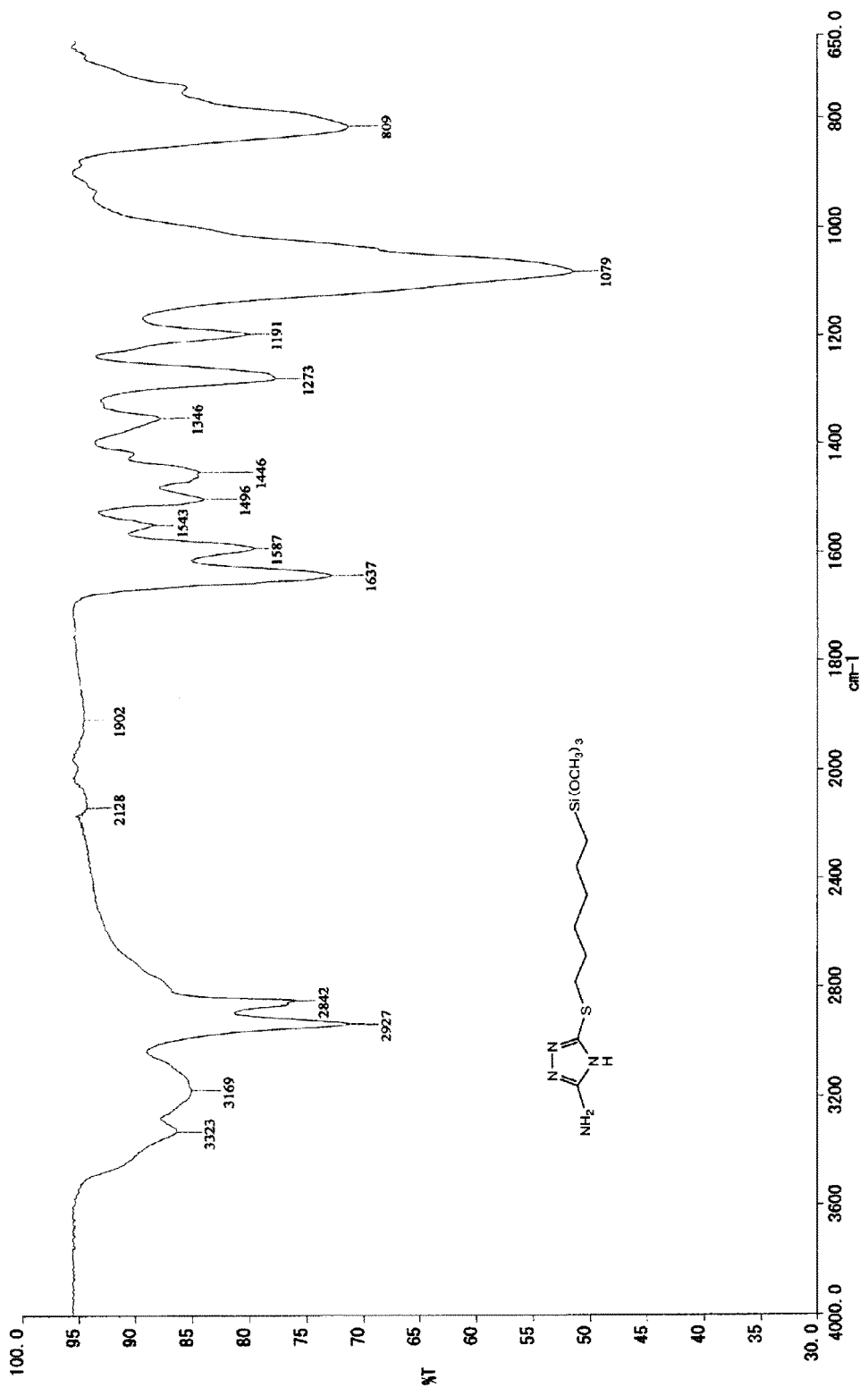
FIG. 4 is an IR spectral chart of the oily material obtained in Example 1-4.

The IR spectral data of the oily substance were as shown in the chart shown in FIG. 4.

From these spectral data, the oily substance obtained was identified as the desired azole silane compound represented by chemical formula (1-4).

[Chem. 28]

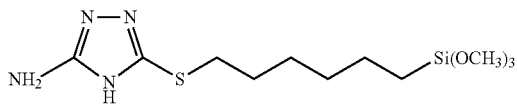

(1-4)

Example 1-5

Synthesis of 3-amino-5-[3-(triethoxysilyl)propyl-thio]-1,2,4-triazole

A suspension composed of 3.48 g (30 mmol) of 3-amino-5-mercapto-1,2,4-triazole and 50 ml of dehydrated ethanol was cooled to 10° C., thereto was added 10.2 g (30 mmol) of a 20% sodium ethoxide ethanol solution to form an uniform solution, followed by returning to room temperature and stirring for 30 minutes, and thereto was added dropwise a solution composed of 6.74 g (30 mmol) of 3-chloropropyltriethoxysilane and 10 ml of dehydrated ethanol at the same temperature over a period of 10 minutes, followed by further stirring at 78° C. for 6 hours.

The reaction solution was concentrated under a reduced pressure, and 10.8 g of the resulting white viscous substance was extracted three times with 40 ml of diethyl ether, and the extract was filtered and concentrated under a reduced pressure to obtain 7.8 g (25 mmol, yield of 85.7%) of slightly yellow-brown colored crystals.

The melting point and $^1$H-NMR spectral data of the crystal obtained were as follows.

Melting point: 56 to 57° C.
$^1$H-NMR (CDCl$_3$) δ: 11.21 (br. s, 1H), 5.06 (s, 2H), 3.81 (q, 6H), 3.06 (t, 2H), 1.81 (m, 2H), 1.21 (t, 9H), 0.77 (t, 2H).

Figure 5:
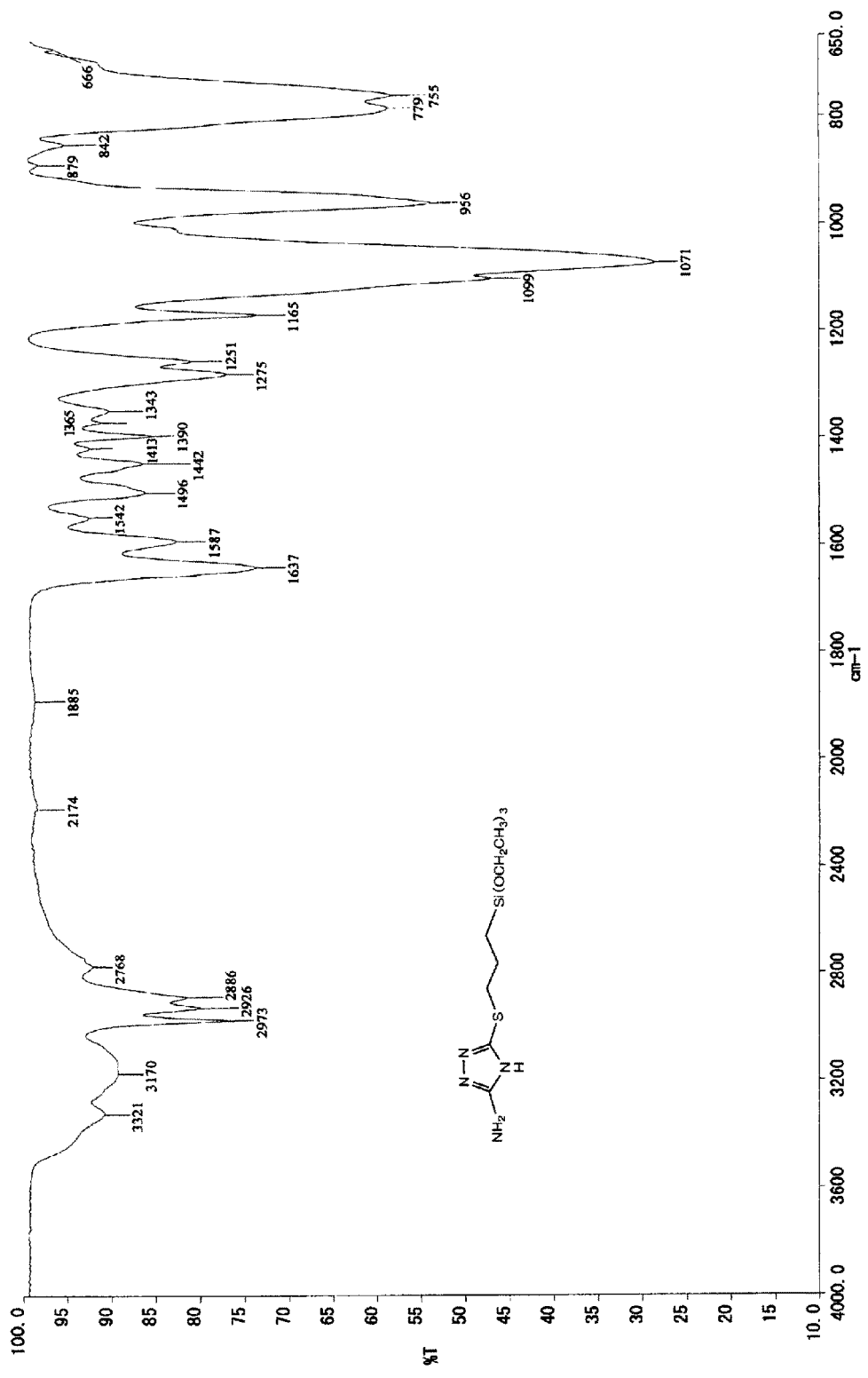
FIG. 5 is an IR spectral chart of the crystal obtained in Example 1-5.

The IR spectral data of the crystal were as shown in the chart shown in FIG. 5.

From these spectral data, the crystal obtained was identified as the desired azole silane compound represented by chemical formula (1-5).

[Chem. 29]

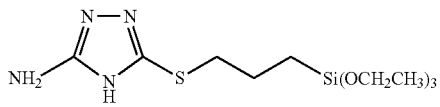

(1-5)

Example 1-6

Synthesis of 5-methyl-2-[3-(trimethoxysilyl)propyl-thio]-1,3,4-thiadiazole

A suspension composed of 7.9 g (60 mmol) of 5-methyl-1,3,4-thiadiazole-2-thiol and 100 ml of dehydrated methanol was cooled to 10° C., thereto was added 11.6 g (60 mmol) of a 28% sodium methoxide methanol solution to form an uniform solution, followed by returning to room temperature and stirring for 30 minutes, and thereto was added dropwise a solution composed of 17.4 g (60 mmol) of 3-iodopropyltrimethoxysilane and 20 ml of dehydrated methanol at room temperature over a period of 30 minutes, followed by further stirring at from 34 to 40° C. for 4 hours.

The reaction solution was concentrated under a reduced pressure, and 26.5 g of the resulting white viscous substance was extracted three times with 80 ml of diethyl ether, and the extract was filtered and concentrated under a reduced pressure to obtain 16.9 g (60 mmol, yield of 99.9%) of a slightly yellow-brown colored oily substance.

The $^1$H-NMR spectral data of the oily substance obtained were as follows.

$^1$H-NMR (CDCl$_3$) δ: 3.56 (s, 9H), 3.31 (t, 2H), 2.71 (s, 3H), 1.92 (m, 2H), 0.80 (t, 2H).

Figure 6:
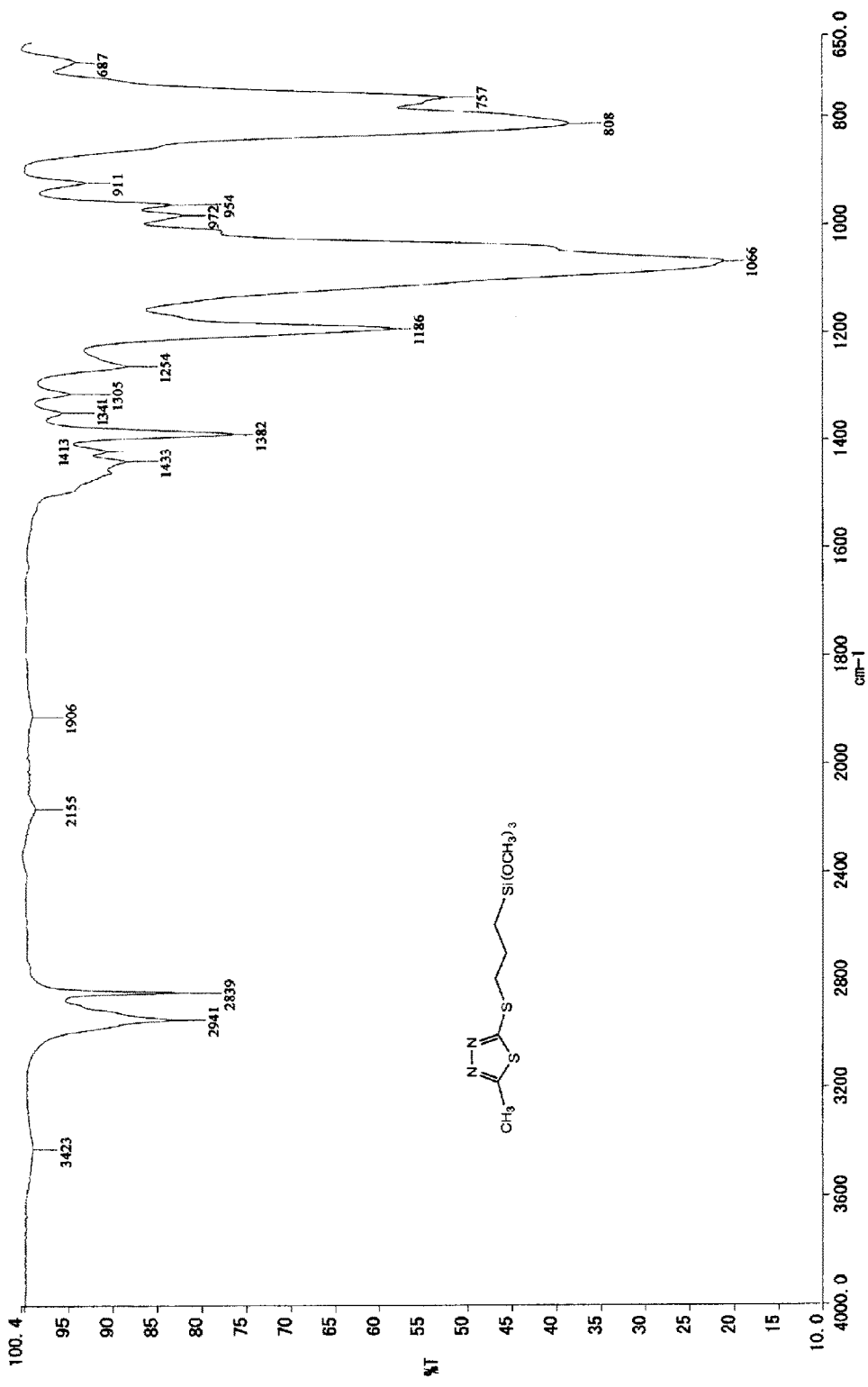
FIG. 6 is an IR spectral chart of the oily material obtained in Example 1-6.

The IR spectral data of the oily substance were as shown in the chart shown in FIG. 6.

From these spectral data, the oily substance obtained was identified as the desired azole silane compound represented by chemical formula (1-6).

[Chem. 30]

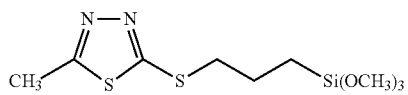

(1-6)

Example 1-7

Synthesis of 5-methyl-2-[5-(trimethoxysilyl)pentyl-thio]-1,3,4-thiadiazole

A suspension composed of 3.3 g (25 mmol) of 2-mercapto-5-methyl-1,3,4-thiadiazole and 40 ml of dehydrated methanol was cooled to 10° C., thereto was added 4.8 g (25 mmol) of a 28% sodium methoxide methanol solution to form an uniform solution, followed by returning to room temperature and stirring for 30 minutes, and thereto was added dropwise a solution composed of 6.8 g (25 mmol) of 5-bromopentyltrimethoxysilane and 10 ml of dehydrated methanol at room temperature over a period of 10 minutes, followed by further stirring at 60° C. for 6 hours.

The reaction solution was concentrated under a reduced pressure, and 10.4 g of the resulting white viscous substance was extracted three times with 40 ml of diethyl ether, and the extract was filtered and concentrated under a reduced pressure to obtain 6.1 g (19 mmol, yield of 75.7%) of a slightly yellow-brown colored oily substance.

The $^1$H-NMR spectral data of the oily substance obtained were as follows.

$^1$H-NMR (DMSO-d$_6$) δ: 3.47 (s, 9H), 3.24 (t, 2H), 2.69 (s, 3H), 1.71 (m, 2H), 1.5-1.3 (m, 4H), 0.60 (t, 2H).

Figure 7:
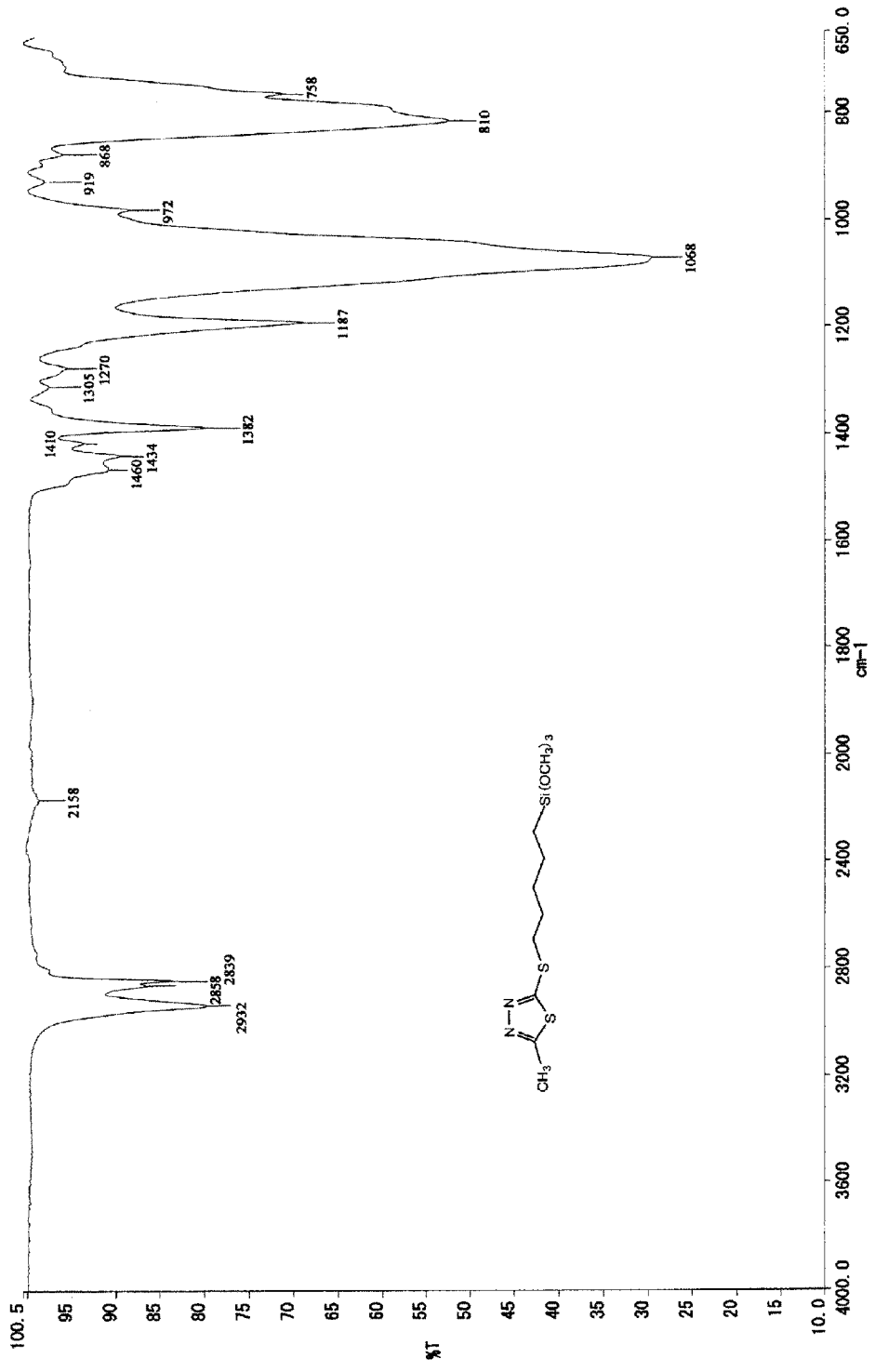
FIG. 7 is an IR spectral chart of the oily material obtained in Example 1-7.

The IR spectral data of the oily substance were as shown in the chart shown in FIG. 7.

From these spectral data, the oily substance obtained was identified as the desired azole silane compound represented by chemical formula (1-7).

[Chem. 31]

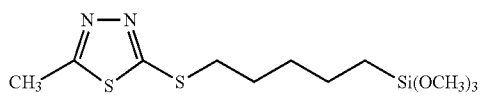

(1-7)

Example 1-8

Synthesis of 2-amino-5-[3-(trimethoxysilyl)propyl-thio]-1,3,4-thiadiszole

To a suspension composed of 8.0 g (60 mmol) of 2-amino-5-mercapto-1,3,4-thiadiazole and 90 ml of dehydrated methanol was added 3.24 g (60 mmol) of sodium methoxide (solid) at room temperature to form an uniform solution, followed by stirring for 30 minutes, and thereto was added dropwise a solution composed of 17.4 g (60 mmol) of 3-iodopropyltrimethoxysilane and 17 ml of dehydrated methanol over a period of 30 minutes, followed by further stirring at from 37 to 40° C. for 5 hours.

The reaction solution was concentrated under a reduced pressure, and to 27.1 g of the resulting white viscous substance was added 100 ml of diethyl ether, followed by stirring, and after removing the insoluble matter by filtration, the filtrate was concentrated under a reduced pressure to obtain 17.5 g (59 mmol, yield of 98.7%) of slightly yellow-brown colored crystals.

The melting point and $^1$H-NMR spectral data of the crystal obtained were as follows.

Melting point: 42° C.
$^1$H-NMR (DMSO-d$_6$) δ: 7.28 (br. s, 2H), 3.47 (s, 9H), 3.03 (t, 2H), 1.69 (quint, 2H), 0.72 (t, 2H).

Figure 8:
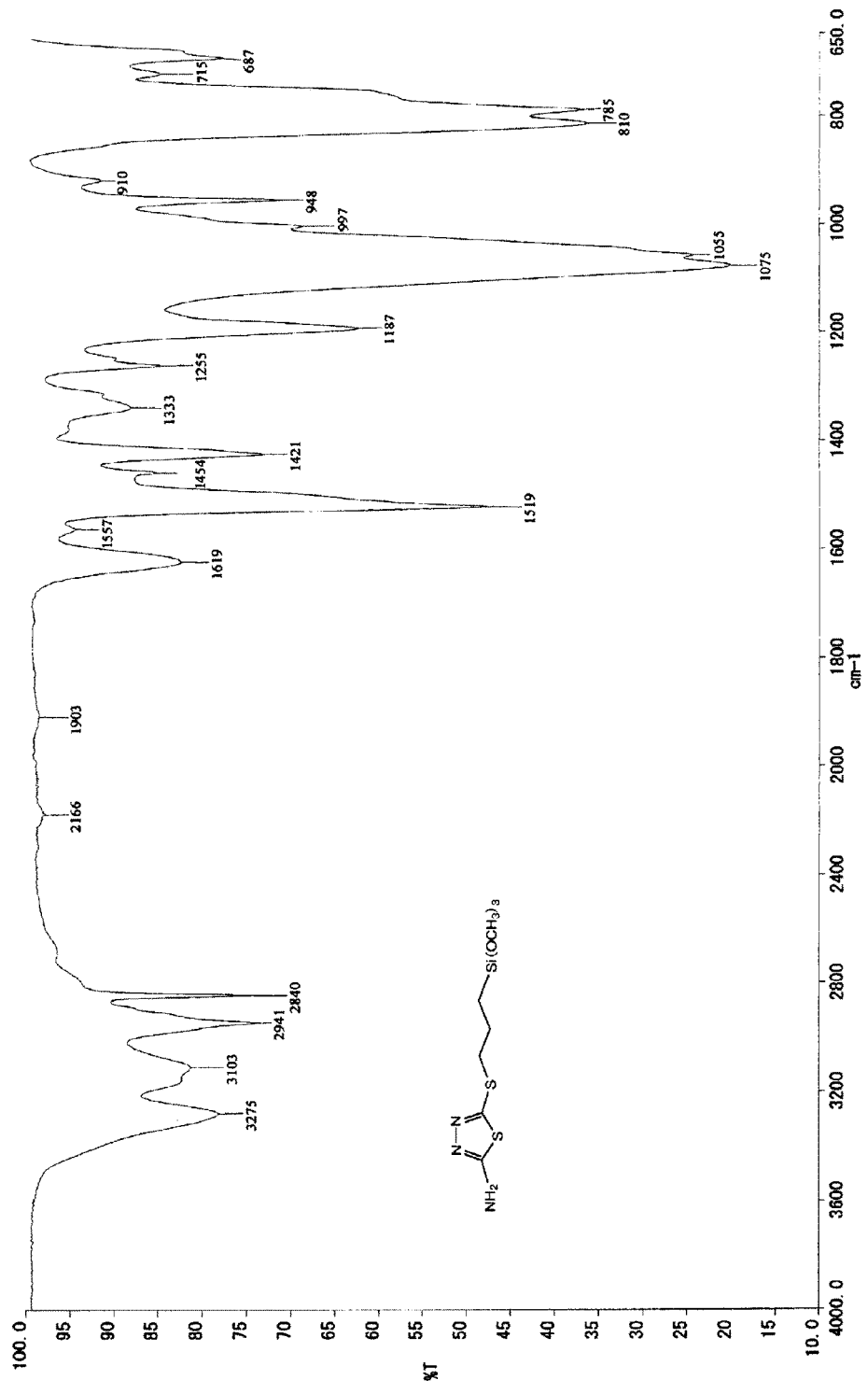
FIG. 8 is an IR spectral chart of the crystal obtained in Example 1-8.

The IR spectral data of the crystal were as shown in the chart shown in FIG. 8.

From these spectral data, the crystal obtained was identified as the desired azole silane compound represented by chemical formula (1-8).

[Chem. 32]

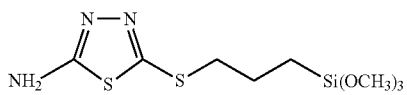

(1-8)

Example 1-9

Synthesis of 2-amino-5-[8-(trimethoxysilyl)octyl-thio]-1,3,4-thiadiazole

A suspension composed of 3.33 g (25 mmol) of 2-amino-5-mercapto-1,3,4-thiadiazole and 40 ml of dehydrated methanol was cooled to 10° C., thereto was added 4.8 g (25 mmol) of a 28% sodium methoxide methanol solution to form an uniform solution, followed by returning to room temperature and stirring for 30 minutes, and thereto was added dropwise a solution composed of 7.80 g (25 mmol) of 8-bromooctyltrimethoxysilane and 10 ml of dehydrated methanol at room temperature over a period of 10 minutes, followed by further stirring at 60° C. for 6 hours.

The reaction solution was concentrated under a reduced pressure, and 11.9 g of the resulting white viscous substance was extracted three times with 40 ml of diethyl ether, and the extract was filtered and concentrated under a reduced pressure to obtain 4.1 g (12 mmol, yield of 45.0%) of a slightly yellow-brown colored oily substance.

The $^1$H-NMR spectral data of the oily substance obtained were as follows.

$^1$H-NMR (DMSO-d$_6$) δ: 7.25 (s, 2H), 3.45 (s, 9H), 3.03 (t, 2H), 1.62 (m, 2H), 1.4-1.2 (m, 10H), 0.57 (t, 2H).

Figure 9:
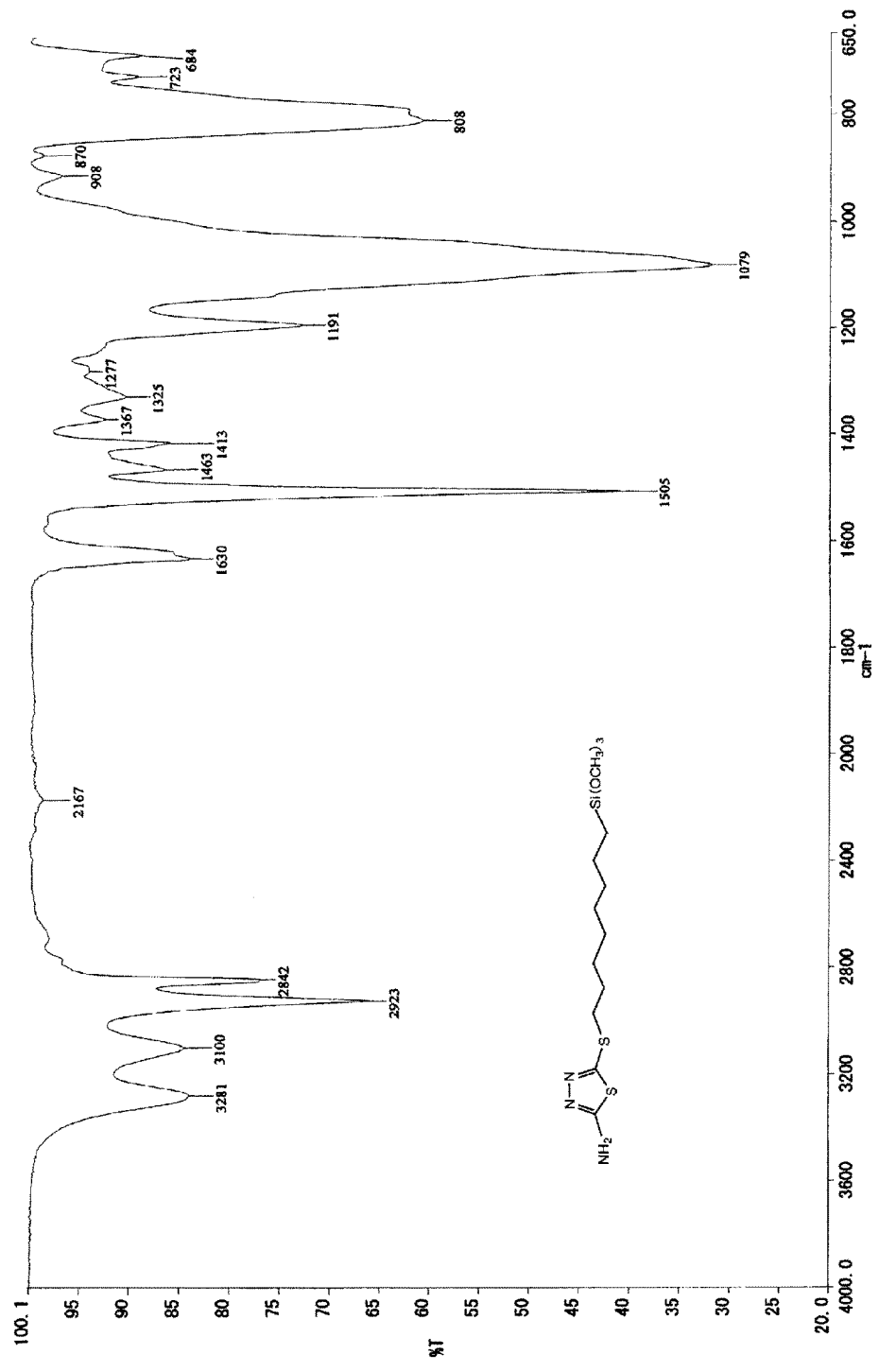
FIG. 9 is an IR spectral chart of the oily material obtained in Example 1-9.

The IR spectral data of the oily substance were as shown in the chart shown in FIG. 9.

From these spectral data, the oily substance obtained was identified as the desired azole silane compound represented by chemical formula (1-9).

[Chem. 33]

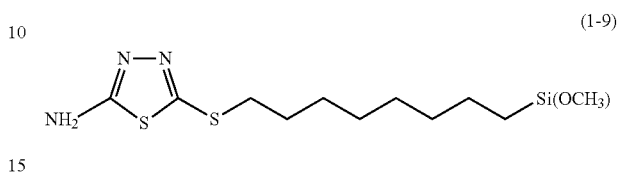

(1-9)

Example 1-10

Synthesis of 2-amino-5-[3-(triethoxysilyl)propyl-thio]-1,3,4-thiadiazole

A suspension composed of 3.99 g (30 mmol) of 2-amino-5-mercapto-1,3,4-thiadiazole and 50 ml of dehydrated ethanol was cooled to 10° C., thereto was added 10.2 g (30 mmol) of a 20% sodium ethoxide ethanol solution to form an uniform solution, followed by returning to room temperature and stirring for 30 minutes, and thereto was added dropwise a solution composed of 6.74 g of (30 mmol) of 3-chloropropyltriethoxysilane and 10 ml of dehydrated ethanol at room temperature over a period of 10 minutes, followed by further stirring at 78° C. for 6 hours.

The reaction solution was concentrated under a reduced pressure, and 11.6 g of the resulting white viscous substance was extracted three times with 40 ml of diethyl ether, and the extract was filtered and concentrated under a reduced pressure to obtain 9.1 g (26 mmol, yield of 89.8%) of slightly yellow-brown colored crystals.

The melting point and $^1$H-NMR spectral data of the crystal obtained were as follows.

Melting point: 66 to 68° C.
$^1$H-NMR (CDCl$_3$) δ: 5.82 (s, 2H), 3.81 (q, 6H), 3.14 (t, 2H), 1.85 (m, 2H), 1.21 (t, 9H), 0.77 (t, 2H).

Figure 10:
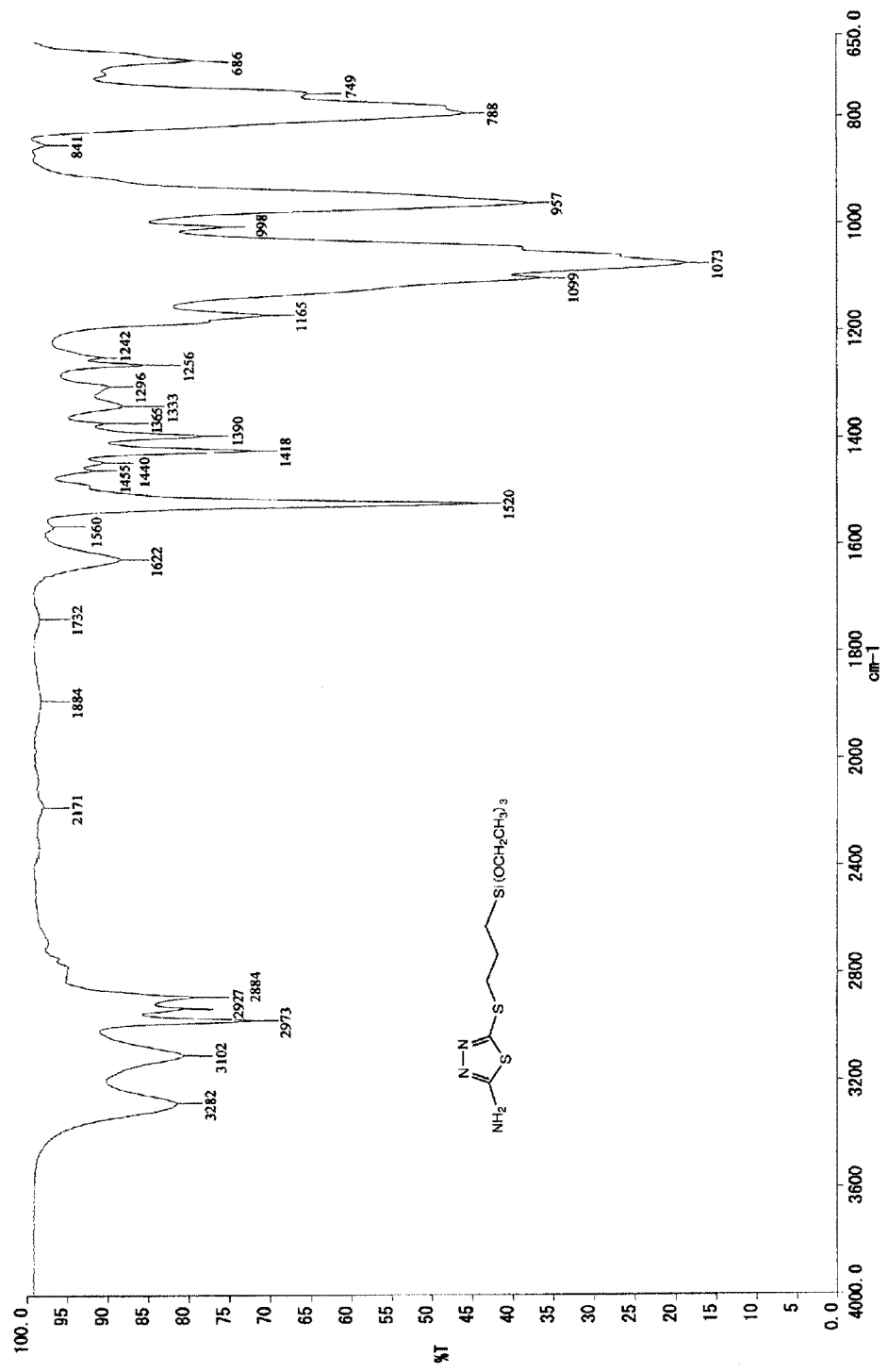
FIG. 10 is an IR spectral chart of the crystal obtained in Example 1-10.

The IR spectral data of the crystal were as shown in the chart shown in FIG. 10.

From these spectral data, the crystal obtained was identified as the desired azole silane compound represented by chemical formula (1-10).

[Chem. 34]

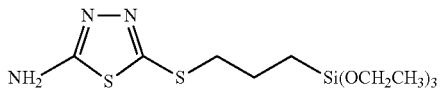

(1-10)

Example 1-11

Synthesis of 2-mercapto-5-[3-(trimethoxysilyl)pro-pylthio]-1,3,4-thiadiazole

To a suspension composed of 9.0 g (60 mmol) of 2,5-dimercapto-1,3,4-thiadiazole and 90 ml of dehydrated methanol was added 3.24 g (60 mmol) of sodium methoxide (solid) at room temperature to form an uniform solution, followed by stirring for 30 minutes, and thereto was added dropwise a solution composed of 17.4 g (60 mmol) of 3-iodopropyltrimethoxysilane and 17 ml of dehydrated methanol at from 15 to 17° C. under cooling with water over a period of 30 minutes, followed by further stirring at from 42 to 44° C. for 4 hours.

The reaction solution was concentrated under a reduced pressure, and to 27.5 g of the resulting white viscous substance was added 100 ml of diethyl ether, followed by stirring, and after removing the insoluble matter by filtration, the filtrate was concentrated under a reduced pressure to obtain 16.7 g (53 mmol, yield of 89.1%) of a pale yellow colored oily substance.

The $^1$H-NMR spectral data of the oily substance obtained were as follows.

$^1$H-NMR (CDCl$_3$) δ: 12.01 (br. s, 1H), 3.58 (s, 9H), 3.15 (t, 2H), 1.87 (quint, 2H), 0.79 (t, 2H).

Figure 11:
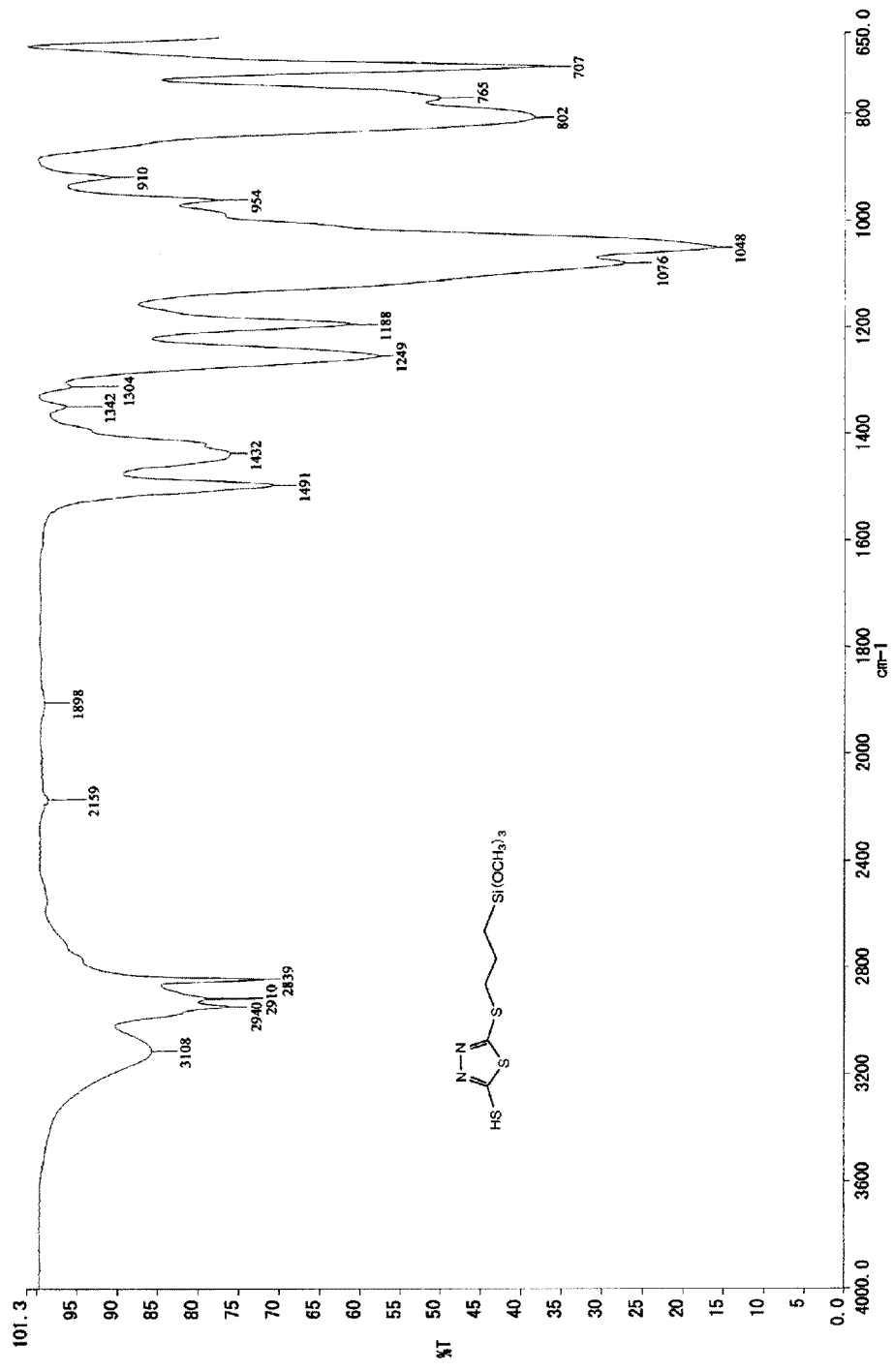
FIG. 11 is an IR spectral chart of the oily material obtained in Example 1-11.

The IR spectral data of the oily substance were as shown in the chart shown in FIG. 11.

From these spectral data, the oily substance obtained was identified as the desired azole silane compound represented by chemical formula (1-11).

[Chem. 35]

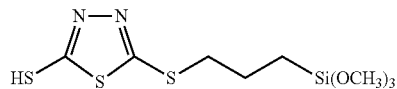

(1-11)

Example 1-12

Synthesis of 2-mercapto-5-[3-(triethoxysilyl)propylthio]-1,3,4-thiadiazole

A suspension composed of 4.50 g (30 mmol) of 2,5-dimercapto-1,3,4-thiadiazole and 50 ml of dehydrated ethanol was cooled to 10° C., thereto was added 10.2 g (30 mmol) of a 20% sodium ethoxide ethanol solution to dissolve them, followed by returning to room temperature and stirring for 30 minutes, and thereto was added dropwise a solution composed of 6.74 g (30 mmol) of 3-chloropropyltriethoxysilane and 10 ml of dehydrated ethanol at room temperature over a period of 10 minutes, followed by further stirring at 78° C. for 6 hours.

The reaction solution was concentrated under a reduced pressure, and 14.8 g of the resulting white viscous substance was extracted three times with 40 ml of diethyl ether, and the extract was filtered and concentrated under a reduced pressure to obtain 9.0 g (25 mmol, yield of 84.6%) of a slightly yellow-brown colored oily substance.

The $^1$H-NMR spectral data of the oily substance obtained were as follows.

$^1$H-NMR (CDCl$_3$) δ: 8.79 (s, 1H), 3.83 (q, 6H), 3.15 (t, 2H), 1.88 (m, 2H), 1.23 (t, 9H), 0.77 (t, 2H).

Figure 12:
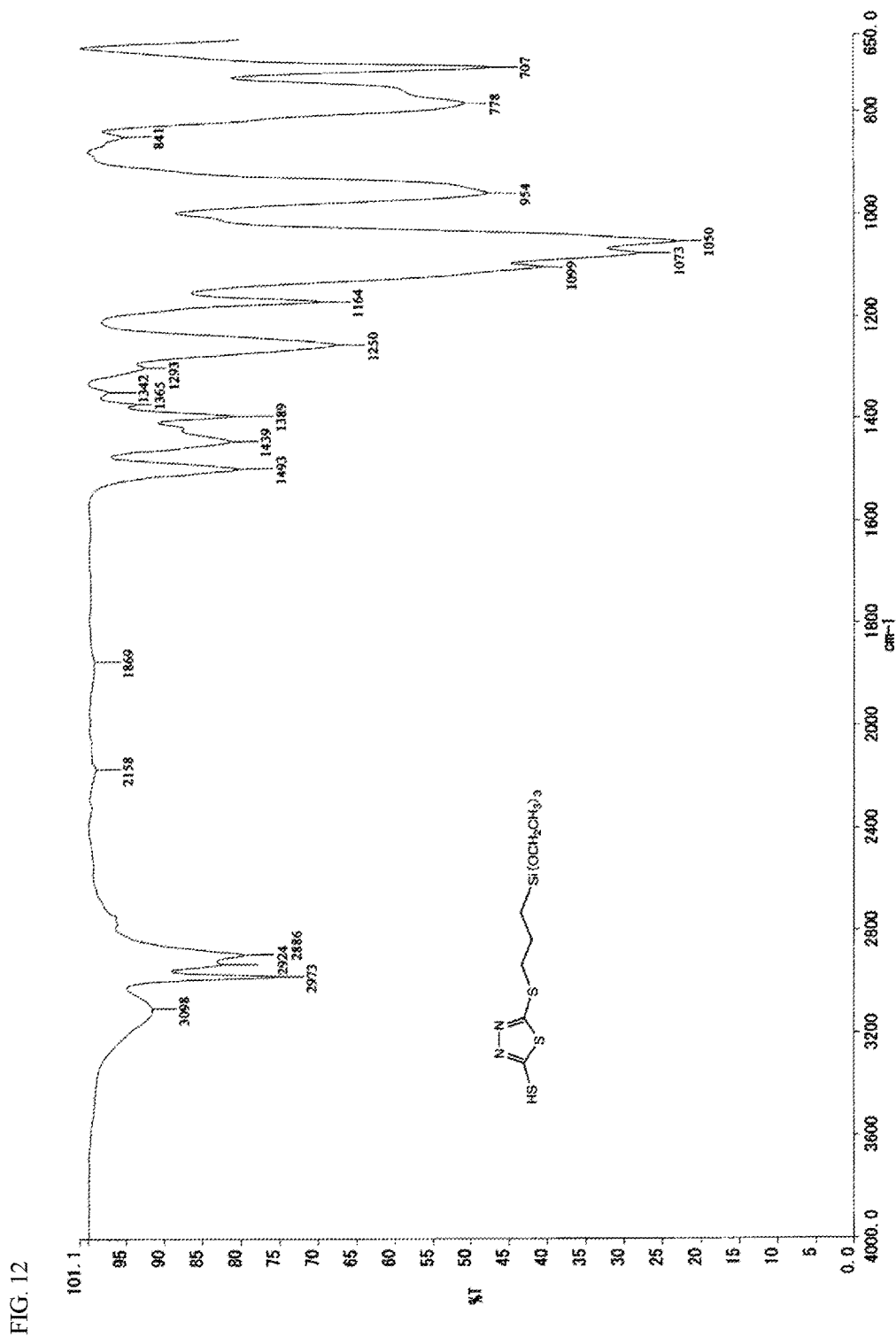
FIG. 12 is an IR spectral chart of the oily material obtained in Example 1-12.

The IR spectral data of the oily substance were as shown in the chart shown in FIG. 12.

From these spectral data, the oily substance obtained was identified as the desired azole silane compound represented by chemical formula (1-12).

[Chem. 36]

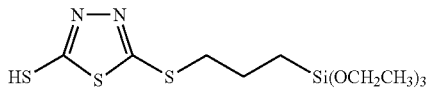

(1-12)

Example 1-13

Synthesis of 2-methylthio-5-[3-(trimethoxysilyl)propylthio]-1,3,4-thiadiazole

To a suspension composed of 11.4 g (69.4 mmol) of 2-mercapto-5-methylthio-1,3,4-thiadiazole and 120 ml of dehydrated methanol was added 3.75 g (69.4 mmol) of sodium methoxide (solid) at room temperature to form an uniform solution, followed by stirring for 30 minutes, and thereto was added dropwise a solution composed of 20.1 g (69.3 mmol) of 3-iodopropyltrimethoxysilane and 20 ml of dehydrated methanol over a period of 30 minutes, followed by further stirring at from 34 to 37° C. for 5 hours.

The reaction solution was concentrated under a reduced pressure, to 32.6 g of the resulting white viscous substance was added 130 ml of diethyl ether, followed by stirring, and after removing the insoluble matter by filtration, the filtrate was concentrated under a reduced pressure to obtain 22.5 g (68.9 mmol, yield of 99.3%) of a pale yellow colored oily substance.

The $^1$H-NMR spectral data of the oily substance obtained were as follows.

$^1$H-NMR (CDCl$_3$) δ: 3.57 (s, 9H), 3.30 (t, 2H), 2.76 (s, 3H), 1.91 (quint, 2H), 0.80 (t, 2H).

Figure 13:
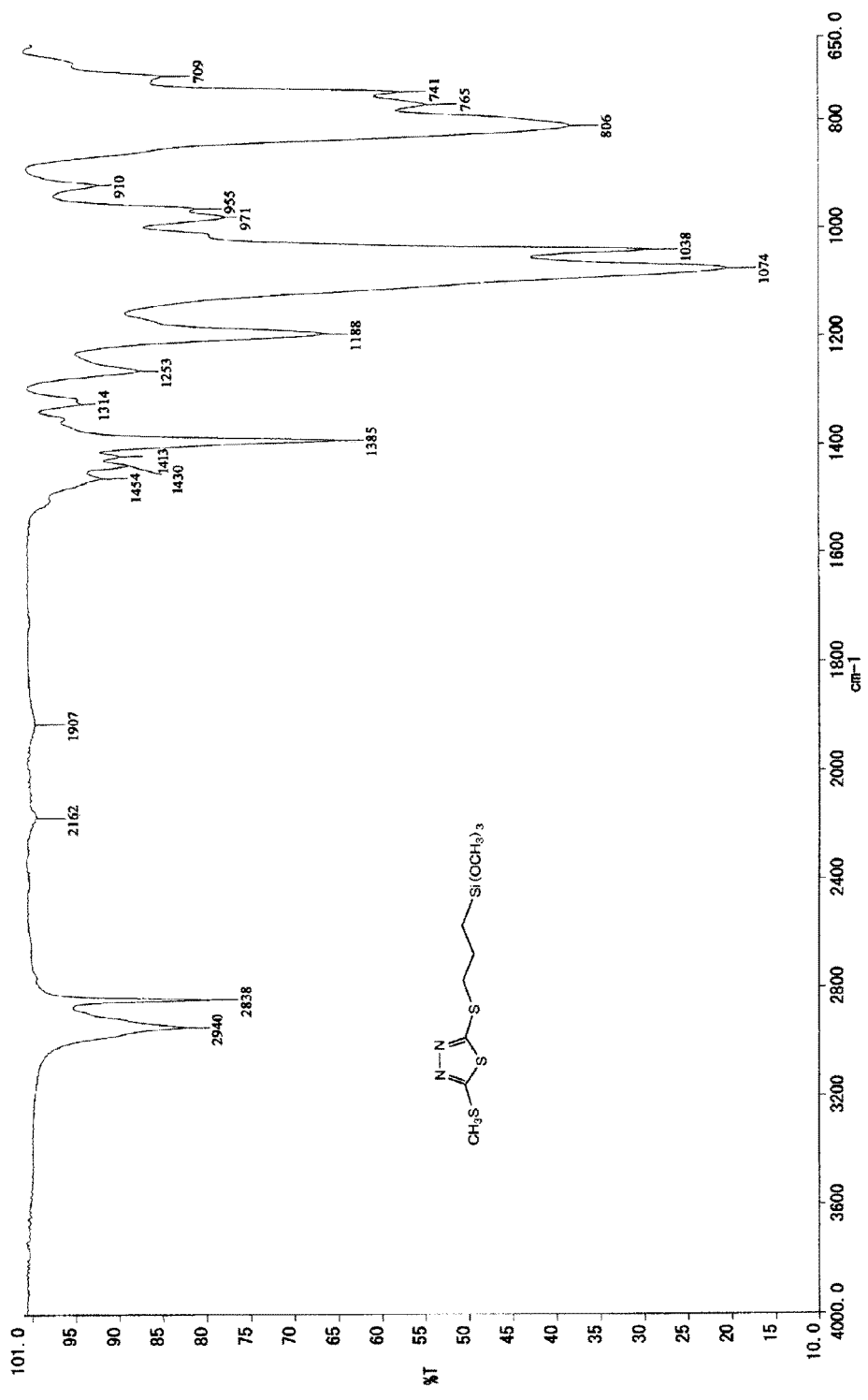
FIG. 13 is an IR spectral chart of the oily material obtained in Example 1-13.

The IR spectral data of the oily substance were as shown in the chart shown in FIG. 13.

From these spectral data, the oily substance obtained was identified as the desired azole silane compound represented by chemical formula (1-13).

[Chem. 37]

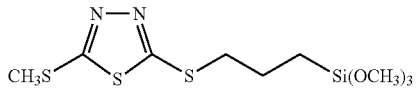

(1-13)

Example 1-14

Synthesis of 2-methylthio-5-[3-(triethoxysilyl)propylthio]-1,3,4-thiadiazole

A suspension composed of 4.93 g (30 mmol) of 2-mercapto-5-methylthio-1,3,4-thiadiazole and 50 ml of dehydrated ethanol was cooled to 10° C., thereto was added 10.2 g (30 mmol) of a 20% sodium ethoxide ethanol solution to form an uniform solution, followed by returning to room temperature and stirring for 30 minutes, and thereto was added dropwise a solution composed of 6.74 g (30 mmol) of 3-chloropropyltriethoxysilane and 10 ml of dehydrated ethanol at room temperature over a period of 10 minutes, followed by further stirring at 78° C. for 6 hours.

The reaction solution was concentrated under a reduced pressure, and 15.4 g of the resulting white viscous substance was extracted three times with 40 ml of diethyl ether, and the extract was filtered and concentrated under a reduced pressure to obtain 9.8 g (26 mmol, yield of 88.6%) of a slightly yellow-brown colored oily substance.

The $^1$H-NMR spectral data of the oily substance obtained were as follows.

$^1$H-NMR (CDCl$_3$) δ: 3.82 (q, 6H), 3.30 (t, 2H), 2.75 (s, 3H), 1.90 (m, 2H), 1.21 (t, 9H), 0.78 (t, 2H).

Figure 14:
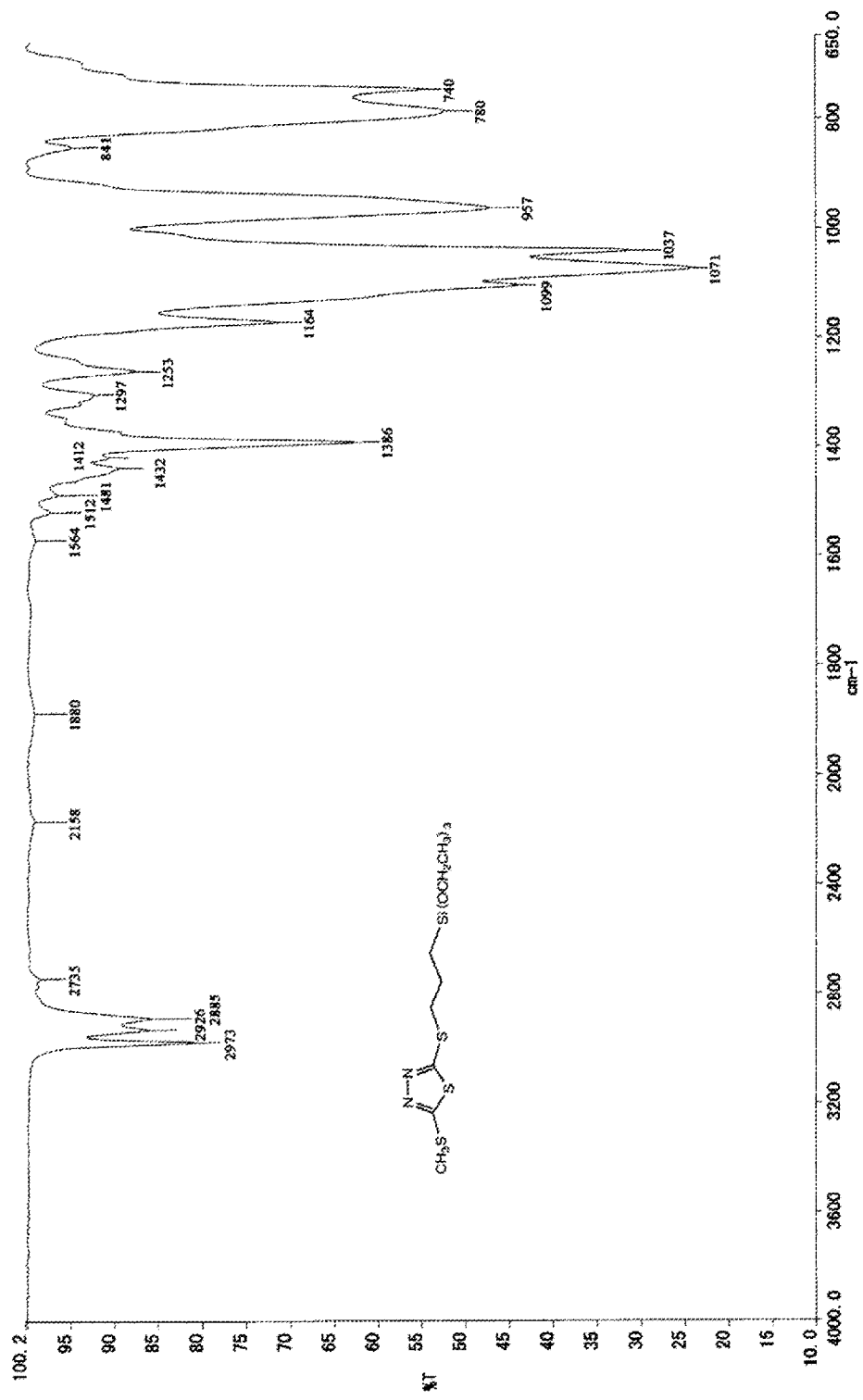
FIG. 14 is an IR spectral chart of the oily material obtained in Example 1-14.

The IR spectral data of the oily substance were as shown in the chart shown in FIG. 14.

From these spectral data, the oily substance obtained was identified as the desired azole silane compound represented by chemical formula (1-14).

[Chem. 38]

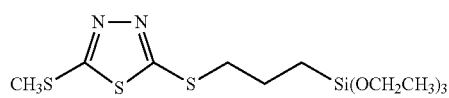

(1-14)

(Synthesis Tests of the Second Group: Azole Silane Compound Represented by Chemical Formula (II-1))

Azole compounds and isocyanatopropylsilane compounds used in the synthesis tests are as follows.

(Azole Compound)

2,2'-Dithiodi(1H-imidazole): synthesized according to the method described in WO 2012/031183.

2,2'-Dithiodi(1H-benzimidazole): synthesized according to the method described in JP-A-2013-14752.

3,3'-Dithiodi(1H-1,2,4-triazole): synthesized according to the method described in WO 2012/031183.

3,3'-Dithiobis(5-amino-1H-1,2,4-triazole): Same as above 4,4'-Dithiodi(1H-1,2,3-triazole): Same as above (Isocyanatopropylsilane Compound)

3-Isocyanatopropyltrimethoxysilane: product of Momentive Performance Materials Japan LLC.

3-Isocyanatopropyltriethoxysilane: product of Shin-Etsu Chemical Co., Ltd.

Example 2-1

Synthesis of 2,2'-dithiobis{1-[3-(trimethoxysilyl) propyl carbamoyl]-1H-imidazole}

To 45 g of dehydrated dimethylformamide was added 2.0 g (10 mmol) of 2,2'-dithiodi(1H-imidazole) and dissolved by stirring at room temperature. Thereto was added dropwise 4.1 g (20 mmol) of 3-isocyanatopropyltrimethoxysilane.

After the exotherm subsided, the reaction solution was stirred at 40° C. for 6 hours and concentrated under a reduced pressure to obtain 6.5 g (10 mmol, yield of 100%) of a brown liquid.

The $^1$H-NMR spectral data of the liquid obtained were as follows.

$^1$H-NMR (DMSO-d$_6$) δ: 8.72 (t, 2H), 7.79 (d, 2H), 6.97 (d, 2H), 3.48 (s, 18H), 3.3-3.2 (m, 4H), 1.6-1.5 (m, 4H), 0.65 (t, 4H).

Figure 15:
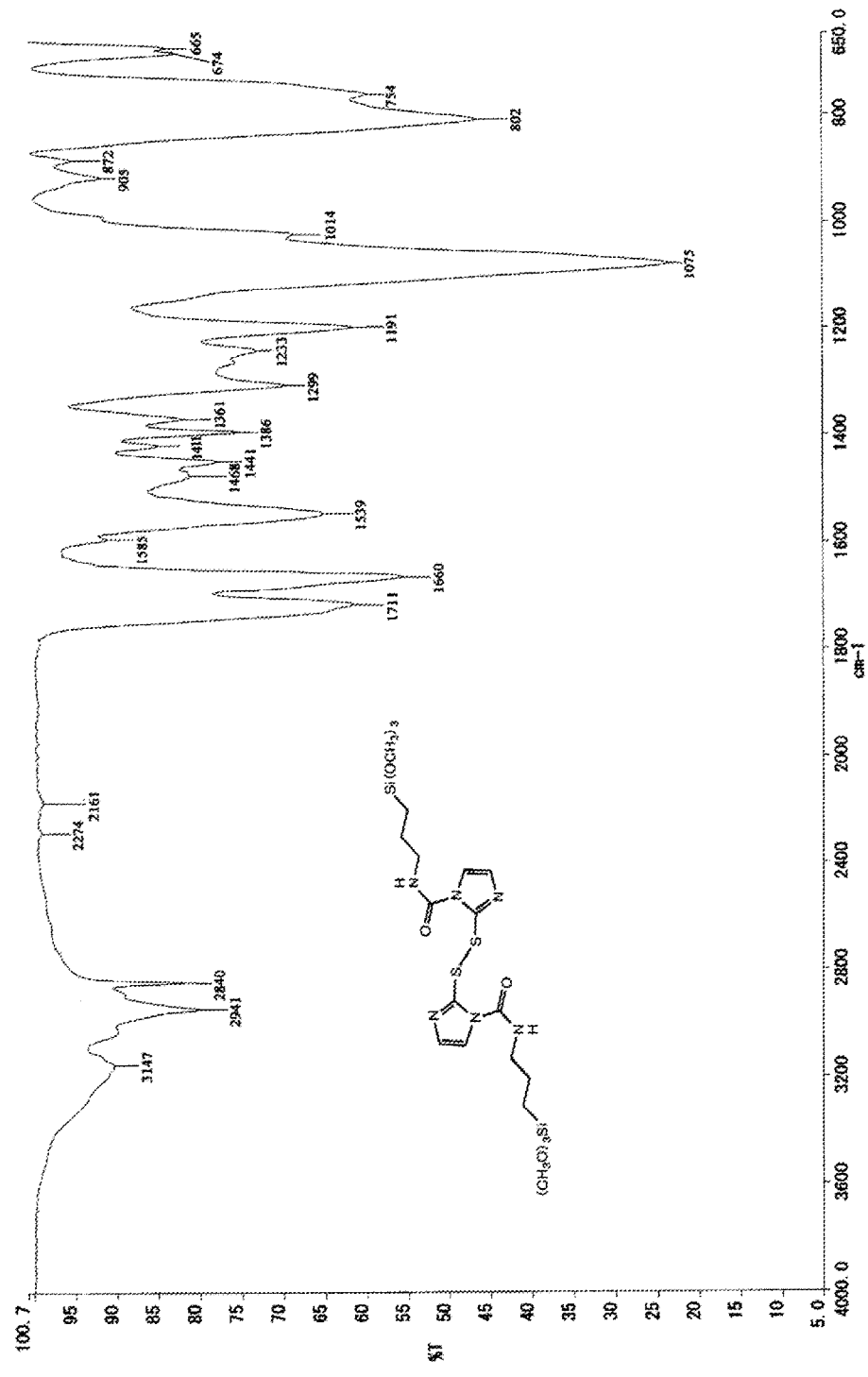
FIG. 15 is an IR spectral chart of the liquid obtained in Example 2-1.

The IR spectral data of the liquid were as shown in the chart shown in FIG. 15.

From these spectral data, the liquid obtained was identified as the desired azole silane compound represented by chemical formula (2-1).

[Chem. 39]

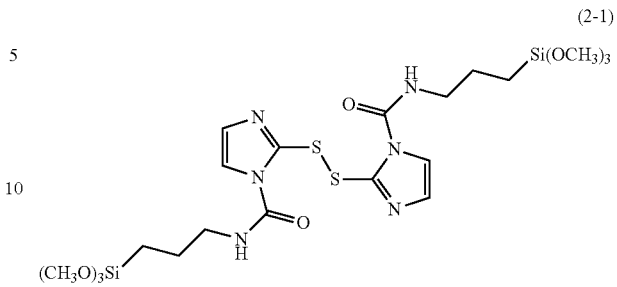

(2-1)

Example 2-2

Synthesis of 2,2'-dithiobis{1-[3-(triethoxysilyl)propylcarbamoyl]-1H-imidazole}

To 26 g of dehydrated dimethylformamide was added 1.0 g (5 mmol) of 2,2'-dithiodi(1H-imidazole) and dissolved by stirring at room temperature. Thereto was added dropwise 2.5 g (10 mmol) of 3-isocyanatopropyltriethoxysilane.

After the exotherm subsided, the reaction solution was stirred at 40° C. for 6 hours and concentrated under a reduced pressure to obtain 3.5 g (5 mmol, yield of 100%) of a brown liquid.

The $^1$H-NMR spectral data of the liquid obtained were as follows.

$^1$H-NMR (DMSO-d$_6$) δ: 8.75 (t, 2H), 7.79 (d, 2H), 6.98 (d, 2H), 3.77 (q, 12H), 3.3-3.2 (m, 4H), 1.7-1.5 (m, 4H), 1.15 (t, 18H), 0.62 (t, 4H).

Figure 16:
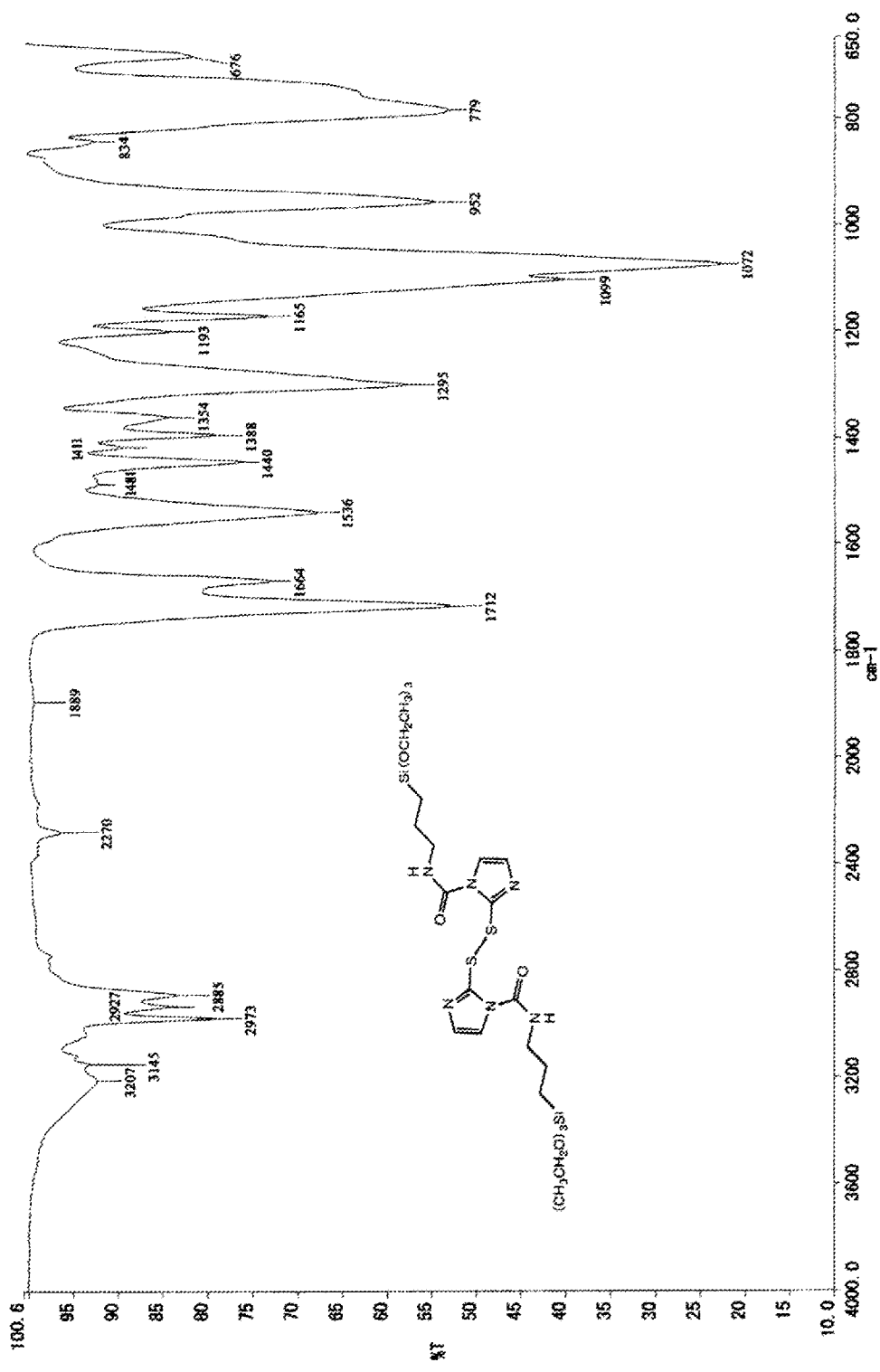
FIG. 16 is an IR spectral chart of the liquid obtained in Example 2-2.

The IR spectral data of the liquid were as shown in the chart shown in FIG. 16.

From these spectral data, the liquid obtained was identified as the desired azole silane compound represented by chemical formula (2-2).

[Chem. 40]

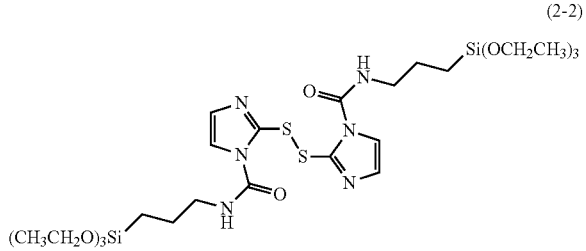

(2-2)

Example 2-3

Synthesis of 2,2'-dithiobis{1-[3-(trimethoxysilyl) propyl carbamoyl]-1H-benzimidazole}

To 16 g of dehydrated dimethylformamide was added 2.5 g (8.4 mmol) of 2,2'-dithiodi(1H-benzimidazole) and dissolved by stirring at room temperature. Thereto was added dropwise 3.5 g (17 mmol) of 3-isocyanatopropyltrimethoxysilane.

After the exotherm subsided, the reaction solution was stirred at 40° C. for 4 hours and concentrated under a reduced pressure to obtain 6.1 g (8.4 mmol, yield of 100%) of a brown liquid.

The $^1$H-NMR spectral data of the liquid obtained were as follows.

$^1$H-NMR (DMSO-d$_6$) δ: 8.55 (s, 2H), 8.07 (d, 2H), 7.72 (d, 2H), 7.4-7.2 (m, 4H), 3.49 (s, 18H), 3.4-3.2 (m, 4H), 1.8-1.6 (m, 4H), 0.68 (t, 4H).

Figure 17:
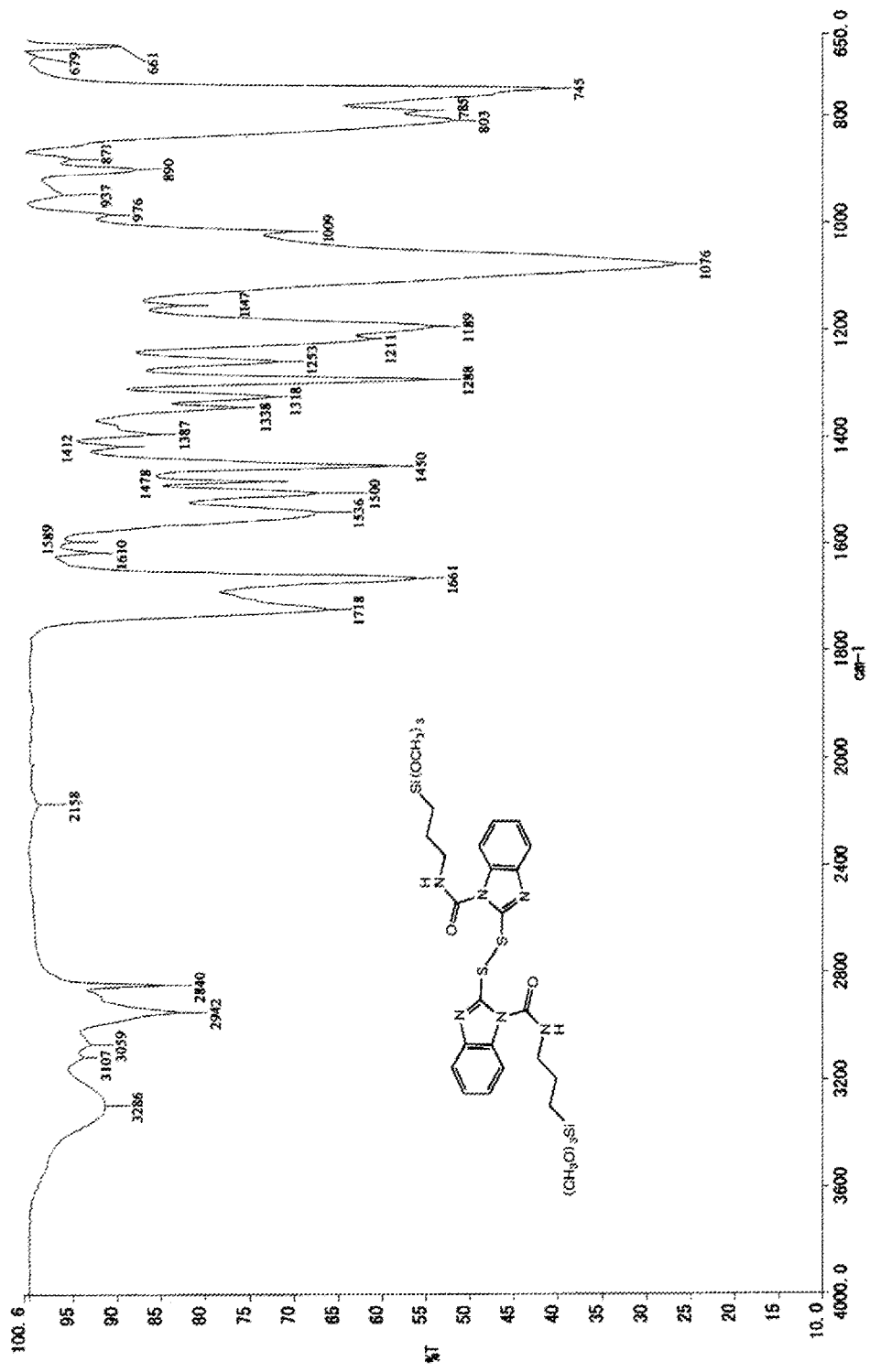
FIG. 17 is an IR spectral chart of the liquid obtained in Example 2-3.

The IR spectral data of the liquid were as shown in the chart shown in FIG. 17.

From these spectral data, the liquid obtained was identified as the desired azole silane compound represented by chemical formula (2-3).

[Chem. 41]

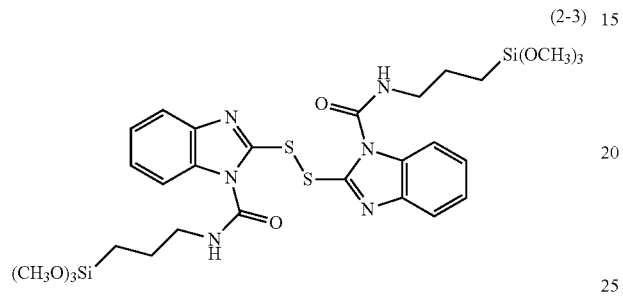

(2-3)

Example 2-4

Synthesis of 2,2'-dithiobis{1-[3-(triethoxysilyl)propylcarbamoyl]-1H-benzimidazole}

To 10 g of dehydrated dimethylformamide was added 1.0 g (3.3 mmol) of 2,2'-dithiodi(1H-benzimidazole) and dissolved by stirring at room temperature. Thereto was added dropwise 1.7 g (6.8 mmol) of 3-isocyanatopropyltriethoxysilane.

After the exotherm subsided, the reaction solution was stirred at 40° C. for 4 hours and concentrated under a reduced pressure to obtain 2.6 g (3.3 mmol, yield of 100%) of a brown liquid.

The $^1$H-NMR spectral data of the liquid obtained were as follows.

$^1$H-NMR (DMSO-d$_6$) δ: 8.56 (s, 2H), 8.08 (d, 2H), 8.73 (d, 2H), 7.5-7.3 (m, 4H), 3.77 (q, 12H), 3.4-3.2 (m, 4H), 1.8-1.6 (m, 4H), 1.16 (t, 18H), 0.67 (t, 4H).

Figure 18:
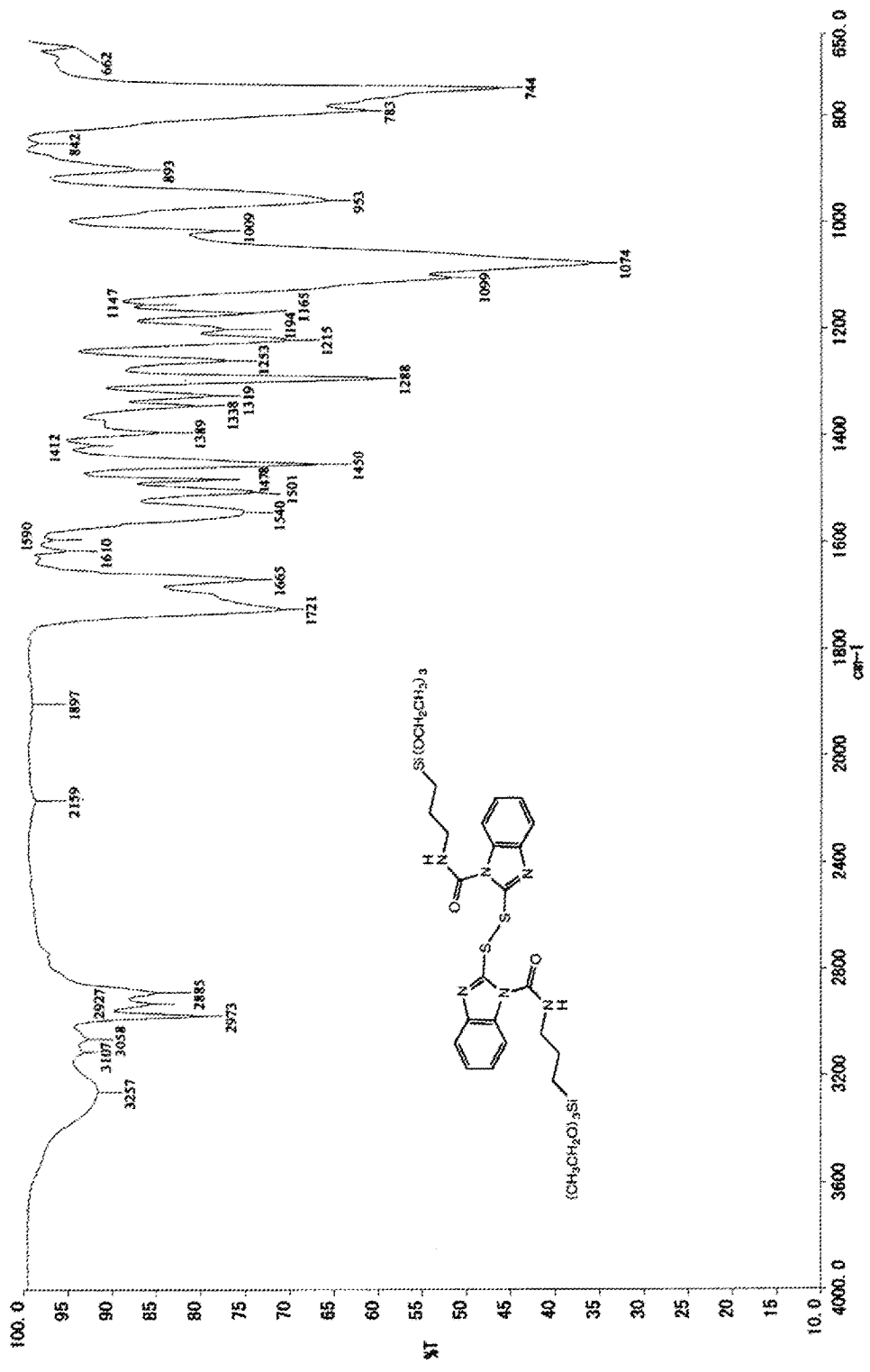
FIG. 18 is an IR spectral chart of the liquid obtained in Example 2-4.

The IR spectral data of the liquid were as shown in the chart shown in FIG. 18.

From these spectral data, the liquid obtained was identified as the desired azole silane compound represented by chemical formula (2-4).

[Chem. 42]

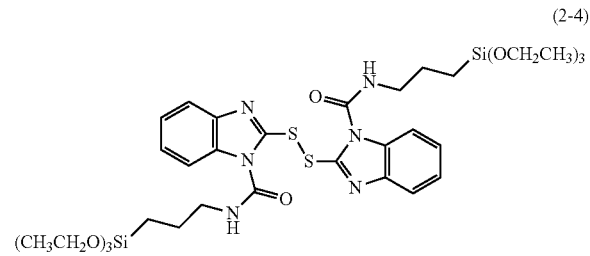

(2-4)

Example 2-5

Synthesis of 3,3'-dithiobis{1-[3-(trimethoxysilyl)propyl carbamoyl]-1H-1,2,4-triazole}

To 150 g of dehydrated dimethylformamide was added 4.02 g (20.1 mmol) of 3,3'-dithiodi(1H-1,2,4-triazole) and dissolved by stirring at room temperature. Thereto was added dropwise 9.49 g (46.2 mmol) of 3-isocyanatopropyltrimethoxysilane. After 10 minutes later, thereto was added 0.92 g (9.1 mmol) of triethylamine, followed by stirring at 60° C. for 8 hours.

The reaction solution was concentrated under a reduced pressure to obtain 12.3 g (20.1 mmol, yield of 100%) of a pale yellow colored liquid.

The $^1$H-NMR spectral data of the liquid obtained were as follows.

$^1$H-NMR (DMSO-d$_6$) δ: 9.20 (s, 2H), 8.78 (t, 2H), 3.47 (s, 18H), 3.21 (q, 4H), 1.60 (m, 4H), 0.59 (t, 4H).

Figure 19:
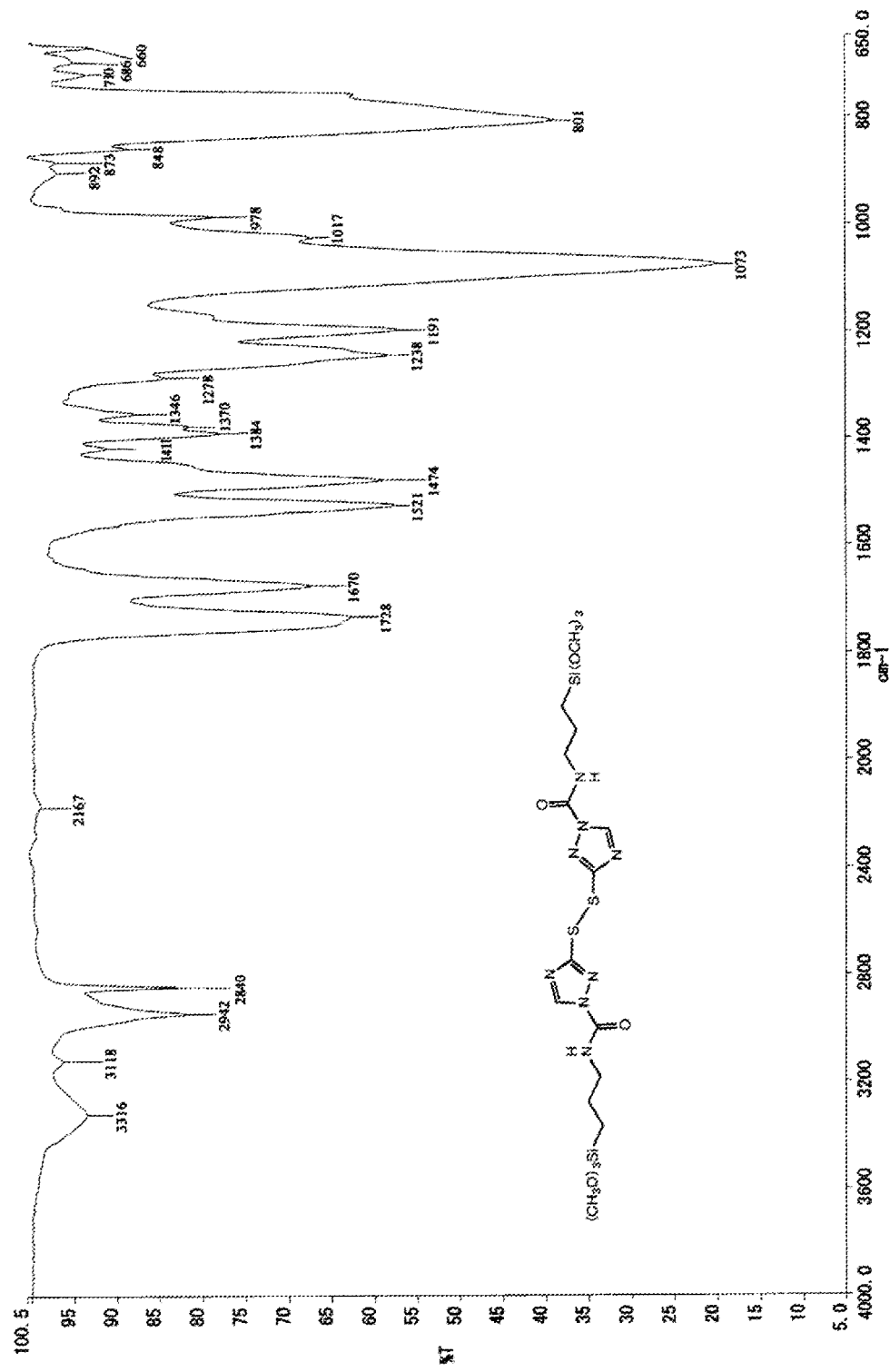
FIG. 19 is an IR spectral chart of the liquid obtained in Example 2-5.

The IR spectral data of the liquid were as shown in the chart shown in FIG. 19.

From these spectral data, the liquid obtained was identified as the desired azole silane compound represented by chemical formula (2-5).

[Chem. 43]

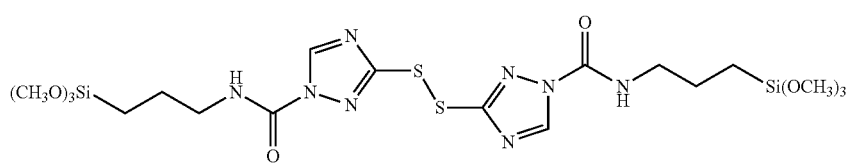

(2-5)

Example 2-6

Synthesis of 3,3'-dithiobis{1-[3-(triethoxysilyl)propylcarbamoyl]-1H-1,2,4-triazole}

To 24 g of dehydrated dimethylformamide was added 1.0 g (5 mmol) of 3,3'-dithiodi(1H-1,2,4-triazole) and dissolved by stirring at room temperature. Thereto was added dropwise 2.5 g (10 mmol) of 3-isocyanatopropyltriethoxysilane. After 20 minutes later, thereto was added 0.2 g (2 mmol) of triethylamine, followed by stirring at 40° C. for 6 hours. The reaction solution was concentrated under a reduced pressure to obtain 3.7 g of crude crystals. They were recrystallized from ethanol to obtain 2.6 g (3.7 mmol, yield of 75.0%) of white crystals.

The melting point and $^1$H-NMR spectral data of the crystal obtained were as follows.

Melting point: 91 to 93° C.

$^1$H-NMR (DMSO-$d_6$) δ: 9.20 (s, 2H), 8.79 (t, 2H), 3.75 (q, 12H), 3.3-3.2 (m, 4H), 1.6-1.5 (m, 4H), 1.16 (t, 18H), 0.57 (t, 4H).

Figure 20:
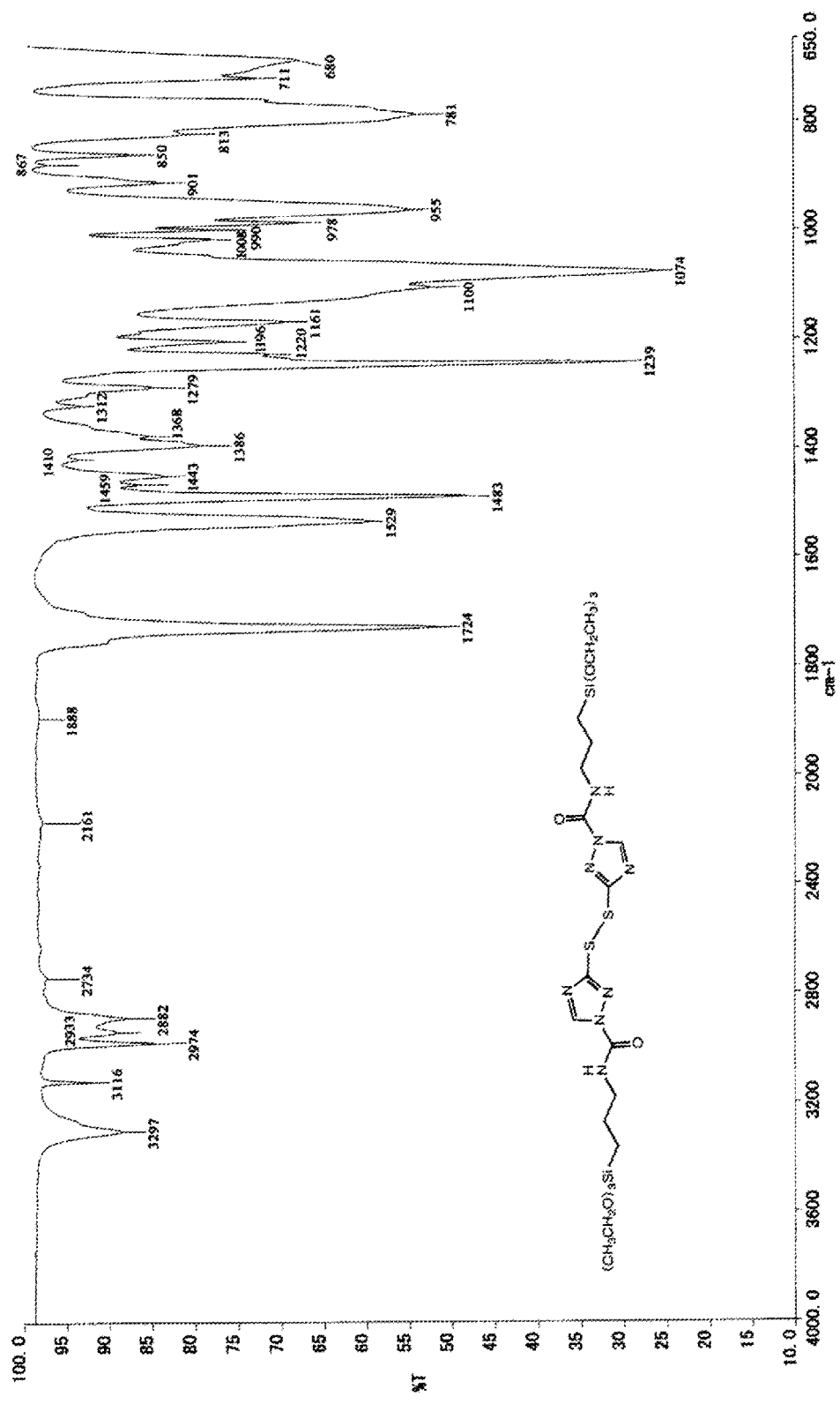
FIG. 20 is an IR spectral chart of the crystal obtained in Example 2-6.

The IR spectral data of the crystal were as shown in the chart shown in FIG. 20.

From these spectral data, the crystal obtained was identified as the desired azole silane compound represented by chemical formula (2-6).

[Chem. 44]

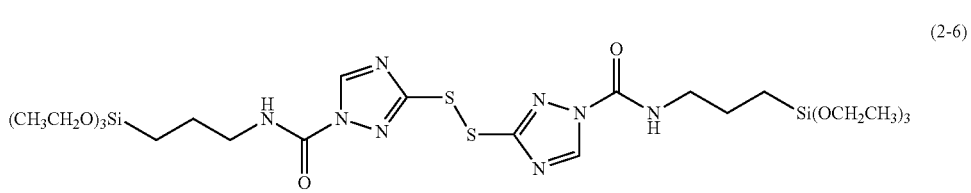

(2-6)

Example 2-7

Synthesis of 3,3'-dithiobis{5-amino-1-[3-(trimethoxysilyl)propylcarbamoyl]-1H-1,2,4-triazole}

To 45 g of dehydrated dimethylformamide was added 2.00 g (8.7 mmol) of 3,3'-dithiobis(5-amino-1H-1,2,4-triazole) and dissolved by stirring at room temperature. Thereto was added dropwise 3.56 g (17.3 mmol) of 3-isocyanatotrimethoxypropylsilane. After 5 minutes later, thereto was added 0.3 g (3 mmol) of triethylamine, followed by stirring at 55° C. for 5 hours.

The reaction solution was concentrated under a reduced pressure, and 12.8 g of the resulting concentrate was recrystallized twice from dehydrated methanol, and dried under a reduced pressure to obtain 3.65 g (5.7 mmol, yield of 65.5%) of white crystals.

The melting point and $^1$H-NMR spectral data of the crystal obtained were as follows.

Melting point: 143 to 144.3° C.

$^1$H-NMR (CDCl$_3$) δ: 8.22 (t, 2H), 7.43 (br. s, 4H), 3.47 (s, 18H), 3.15 (q, 4H), 1.57 (quint, 4H), 0.57 (t, 4H).

Figure 21:
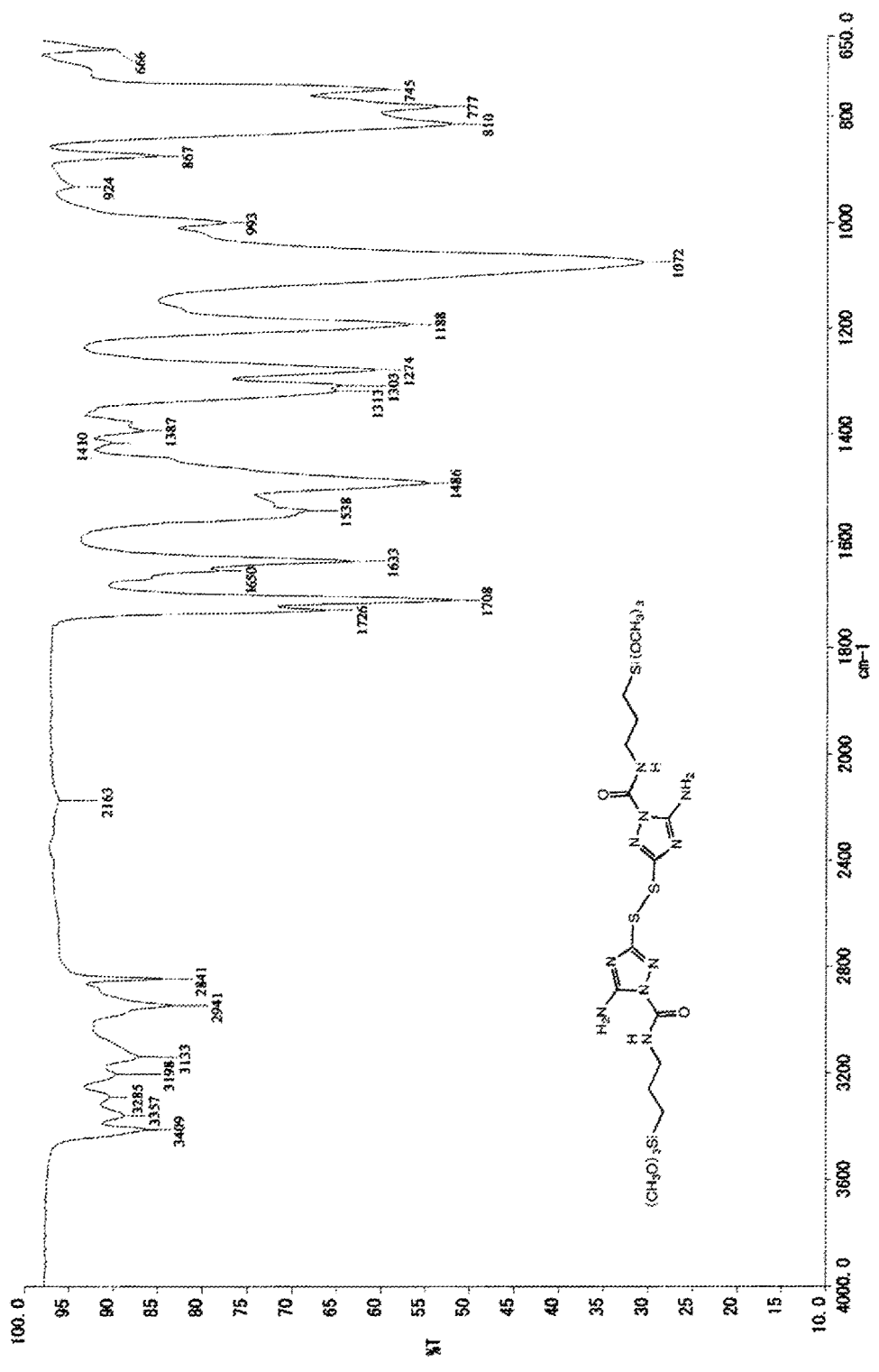
FIG. 21 is an IR spectral chart of the crystal obtained in Example 2-7.

The IR spectral data of the crystal were as shown in the chart shown in FIG. 21.

From these spectral data, the crystal obtained was identified as the desired azole silane compound represented by chemical formula (2-7).

Example 2-8

Synthesis of 3,3'-dithiobis 5-amino-1-[3-(triethoxysilyl)propyl carbamoyl]-1H-1,2,4-triazole To 13 g of dehydrated dimethylformamide was added 1.0 g (4.3 mmol) of 3,3'-dithiobis(5-amino-1H-1,2,4-triazole) and dissolved by stirring at room temperature. Thereto was added dropwise 2.1 g (8.6 mmol) of 3-isocyanatopropyltriethoxysilane. After 20 minutes later, thereto was added 0.2 g (2 mmol) of triethylamine, followed by stirring at 40° C. for 6 hours. The reaction solution was concentrated under a reduced pressure to obtain 3.2 g of crude crystals.

The crystals were recrystallized from ethanol to obtain 2.1 g (2.9 mmol, yield of 67.4%) of white crystals.

The melting point and $^1$H-NMR spectral data of the crystal obtained were as follows.

Melting point: 164 to 165° C.

$^1$H-NMR (CDCl$_3$) δ: 8.23 (t, 2H), 7.44 (s, 4H), 3.74 (q, 12H), 3.2-3.1 (m, 4H), 1.6-1.5 (m, 4H), 1.15 (s, 18H), 0.53 (t, 4H).

Figure 22:
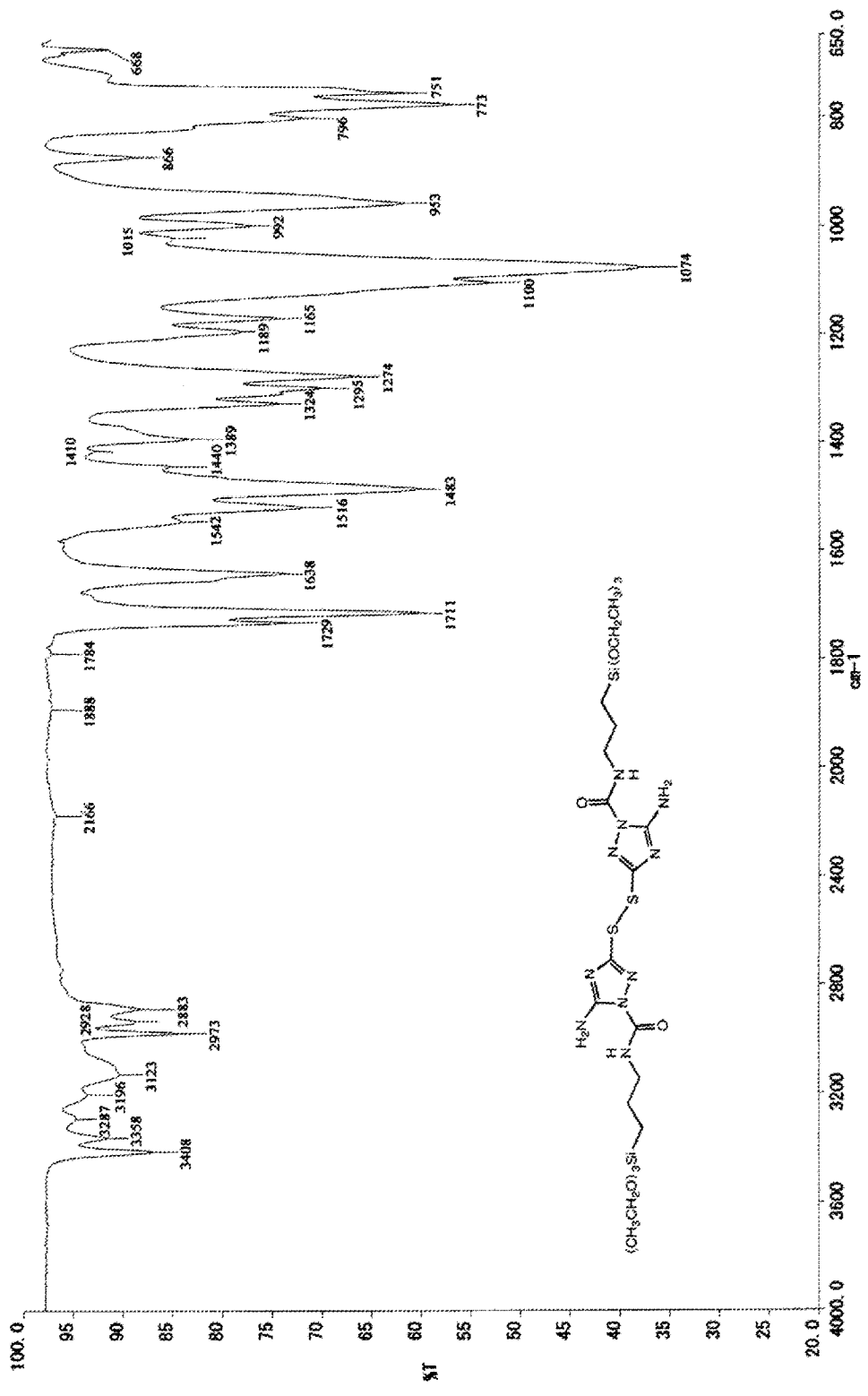
FIG. 22 is an IR spectral chart of the crystal obtained in Example 2-8.

The IR spectral data of the crystal were as shown in the chart shown in FIG. 22.

From these spectral data, the crystal obtained was identified as the desired azole silane compound represented by chemical formula (2-8).

[Chem. 45]

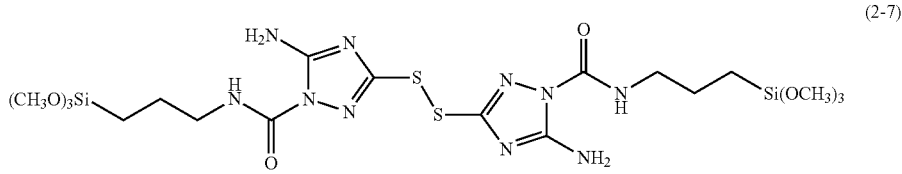

(2-7)

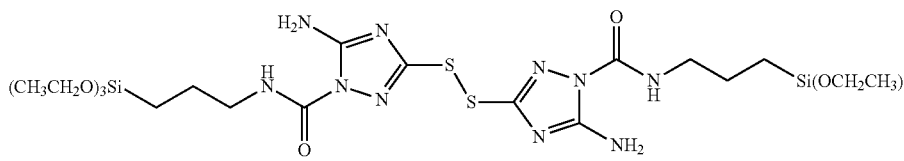

(2-8)

Example 2-9

Synthesis of 4,4'-dithiobis{1-[3-(trimethoxysilyl)propyl carbamoyl]-1H-1,2,3-triazole}

To 50 g of dehydrated dimethylformamide was added 8.67 g (43.3 mmol) of 4,4'-dithiodi(1H-1,2,3-triazole) and dissolved by stirring at room temperature. Thereto was added dropwise 18.7 g (91.1 mmol) of 3-isocyanatopropyltrimethoxysilane. After 20 minutes later, thereto was added 1.84 g (18.2 mmol) of triethylamine, followed by stirring at room temperature for 15 hours.

The reaction solution was concentrated under a reduced pressure, and the liquid concentrate was washed with 130 ml of hexane and dried under a reduced pressure to obtain 26.0 g (42.6 mmol, yield of 98.3%) of a brown liquid.

The $^1$H-NMR spectral data of the liquid obtained were as follows.

$^1$H-NMR (CDCl$_3$) δ: 8.99 (t, 2H), 8.43 (s, 2H), 3.47 (s, 18H), 3.26 (q, 4H), 1.63 (m, 4H), 0.62 (t, 4H).

Figure 23:
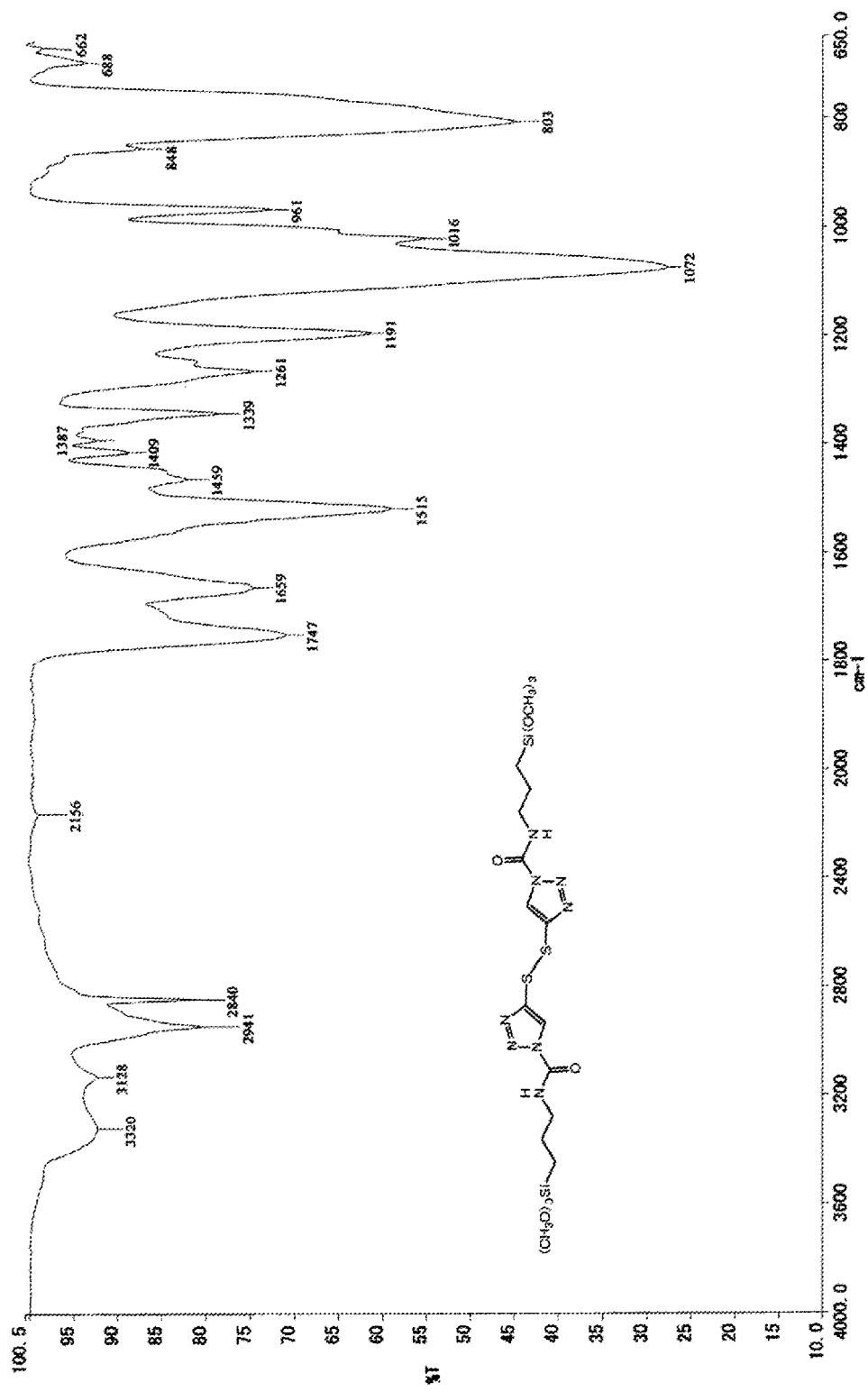
FIG. 23 is an IR spectral chart of the liquid obtained in Example 2-9.

The IR spectral data of the liquid were as shown in the chart shown in FIG. 23.

From these spectral data, the liquid obtained was identified as the desired azole silane compound represented by chemical formula (2-9).

by stirring at room temperature. Thereto was added dropwise 2.5 g (10 mmol) of 3-isocyanatopropyltriethoxysilane. After 20 minutes later, thereto was added 0.1 g (1 mmol) of triethylamine, followed by stirring at 40° C. for 8 hours. The reaction solution was concentrated under a reduced pressure to obtain 3.5 g (5 mmol, yield of 100%) of a brown liquid.

The $^1$H-NMR spectral data of the liquid obtained were as follows.

$^1$H-NMR (CDCl$_3$) δ: 8.99 (t, 2H), 8.45 (s, 2H), 3.75 (q, 12H), 3.4-3.2 (m, 4H), 1.7-1.6 (m, 4H), 1.16 (t, 18H), 0.59 (t, 4H).

Figure 24:
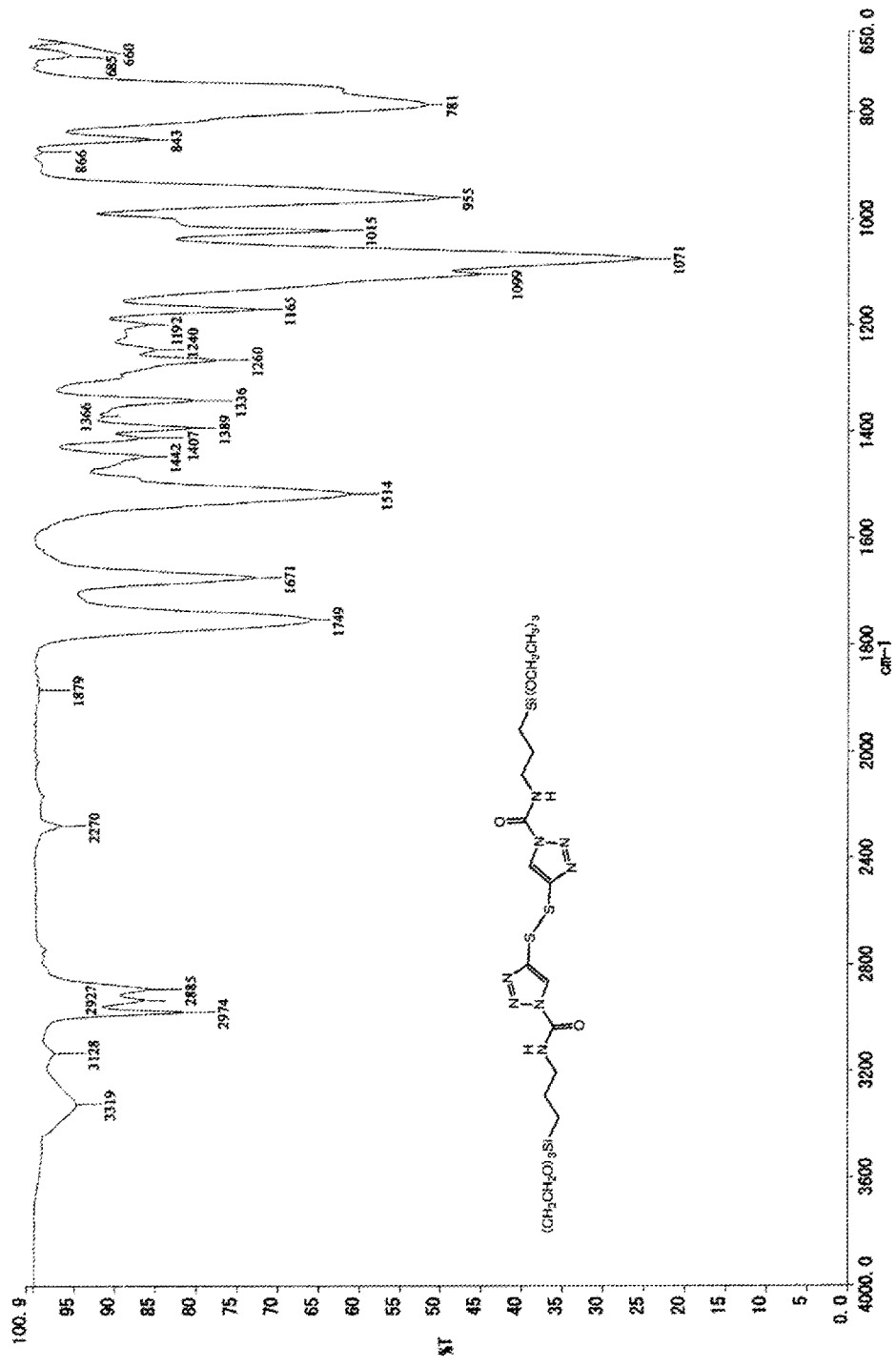
FIG. 24 is an IR spectral chart of the liquid obtained in Example 2-10.

The IR spectral data of the liquid were as shown in the chart shown in FIG. 24.

From these spectral data, the liquid obtained was identified as the desired azole silane compound represented by chemical formula (2-10).

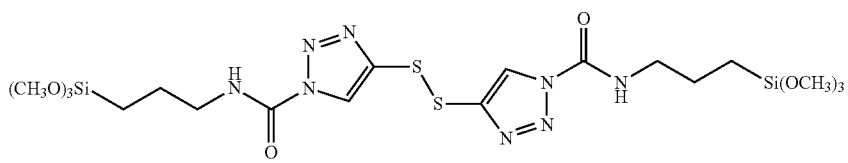

(2-9)

Example 2-10

Synthesis of 4,4'-dithiobis{1-[3-(triethoxysilyl)propylcarbamoyl]-1H-1,2,3-triazole}

To 10 g of dehydrated dimethylformamide was added 1.0 g (5 mmol) of 4,4'-dithiodi(1H-1,2,3-triazole) and dissolved

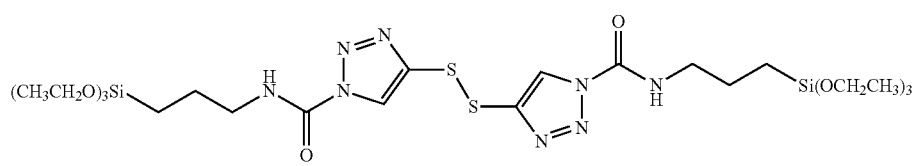

(2-10)

(Evaluation Test of Bonding Property)

The evaluation tests (a) to (g) of bonding property for metal, an inorganic material and a resin material performed in the examples described below are as follows. As to the unit of the formulation described below, "part" means "part by weight" unless otherwise specified.

(Evaluation Test (a) of Bonding Property)
(1) Test Piece

As the test piece, an electrolytic copper foil (thickness: 18 µm) was used.

(2) Treatment of Test Piece

Performed according to the following steps i to iii:
i: Acid cleaning/1 min. (room temperature), and washing with water
ii: Acid cleaning/1 min. (room temperature), washing with water, and drying/1 min. (100° C.)
iii: Immersion in surface treatment solution/1 min. (room temperature), washing with water, and drying/1 min. (100° C.)

(3) Bonding of Resin to Test Piece

On S surface of the test piece treated was laminated and pressed a glass fabric epoxy resin-impregnated prepreg (FR-4 grade) to bond the resin on the test piece, to prepare a printed wiring board.

(4) Evaluation of Bonding Property

A test piece having a width of 10 mm was prepared from the printed wiring board according to "JIS C6481 (1996)" and subjected to a pressure cooker treatment (121° C./100% humidity/100 hours), and then a peel-off strength of the copper foil was measured.

(Evaluation Test (b) of Bonding Property)

The bonding property of resin to copper was evaluated in the same procedure as in Evaluation test (a) except for "laminating a resin for a build-up wiring board (trade name "GX-13" produced by Ajinomoto Fine-Techno Co., Ltd.)" on the S surface of the test piece in place of "laminating and pressing a glass fabric epoxy resin-impregnated prepreg (FR-4 grade)".

(Evaluation Test (c) of Bonding Property)
(1) Test Piece

As the test piece of printed wiring board, a double-sided copper-clad laminate board (base material: FR4, board thickness: 1.0 mm, copper foil thickness: 18 µm, vertical 120 mm×horizontal 110 mm) subjected to electrolytic copper plating (plating thickness: 20 µm) was used.

(2) Treatment of Test Piece

Performed according to the following steps i to iv:
i: Acid cleaning/1 min. (room temperature), and washing with water
ii: Micro-etching with hydrogen peroxide and sulfuric acid/1 min. (room temperature), and washing with water
iii: Acid cleaning/1 min. (room temperature), washing with water, and drying/1 min. (100° C.)
iv: Immersion in surface treatment solution/1 min. (room temperature), washing with water, and drying/1 min. (100° C.)

(3) Formation of Resin Layer on Test Piece

On the test piece treated was coated a solder resist (trade name "PSR-4000AUS308" produced by Taiyo Ink Mfg Co., Ltd.), dried (80° C./30 minutes) and post-cured (150° C./60 minutes) to form a resin layer (coating film) having a thickness of 13 µm.

(4) Evaluation of Bonding Property

According to "JIS K5400-8.5 (1990)", the coating film formed on the test piece was cross-cut in a grid form of 1 mm×1 mm (100 squares) and subjected to a pressure cooker treatment (121° C./100% humidity/100 hours), and then a tape peel test was conducted to measure a number of the squares in which the coating film was not peeled off. Also, the damage degree of the coating film was visually observed.

The judgment criteria of bonding property are shown in Table 1.

TABLE 1

| Damage Degree of Coating Film | Judgment |
|---|---|
| Each cut line is fine and smooth at both edges, and no peeling is observed at the intersection of cut lines and in each square. | A |
| Slight peeling is observed at the intersection of cut lines, but no peeling is observed in each square, and the area of missing portions is 5% or less of the total square area. | B |
| Peeling is observed at both sides of cut line and at the intersection thereof, and the area of missing portions is from 5 to 15% of the total square area. | C |
| The width of peeling due to cut line is wide, and the area of missing portions is from 15 to 35% of the total square area. | D |
| The width of peeling due to cut lines is wider than the width of Judgement D, and the area of missing portions is from 35 to 65% of the total square area. | E |
| The area of peeling is 65% or more of the total square area. | F |

(Evaluation Test (d) of Bonding Property)
(1) Test Piece

As the test piece, an aluminum foil (thickness: 50 µm) was used.

(2) Treatment of Test Piece

Performed according to the following steps i to ii.
i: Acid cleaning/1 min. (room temperature), and washing with water
ii: Immersion in surface treatment solution/1 min. (room temperature), washing with water, and drying/1 min. (100° C.)

(3) Bonding of Resin to Test Piece

On the test piece treated was laminated and pressed a glass fabric epoxy resin-impregnated prepreg (FR-4 grade) to bond the resin on the test piece, to prepare a printed wiring board.

(4) Evaluation of Bonding Property

A test piece having a width of 10 mm was prepared from the printed wiring board according to "JIS C6481 (1996)" and then a peel-off strength of the aluminum foil was measured.

(Evaluation Test (e) of Bonding Property)
(1) Test Piece

As the test piece, a glass fabric epoxy resin-impregnated prepreg (FR-4 grade) was used.

(2) Treatment of Test Piece

On the surface of test piece was performed a treatment with surface treatment solution by a spraying system.

(3) Bonding of Copper Foil to Test Piece

On the test piece treated was laminated and pressed S surface of an electrolytic copper foil (thickness: 35 µm) to bond the copper on the test piece, to prepare a printed wiring board.

(4) Evaluation of Bonding Property

A test piece having a width of 10 mm was prepared from the printed wiring board according to "JIS C6481 (1996)" and then a peel-off strength of the copper foil was measured.

(Evaluation Test (f) of Bonding Property)
(1) Preparation of Resin Composition

Performed according to the following steps i to iii:
i: To 100 parts of surface treatment solution was added 10 parts of barium sulfate, followed by stirring for 5 minutes.
ii: Barium sulfate on which an azole silane compound was supported was filtered, and dried by an oven of 100° C. for one hour.

iii: To 100 parts of a solder resist before curing was added one part of the barium sulfate of Step ii, followed by stirring for 30 minutes to prepare the resin composition.

(2) Production of Printed Wiring Board

The resin composition obtained was coated on S surface of an electrolytic copper foil (thickness: 35 μm) and heated by an oven of 150° C. for one hour to produce a printed wiring board in which a cured material of the resin composition was bonded to the copper foil.

(3) Evaluation of Bonding Property

A test piece having a width of 10 mm was prepared from the printed wiring board according to "JIS C6481 (1996)" and then a peel-off strength of the copper foil was measured.

(Evaluation Test (g) of Bonding Property)

(1) Preparation of Resin Composition

To 100 parts of a solder resist before curing was added one part of a hydrolysate described below, followed by stirring for 30 minutes to prepare the resin composition.

(2) Production of Printed Wiring Board

The resin composition obtained was coated on S surface of an electrolytic copper foil (thickness: 35 μm) and subjected to drying (80° C./30 min.) and post curing (150° C./60 min.) to produce a printed wiring board in which a cured material of the resin composition was bonded to the copper foil.

(3) Evaluation of Bonding Property

A test piece having a width of 10 mm was prepared from the printed wiring board according to "JIS C6481 (1996)" and then a peel-off strength of the copper foil was measured.

(Evaluation Test of First Group: Surface Treatment Solution Containing Azole Silane Compound Represented by Chemical Formula (III-1))

The main raw materials used in the evaluation test of the first group are as follow.

(Main Raw Material)

3-[3-(Trimethoxysilyl)propylthio]-1,2,4-triazole (see Example 1-1)

3-Amino-5-[3-(trimethoxysilyl)propylthio]-1,2,4-triazole (see Example 1-3)

3-Amino-5-[6-(trimethoxysilyl)hexylthio]-1,2,4-triazole (see Example 1-4)

5-Methyl-2-[3-(trimethoxysilyl)propylthio]-1,3,4-thiadiazole (see Example 1-6)

Imidazole silane compound (synthesis method thereof is shown in Reference Example 1)

3-Aminopropyltrimethoxysilane (trade name "KBM-903" produced by Shin-Etsu Chemical Co., Ltd.)

Ethylene glycol monobutyl ether (reagent, produced by Wako Pure Chemical Industries, Ltd.)

Solder resist (acrylate epoxy resin, trade name "PSR-4000AUS308" produced by Taiyo Ink Mfg Co., Ltd.)

Reference Example 1

Synthesis of Imidazole Silane Compound

Imidazole of 3.4 g (0.05 mol) was melted at 95° C., and thereto was added dropwise 11.8 g (0.05 mol) of 3-glycidoxypropyltrimethoxysilane over a period of 30 minutes with stirring under an argon atmosphere. After the completion of the dropwise addition, the reaction was further continued at a temperature of 95° C. for one hour.

The reaction product was obtained as a clear orange viscous liquid (cited from JP-A-H05-186479).

Note: According to JP-A-H05-186479, the reaction product is a mixture of the imidazole silane compounds represented by chemical formulae (3-1) to (3-3).

[Chem. 49]

(3-1)

(3-2)

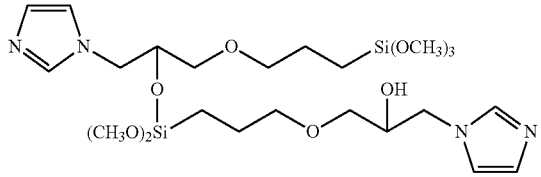
(3-3)

Example 3-1

To 10 g of 3-[3-(trimethoxysilyl)propylthio]-1,2,4-triazole as a silane coupling agent component were added 200 g of ethylene glycol monobutyl ether and then 790 g of water, followed by stirring at room temperature for 2 hours, to prepare a surface treatment solution (hereinafter referred to as Treatment solution A).

As to Treatment solution A, it was confirmed that the methoxysilyl group of the azole silane compound had been hydrolyzed to a hydroxysilyl group, and the evaluation tests (a) to (f) of bonding property were performed.

Subsequently, the volatile component in Treatment solution A was removed under a reduced pressure to obtain a hydrolysate of the azole silane compound. As to the hydrolysate obtained, the evaluation test (g) of bonding property was performed.

The test results obtained were as shown in Table 2.

Example 3-2

A surface treatment solution (hereinafter referred to as Treatment solution B) was prepared in the same manner as in Example 3-1 except for using "3-amino-5-[3-(trimethoxysilyl)propylthio]-1,2,4-triazole" in place of "3-[3-(trimethoxysilyl)propylthio]-1,2,4-triazole".

As to Treatment solution B, it was confirmed that the methoxysilyl group of the azole silane compound had been hydrolyzed to a hydroxysilyl group, and the evaluation tests (a) to (f) of bonding property were performed.

Subsequently, the volatile component in Treatment solution B was removed under a reduced pressure to obtain a hydrolysate of the azole silane compound. As to the hydrolysate obtained, the evaluation test (g) of bonding property was performed.

The test results obtained were as shown in Table 2.

Example 3-3

A surface treatment solution (hereinafter referred to as Treatment solution C) was prepared in the same manner as in Example 3-1 except for using "3-amino-5-[6-(trimethoxysilyl)hexylthio]-1,2,4-triazole" in place of "3-[3-(trimethoxysilyl)propylthio]-1,2,4-triazole".

As to Treatment solution C, it was confirmed that the methoxysilyl group of the azole silane compound had been hydrolyzed to a hydroxysilyl group, and the evaluation tests (a) to (f) of bonding property were performed.

Subsequently, the volatile component in Treatment solution C was removed under a reduced pressure to obtain a hydrolysate of the azole silane compound. As to the hydrolysate obtained, the evaluation test (g) of bonding property was performed.

The test results obtained were as shown in Table 2.

Example 3-4

A surface treatment solution (hereinafter referred to as Treatment solution D) was prepared in the same manner as in Example 3-1 except for using "5-methyl-2-[3-(trimethoxysilyl)propylthio]-1,3,4-thiadiazole" in place of "3-[3-(trimethoxysilyl)propylthio]-1,2,4-triazole".

As to Treatment solution D, it was confirmed that the methoxysilyl group of the azole silane compound had been hydrolyzed to a hydroxysilyl group, and the evaluation tests (a) to (f) of bonding property were performed.

Subsequently, the volatile component in Treatment solution D was removed under a reduced pressure to obtain a hydrolysate of the azole silane compound. As to the hydrolysate obtained, the evaluation test (g) of bonding property was performed.

The test results obtained were as shown in Table 2.

Comparative Example 3-1

A surface treatment solution (hereinafter referred to as Treatment solution E) was prepared in the same manner as in Example 3-1 except for using "imidazole silane compound" in place of "3-[3-(trimethoxysilyl)propylthio]-1,2,4-triazole".

As to Treatment solution E, it was confirmed that the methoxysilyl group of the imidazole silane had been hydrolyzed to a hydroxysilyl group, and the evaluation tests (a) to (f) of bonding property were performed.

Subsequently, the volatile component in Treatment solution E was removed under a reduced pressure to obtain a hydrolysate of the imidazole silane compound. As to the hydrolysate obtained, the evaluation test (g) of bonding property was performed.

The test results obtained were as shown in Table 2.

Comparative Example 3-2

A surface treatment solution (hereinafter referred to as Treatment solution F) was prepared in the same manner as in Example 3-1 except for using "3-aminopropyltrimethoxysilane" in place of "3-[3-(trimethoxysilyl)propylthio]-1,2,4-triazole".

As to Treatment solution F, it was confirmed that the methoxysilyl group of the 3-aminopropyltrimethoxysilane had been hydrolyzed to a hydroxysilyl group, and the evaluation tests (a) to (f) of bonding property were performed.

Subsequently, the volatile component in Treatment solution F was removed under a reduced pressure to obtain a hydrolysate of 3-aminopropyltrimethoxysilane. As to the hydrolysate obtained, the evaluation test (g) of bonding property was performed.

The test results obtained were as shown in Table 2.

Comparative Example 3-3

Without using a silane coupling agent, 200 g of ethylene glycol monobutyl ether and 790 g of water were mixed, followed by stirring at room temperature for 2 hours, to prepare a surface treatment solution (hereinafter referred to as Treatment solution G).

As to Treatment solution (G), the evaluation tests (a) to (f) of bonding property were performed and the test results obtained were as shown in Table 2.

Also, the evaluation test (g) of bonding property was performed without adding anything to the solder resist. The test result obtained was as shown in Table 2.

TABLE 2

| | | | Evaluation Test of Bonding property | | | | | | |
|---|---|---|---|---|---|---|---|---|---|
| | | | (a) (b) Peel-off Strength (kN/m) | | (c) Damage Degree of Coating Film | (d) (e) (f) (g) Peel-off Strength (kN/m) | | | |
| Example | 3-1 | Treatment Solution A | 0.84 | 0.66 | A | 0.56 | 0.71 | 0.70 | 0.75 |
| | 3-2 | Treatment Solution B | 0.83 | 0.71 | A | 0.52 | 0.69 | 0.70 | 0.79 |
| | 3-3 | Treatment Solution C | 0.75 | 0.50 | B | 0.44 | 0.61 | 0.55 | 0.71 |
| | 3-4 | Treatment Solution D | 0.61 | 0.44 | C | 0.40 | 0.49 | 0.47 | 0.55 |
| Comparative Example | 3-1 | Treatment Solution E | 0.13 | 0.11 | F | 0.11 | 0.12 | 0.12 | 0.12 |
| | 3-2 | Treatment Solution F | 0.11 | 0.15 | F | 0.12 | 0.11 | 0.10 | 0.15 |
| | 3-3 | Treatment Solution G | 0.13 | 0.22 | F | 0.10 | 0.14 | 0.14 | 0.15 |

(Evaluation Test of Second Group: Surface Treatment Solution Containing Azole Silane Compound Represented by Chemical Formula (IV-1))

The main raw materials used in the evaluation test of the second group are as follow.

(Main Raw Material)

2,2'-Dithiobis{1-[3-(trimethoxysilyl)propylcarbamoyl]-1H-imidazole} (see Example 2-1)

3,3'-Dithiobis {1-[3-(trimethoxysilyl)propyl carbamoyl]-1H-1,2,4-triazole} (see Example 2-5)

3,3'-Dithiobis {5-amino-1-[3-(trimethoxysilyl)propylcarbamoyl]-1H-1,2,4-triazole} (see Example 2-7)

4,4'-Dithiobis{1-[3-(trimethoxysilyl)propylcarbamoyl]-1H-1,2,3-triazole} (see Example 2-9)
Imidazole silane compound (same as described above)
3-aminopropyltrimethoxysilane (same as described above)
Ethylene glycol monobutyl ether (same as described above)
Solder resist (same as described above)

Example 4-1

To 10 g of 2,2'-dithiobis{1-[3-(trimethoxysilyl)propylcarbamoyl]-1H-imidazole} as a silane coupling agent component were added 200 g of ethylene glycol monobutyl ether and then 790 g of water, followed by stirring at room temperature for 2 hours, to prepare a surface treatment solution (hereinafter referred to as Treatment solution H).

As to Treatment solution H, it was confirmed that the methoxysilyl group of the azole silane compound had been hydrolyzed to a hydroxysilyl group, and the evaluation tests (a) to (f) of bonding property were performed.

Subsequently, the volatile component in Treatment solution H was removed under a reduced pressure to obtain a hydrolysate of the azole silane compound. As to the hydrolysate obtained, the evaluation test (g) of bonding property was performed.

The test results obtained were as shown in Table 3.

Example 4-2

A surface treatment solution (hereinafter referred to as Treatment solution J) was prepared in the same manner as in Example 4-1 except for using "3,3'-dithiobis{1-[3-(trimethoxysilyl)propylcarbamoyl]-1H-1,2,4-triazole}" in place of "2,2'-dithiobis{1-[3-(trimethoxysilyl)propylcarbamoyl]-1H-imidazole}".

As to Treatment solution J, it was confirmed that the methoxysilyl group of the azole silane compound had been hydrolyzed to a hydroxysilyl group, and the evaluation tests (a) to (f) of bonding property were performed.

Subsequently, the volatile component in Treatment solution J was removed under a reduced pressure to obtain a hydrolysate of the azole silane compound. As to the hydrolysate obtained, the evaluation test (g) of bonding property was performed.

The test results obtained were as shown in Table 3.

Example 4-3

A surface treatment solution (hereinafter referred to as Treatment solution K) was prepared in the same manner as in Example 4-1 except for using "3,3'-dithiobis{5-amino-1-[3-(trimethoxysilyl)propylcarbamoyl]-1H-1,2,4-triazole}" in place of "2,2'-dithiobis{1-[3-(trimethoxysilyl)propylcarbamoyl]-1H-imidazole}".

As to Treatment solution K, it was confirmed that the methoxysilyl group of the azole silane compound had been hydrolyzed to a hydroxysilyl group, and the evaluation tests (a) to (f) of bonding property were performed.

Subsequently, the volatile component in Treatment solution K was removed under a reduced pressure to obtain a hydrolysate of the azole silane compound. As to the hydrolysate obtained, the evaluation test (g) of bonding property was performed.

The test results obtained were as shown in Table 3.

Example 4-4

A surface treatment solution (hereinafter referred to as Treatment solution L) was prepared in the same manner as in Example 4-1 except for using "4,4'-dithiobis{1-[3-(trimethoxysilyl)propylcarbamoyl]-1H-1,2,3-triazole}" in place of "2,2'-dithiobis{1-[3-(trimethoxysilyl)propylcarbamoyl]-1H-imidazole}".

As to Treatment solution L, it was confirmed that the methoxysilyl group of the azole silane compound had been hydrolyzed to a hydroxysilyl group, and the evaluation tests (a) to (f) of bonding property were performed.

Subsequently, the volatile component in Treatment solution L was removed under a reduced pressure to obtain a hydrolysate of the azole silane compound. As to the hydrolysate obtained, the evaluation test (g) of bonding property was performed.

The test results obtained were as shown in Table 3.

Example 4-5

The evaluation test (a) of bonding property was performed in the same manner as in Example 4-1 except that before the treatment of copper foil surface with Treatment solution H, the copper foil was immersed (room temperature/30 sec.) in an aqueous 3% copper acetate solution, washed with water and dried (100° C./1 min.).

The test result obtained was as shown in Table 3.

Example 4-6

The evaluation tests (a) and (c) of bonding property were performed in the same manner as in Example 4-1 except that after the treatment of copper foil surface with Treatment solution H, the copper foil was immersed (room temperature/1 min.) in an aqueous 10% acetic acid solution, washed with water and dried (100° C./1 min.).

The test results obtained were as shown in Table 3.

Comparative Example 4-1

The test data of Comparative Example 3-1 were incorporated and shown in Table 3.

Comparative Example 4-2

The test data of Comparative Example 3-2 were incorporated and shown in Table 3.

Comparative Example 4-3

The test data of Comparative Example 3-3 were incorporated and shown in Table 3.

Comparative Example 4-4

The evaluation test (a) of bonding property was performed in the same manner as in Comparative Example 3-3 except that before the treatment of copper foil surface with Treatment solution G, the copper foil was immersed (room temperature/30 sec.) in an aqueous 3% copper acetate solution, washed with water and dried (100° C./1 min.).

The test result obtained was as shown in Table 3.

Comparative Example 4-5

The evaluation tests (a) and (c) of bonding property were performed in the same manner as in Comparative Example 3-3 except that after the treatment of copper foil surface with Treatment solution G, the copper foil was immersed (room temperature/1 min.) in an aqueous 10% acetic acid solution, washed with water and dried (100° C./1 min.).

The test results obtained were as shown in Table 3.

TABLE 3

| | | (a) Peel-off Strength (kN/m) | (b) | (c) Damage Degree of Coating Film | (d) | (e) | (f) | (g) |
|---|---|---|---|---|---|---|---|---|
| | | | | | \multicolumn{4}{c}{Peel-off Strength (kN/m)} | | | |
| Example | 4-1 Treatment Solution H | 0.43 | 0.40 | C | 0.31 | 0.66 | 0.62 | 0.72 |
| | 4-2 Treatment Solution J | 0.83 | 0.71 | A | 0.55 | 0.70 | 0.66 | 0.81 |
| | 4-3 Treatment Solution K | 0.75 | 0.50 | B | 0.51 | 0.58 | 0.59 | 0.70 |
| | 4-4 Treatment Solution L | 0.61 | 0.44 | C | 0.38 | 0.51 | 0.48 | 0.61 |
| | 4-5 Treatment Solution H | 0.48 | | | | | | |
| | 4-6 Treatment Solution H | 0.44 | | B | | | | |
| Comparative Example | 4-1 Treatment Solution E | 0.13 | 0.11 | F | 0.11 | 0.12 | 0.12 | 0.12 |
| | 4-2 Treatment Solution F | 0.11 | 0.15 | F | 0.12 | 0.11 | 0.10 | 0.15 |
| | 4-3 Treatment Solution G | 0.13 | 0.22 | F | 0.10 | 0.14 | 0.14 | 0.15 |
| | 4-4 Treatment Solution G | 0.13 | | | | | | |
| | 4-5 Treatment Solution G | 0.13 | | F | | | | |

Although the present invention has been described in detail and by reference to specific embodiments, it is apparent to those skilled in the art that it is possible to add various alterations and modifications without departing from the spirit and the scope of the present invention. The present application is based on a Japanese patent application (No. 2013-138541) filed on Jul. 2, 2013, a Japanese patent application (No. 2013-175314) filed on Aug. 27, 2013, a Japanese patent application (No. 2013-206978) filed on Oct. 2, 2013, and a Japanese patent application (No. 2013-266400) filed on Dec. 25, 2013, and the contents thereof are incorporated herein by reference.

INDUSTRIAL APPLICABILITY

Since the azole silane compound according to the present invention can provide a silane coupling agent to which a function of preventing metal from corrosion, which is the feature of the azole compound, and a function of curing an epoxy resin or a urethane resin are added, it is expected to utilize in a composite material such as a printed wiring board produced by combining a large number of different kinds of materials.

According to the present invention, since the bonding property (adhesion property) of metal, an inorganic material and a resin material can be sufficiently ensured, the surface of base material can be maintained in a smooth state without roughening it. Therefore, the present invention is able to largely contribute to realization of miniaturization, thickness reduction, higher frequency, higher density, or the like in a multilayer printed wiring board so that the industrial applicability is great.

The invention claimed is:

1. An azole silane compound represented by the following chemical formula (I-1) or (II-1):

[Chem. 1]

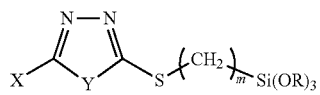

(I-1)

(in formula (I-1), X represents a hydrogen atom, —$CH_3$, —$NH_2$, —SH, or —$SCH_3$; Y represents —NH—; R represents —$CH_3$ or —$CH_2CH_3$; and m represents an integer of from 1 to 12);

[Chem. 2]

$A_1$-S—S-$A_1$ (II-1)

(in formula (II-1), $A_1$ represents

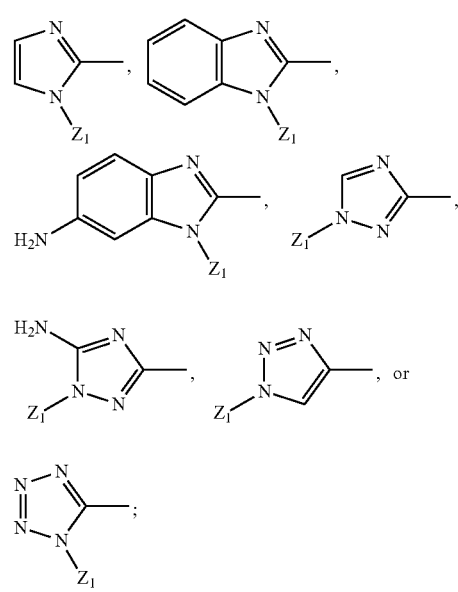

$Z_1$ represents —CO—NH—$(CH_2)_m$—Si(OR)$_3$;
R represents —$CH_3$ or —$CH_2CH_3$; and
m represents an integer of from 1 to 12).

2. A synthesis method of an azole silane compound represented by the following chemical formula (I-1):

[Chem. 3]

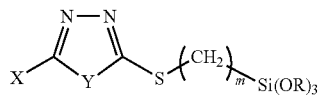
(I-1)

(in formula (I-1), X represents a hydrogen atom, —CH$_3$, —NH$_2$, —SH or —SCH$_3$; Y represents —NH— or —S—; R represents —CH$_3$ or —CH$_2$CH$_3$; and m represents an integer of from 1 to 12);
wherein the synthesis method comprises a step of reacting an azole compound represented by the following chemical formula (I-2) with a halogenated alkylsilane compound represented by the following chemical formula (I-3) in the presence of a dehydrohalogenation agent:

[Chem. 4]

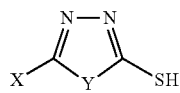
(I-2)

(in formula (I-2), X represents a hydrogen atom, —CH$_3$, —NH$_2$, —SH or —SCH$_3$; and Y represents —NH— or —S—);

[Chem. 5]

(I-3)

(in formula (I-3), R represents —CH$_3$ or —CH$_2$CH$_3$, m represents an integer of from 1 to 12; and Hal represents a chlorine atom, a bromine atom or an iodine atom).

3. A synthesis method of an azole silane compound represented by the following chemical formula (II-1):

[Chem. 6]

A$_1$-S—S-A$_1$ (II-1)

(in formula (II-1), A$_1$ represents

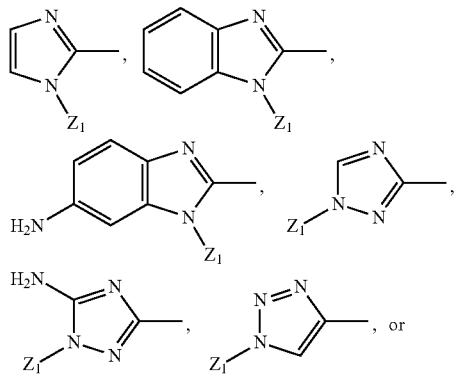

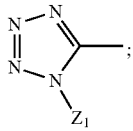
;

Z$_1$ represents —CO—NH—(CH$_2$)$_m$—Si(OR)$_3$;
R represents —CH$_3$ or —CH$_2$CH$_3$; and
m represents an integer of from 1 to 12);
wherein the synthesis method comprises a step of reacting an azole compound represented by the following chemical formula (II-2) with an isocyanatoalkylsilane compound represented by the following chemical formula (II-3):

[Chem. 7]

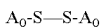
A$_0$-S—S-A$_0$ (II-2)

(in formula (II-2), A$_0$ represents

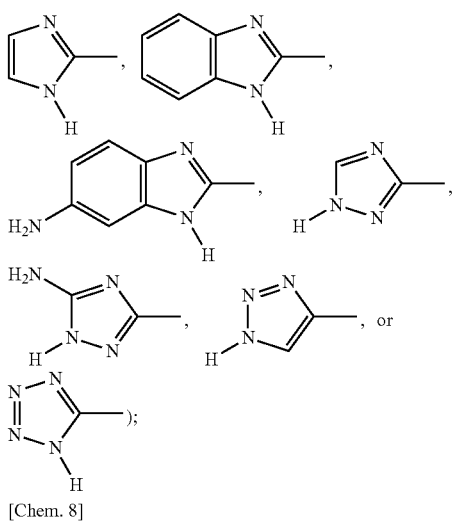
);

[Chem. 8]

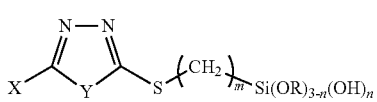
OCN—(CH$_2$)$_m$—Si(OR)$_3$ (II-3)

(in formula (II-3), R represents —CH$_3$ or —CH$_2$CH$_3$, and m represents an integer of from 1 to 12).

4. A silane coupling agent comprising an azole silane compound represented by the following chemical formula (III-1) or (IV-1) as a component:

[Chem. 9]

(III-1)

(in formula X represents a hydrogen atom, —CH$_3$, —NH$_2$, —SH or —SCH$_3$; Y represents —NH— or —S—; R represents —CH$_3$ or —CH$_2$CH$_3$, m represents an integer of from 1 to 12; and n represents 0 or an integer of from 1 to 3);

[Chem. 10]

$A_2$-S—S-$A_2$ (IV-1)

(in formula (IV-1), $A_2$ represents

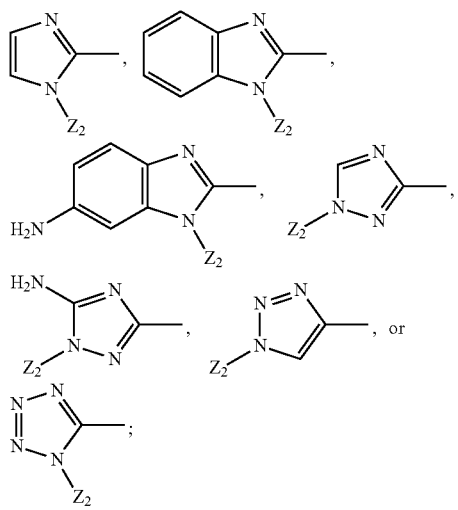

$Z_2$ represents —CO—NH—$(CH_2)_m$—Si(OR)$_{3-n}$(OH)$_n$;
R represents —$CH_3$ or —$CH_2CH_3$;
m represents an integer of from 1 to 12; and
n represents 0 or an integer of from 1 to 3).

5. An insulating composition comprising the silane coupling agent described in claim 4 and a resin material or an inorganic material.

6. The insulating composition according to claim 5, wherein the resin material is at least one selected from the group consisting of an acrylate resin, an epoxy resin and a polyimide resin.

7. The insulating composition according to claim 5, wherein the inorganic material is at least one selected from the group consisting of silicon, a ceramic and a glass.

8. An insulating material comprising the insulating composition described in claim 5.

9. A printed wiring board comprising an insulating layer obtained from the insulating composition described in claim 5.

10. An electronic device comprising an insulating layer obtained from the insulating composition described in claim 5.

11. A surface treatment solution comprising an azole silane compound represented by the following chemical formula (III-1) or (IV-1):

[Chem. 11]

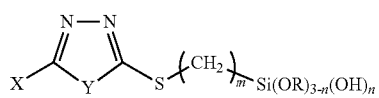

(III-1)

(in formula X represents a hydrogen atom, —$CH_3$, —$NH_2$, —SH or —$SCH_3$; Y represents —NH— or —S—; R represents —$CH_3$ or —$CH_2CH_3$, m represents an integer of from 1 to 12; and n represents 0 or an integer of from 1 to 3);

[Chem. 12]

$A_2$-S—S-$A_2$ (IV-1)

(in formula (IV-1), $A_2$ represents

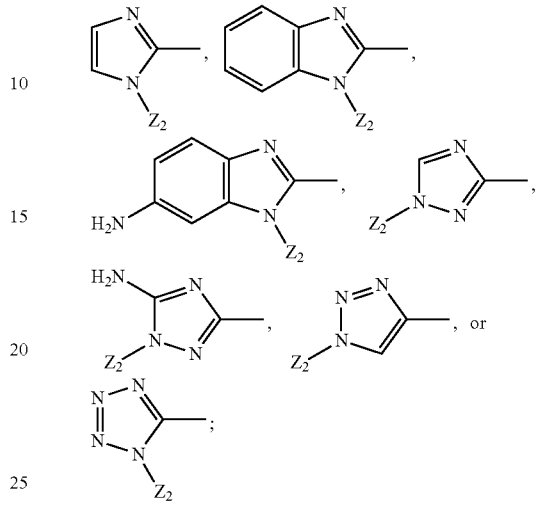

$Z_2$ represents —CO—NH—$(CH_2)_m$—Si(OR)$_{3-n}$(OH)$_n$;
R represents —$CH_3$ or —$CH_2CH_3$;
m represents an integer of from 1 to 12; and
n represents 0 or an integer of from 1 to 3).

12. The surface treatment solution according to claim 11, which is used for treating a surface of at least one selected from the group consisting of a metal, an inorganic material and a resin material.

13. The surface treatment solution according to claim 12, wherein the metal is at least one selected from the group consisting of copper, aluminum, titanium, nickel, tin, iron, silver, gold, and alloys thereof.

14. The surface treatment solution according to claim 12, wherein the metal is copper or a copper alloy.

15. The surface treatment solution according to claim 12, wherein the inorganic material is at least one selected from the group consisting of silicon, a ceramic and a glass.

16. The surface treatment solution according to claim 15, wherein the ceramic is at least one selected from the group consisting of alumina, silicon carbide, aluminum nitride, silicon nitride, and barium titanate.

17. The surface treatment solution according to claim 12, wherein the resin material is at least one selected from the group consisting of an acrylate resin, an epoxy resin and a polyimide resin.

18. The surface treatment solution according to claim 11, which is used for bonding at least two materials selected from the group consisting of a metal, an inorganic material and a resin material.

19. The surface treatment solution according to claim 18, wherein the metal is at least one selected from the group consisting of copper, aluminum, titanium, nickel, tin, iron, silver, gold, and alloys thereof.

20. The surface treatment solution according to claim 18, wherein the metal is copper or a copper alloy.

21. The surface treatment solution according to claim 18, wherein the inorganic material is at least one selected from the group consisting of silicon, a ceramic and a glass.

22. The surface treatment solution according to claim 21, wherein the ceramic is at least one selected from the group consisting of alumina, silicon carbide, aluminum nitride, silicon nitride, and barium titanate.

23. The surface treatment solution according to claim 18, wherein the resin material is at least one selected from the group consisting of an acrylate resin, an epoxy resin and a polyimide resin.

24. A surface treatment method of metal, comprising bringing the surface treatment solution described in claim 11 into contact with a surface of the metal.

25. The surface treatment method of metal according to claim 24, wherein the metal is at least one selected from the group consisting of copper, aluminum, titanium, nickel, tin, iron, silver, gold, and alloys thereof.

26. The surface treatment method of metal according to claim 24, wherein the metal is copper or a copper alloy.

27. The surface treatment method of metal according to claim 26, wherein before bringing the surface treatment solution into contact with a surface of copper or a copper alloy, an aqueous solution containing a copper ion is brought into contact with the surface of copper or a copper alloy.

28. The surface treatment method of metal according to claim 26, wherein after bringing the surface treatment solution into contact with a surface of copper or a copper alloy, an aqueous acidic solution or an aqueous alkaline solution is brought into contact with the surface of copper or a copper alloy.

29. A surface treatment method of an inorganic material, comprising bringing the surface treatment solution described in claim 11 into contact with a surface of the inorganic material.

30. The surface treatment method of an inorganic material according to claim 29, wherein the inorganic material is at least one selected from the group consisting of silicon, a ceramic and a glass.

31. The surface treatment method of an inorganic material according to claim 30, wherein the ceramic is at least one selected from the group consisting of alumina, silicon carbide, aluminum nitride, silicon nitride, and barium titanate.

32. A surface treatment method of a resin material, comprising bringing the surface treatment solution described in claim 11 into contact with a surface of the resin material.

33. The surface treatment method of a resin material according to claim 32, wherein the resin material is at least one selected from the group consisting of an acrylate resin, an epoxy resin and a polyimide resin.

34. A bonding method between a metal and a resin material, comprising bringing the surface treatment solution described in claim 11 into contact with at least one of the metal and the resin material to form a chemical film on the at least one thereof, and bonding the metal and the resin material to each other through the chemical film.

35. A bonding method between an inorganic material and a resin material, comprising bringing the surface treatment solution described in claim 11 into contact with at least one of the inorganic material and the resin material to form a chemical film on the at least one thereof, and bonding the inorganic material and the resin material to each other through the chemical film.

36. A bonding method between a metal and an inorganic material, comprising bringing the surface treatment solution described in claim 11 into contact with at least one of the metal and the inorganic material to form a chemical film on the at least one thereof, and bonding the metal and the inorganic material to each other through the chemical film.

37. A printed wiring board wherein two materials selected from the group consisting of a metal, an inorganic material and a resin material are bonded through a chemical film formed from the surface treatment solution described in claim 11.

38. An electronic device wherein two materials selected from the group consisting of a metal, an inorganic material and a resin material are bonded through a chemical film formed from the surface treatment solution described in claim 11.

* * * * *